(12) United States Patent
Bazan et al.

(10) Patent No.: US 12,070,463 B2
(45) Date of Patent: Aug. 27, 2024

(54) COMPOSITIONS AND METHODS FOR THE TREATMENT OF SEIZURE CAUSED BY BRAIN TUMOR

(71) Applicants: Board Of Supervisors Of Louisiana State University And Agricultural And Mechanical College, Baton Rouge, LA (US); UNIVERSIDAD DE ALCALÁ, Madrid (ES)

(72) Inventors: Nicolas G. Bazan, New Orleans, LA (US); Alberto E. Musto, New Orleans, LA (US); Julio Alvarez-Builla, Madrid (ES)

(73) Assignees: BOARD OF SUPERVISORS OF LOUISIANA STATE UNIVERSITY AND AGRICULTURAL AND MECHANICAL COLLEGE, Baton Rouge, LA (US); UNIVERSIDAD DE ALCALÁ, Madrid (ES)

( * ) Notice: Subject to any disclaimer, the term of this patent is extended or adjusted under 35 U.S.C. 154(b) by 418 days.

(21) Appl. No.: 16/739,350

(22) Filed: Jan. 10, 2020

(65) Prior Publication Data
US 2020/0323864 A1 Oct. 15, 2020

Related U.S. Application Data

(62) Division of application No. 15/556,719, filed as application No. PCT/US2016/021429 on Mar. 9, 2016, now abandoned.
(Continued)

(51) Int. Cl.
*A61K 31/5377* (2006.01)
*A61K 45/06* (2006.01)
(Continued)

(52) U.S. Cl.
CPC .......... *A61K 31/5377* (2013.01); *A61K 45/06* (2013.01); *A61P 25/00* (2018.01);
(Continued)

(58) Field of Classification Search
None
See application file for complete search history.

(56) References Cited

U.S. PATENT DOCUMENTS 3,760,984 A 9/1973 Theeuwes
3,845,770 A 11/1974 Theeuwes et al.
(Continued)

FOREIGN PATENT DOCUMENTS

EP 0531598 A1 3/1993
WO WO1997027840 A1 8/1997
WO WO2012077775 A1 6/2012

OTHER PUBLICATIONS

Bruna et al. (Expert Rev. Clin. Pharmacol. 6(3), 333-344, 2013).*
(Continued)

*Primary Examiner* — Bong-Sook Baek
(74) *Attorney, Agent, or Firm* — Baker, Donelson, Bearman, Caldwell & Berkowitz, PC

(57) ABSTRACT

Provided are compositions that include a platelet-activating factor antagonist, pharmaceutical compositions including the platelet-activating factor antagonist, methods of treating a modulating the proliferation of a glioma or a pathological condition resulting from patient having a glioma.

4 Claims, 27 Drawing Sheets

Related U.S. Application Data

(60) Provisional application No. 62/253,533, filed on Nov. 10, 2015, provisional application No. 62/130,221, filed on Mar. 9, 2015.

(51) Int. Cl.
  *A61P 25/00* (2006.01)
  *A61P 25/08* (2006.01)
  *A61P 35/00* (2006.01)
  *C07D 211/90* (2006.01)

(52) U.S. Cl.
  CPC ............... *A61P 25/08* (2018.01); *A61P 35/00* (2018.01); *C07D 211/90* (2013.01)

(56) References Cited

U.S. PATENT DOCUMENTS

| | | | |
|---|---|---|---|
| 3,916,899 A | 11/1975 | Theeuwes et al. | |
| 3,923,426 A | 12/1975 | Theeuwes | |
| 3,987,790 A | 10/1976 | Eckenhoff et al. | |
| 3,995,631 A | 12/1976 | Higuchi et al. | |
| 4,016,880 A | 4/1977 | Theeuwes et al. | |
| 4,036,228 A | 7/1977 | Theeuwes | |
| 4,111,202 A | 9/1978 | Theeuwes | |
| 4,111,203 A | 9/1978 | Theeuwes | |
| 4,203,440 A | 5/1980 | Theeuwes | |
| 4,203,442 A | 5/1980 | Michaels | |
| 4,210,139 A | 7/1980 | Higuchi | |
| 4,327,725 A | 5/1982 | Cortese et al. | |
| 4,360,019 A | 11/1982 | Portner et al. | |
| 4,487,603 A | 12/1984 | Harris | |
| 4,627,850 A | 12/1986 | Deters et al. | |
| 4,692,147 A | 9/1987 | Duggan | |
| 4,865,845 A | 9/1989 | Eckenhoff et al. | |
| 5,057,318 A | 10/1991 | Magruder et al. | |
| 5,059,423 A | 10/1991 | Magruder et al. | |
| 5,112,614 A | 5/1992 | Magruder et al. | |
| 5,137,727 A | 8/1992 | Eckenhoff | |
| 5,234,692 A | 8/1993 | Magruder et al. | |
| 5,234,693 A | 8/1993 | Magruder et al. | |
| 5,643,207 A | 7/1997 | Rise | |
| 5,728,369 A | 3/1998 | Griffiths et al. | |
| 5,728,396 A | 3/1998 | Peery et al. | |
| 5,820,589 A | 10/1998 | Torgerson et al. | |
| 5,985,305 A | 11/1999 | Peery et al. | |
| 6,198,966 B1 | 3/2001 | Heruth | |
| 6,566,359 B1* | 5/2003 | Bazan | C07D 249/08 544/82 |
| 2002/0169158 A1* | 11/2002 | Hunt, III | A61K 31/39 514/220 |

OTHER PUBLICATIONS

Vlachogianni et al., Interleukin-1 beta stimulates platelet-activating factor production in U-937 cells modulating both its biosynthetic and catabolic enzymes. Cytokine. (2013) 63(2):97-104.
Vukicevic & Kellenberger Modulatory effects of acid-sensing ion channels on action potential generation in hippocampal neurons. Am. J. Physiol. Cell Physiol. (2004) 287(3):C682-690.
Wemmie et al., Acid-sensing ion channels: advances, questions and therapeutic opportunities. Trends Neurosci. (2006) 29(10): 578-586.
Wemmie et al., The acid-activated ion channel ASIC contributes to synaptic plasticity, learning, and memory. Neuron. (2002) 34(3):463-477.
Xu et al., Acidic extracellular pH induces vascular endothelial growth factor (VEGF) in human glioblastoma cells via ERK1/2 MAPK signaling pathway: mechanism of low pH-induced VEGF. J. Biol. Chem. (2002) 277(13):11368-11374.
Yermolaieva et al., Extracellular acidosis increases neuronal cell calcium by activating acid-sensing ion channel 1a. Proc. Nat. Acad. Sci. U.S.A. (2004) 101(17): 6752-6757.
Yost et al., The platelet activating factor (PAF) signaling cascade in systemic inflammatory responses. Biochimie. (2010) 92(6):692-697.
Zada et al., Incidence trends in the anatomic location of primary malignant brain tumors in the United States: 1992-2006. World Neurosurgery. (2012) 77(4-4):518-524.
Zha et al., Acid-sensing ion channel 1 a is a postsynaptic proton receptor that affords the density of dendritic spines. Proc. Nat. Acad. Sci. U.S.A (2006) 103(44) 16556-16561.
Zha XM. Acid-sensing ion channels: trafficking and synaptic function. Mol. Brain. (2013)6:1.
Zucker & Cao Selective matrix metalloproteinase (MMP) inhibitors in cancer therapy: ready for prime time? Cancer Biol. Therapy. (2009) 8(24):2371-2372.
Belayev, L., et al., LAU-0901, a novel platelet-activating factor antagonist, is highly neuroprotective in cerebral ischemia. Experimental Neurology 214 (2008) 253-258.
Belayev, L., et al., Superior Neuroprotective Efficacy of LAU-0901, a Novel Platelet-Activating Factor Antagonist, in Experimental Stroke. Transl. Stroke Res. (2012) 3:154-163.
Berge et al., 1988, "Pharmaceutically Acceptable Salts," J. Pharm. Sci., vol. 66, pp. 1-19.
Beylaev, L. et al., LAU-0901, a novel platelet-activating factor receptor antagonist, confers enduring neuroprotection in experimental focal cerebral ischemia in the rat. Brain Research 1253 (2009) 184-190.
Buchwald et al. (1980), Surgery 88:507.
Buzsaki, Neuron Nov. 4, 2010; 68(3): 362-385.
Campbell et al., J. Neural Engineering. (2012) 9(2): 026023.
Douw et al., Lancet Neurol. (2009) 8(9): 810-8.
Gardner, C., et al., Platelet-activating factor-induced calcium mobilization and oxidative metabolism in hepatic macrophages and endothelial cells, Journal of Leukocyte Biology (1993) vol. 53, pp. 190-196.
Gati, et al., Prostaglandins Leukot. Essent. Fatty Acids. (1991) 43(2): 103-110.
Gennaro (2000) "Remington: The Science and Practice of Pharmacy," 20th edition, Lippincott, Williams & Wilkins.
Goracci et al., Metabolism and Functions of Platelet-Activating Factor (PAF) in the Nervous Tissue, Handbook of Neurochemistry and Molecular Neurobiology: Neural Lipids (2009) vol. 14, pp. 311-352.
Handbook of Pharmaceutical Excipients (2000) A.H. Kibbe et al., eds., 3rd ed. Amer. Pharmaceutical Assoc.
Hasegawa et al, (2010) PloS ONE 5(5): e10467.
Hirashima et al (1998) J. Neurosurg. 88: 304-307.
Jancar & Chammas Curr Drug Targets. (2014) 15(10):982-987.
Koltai et al., Drugs (1991) 42(1) 9-29.
Kornecki, E. and Ehrlich, Y.H. Calcium Ion Mobilization in Neuronal Cells Induced by PAF, Lipids, vol. 26, No. 12 (1991).
Kornecki & Ehrlich Science (1988) 240(4860): 1792-1794.
Langer (1990). Science 249:1527-1533.
Li et al. (2008) Cell Mol Neurobiol. 28:125-136.
Liu et al., Mediators of Inflammation, vol. 2013, Article ID 407562, 11 pages.
Musto and Samii, 2011, vol. 52, Issue 3, pp. 551-561.
Pharmaceutical dosage form tablets, eds. Liberman et al. (New York, Marcel Dekker, Inc., 1989).
Pharmaceutical Dosage Forms and Drug Delivery Systems (1999) H.C. Ansel et al., ed. 7th ed., Lippincott, Williams & Wilkins.
Pharmaceutical dosage forms and drug delivery systems, 6th Edition, Ansel et al., (Media et al., 1995).
Pharmaceutical Salts: Properties, Selection, and Use, P. Heinrich Stahl (ed), Carmille G. Wermuth (ed), ISBN: 3-90639-026-8, Hardcover, 388 pages, Aug. 2002.
Remington's Pharmaceutical Sciences, Mack Publishing Company, Easton, Pennsylvania, 17th edition, 1985.
Saudek et al. (1989) N. Engl. J. Med. 321:574.
Scatena R. Expert Opinion Investigational Drugs (2000) 9(9): 2159-2165.
Scott & Gibberd Acta Neurologica Scandinavica (1980) 61 (4):227-239.
Sefton (1987) CRC Crit. Ref. Biomed. Eng. 14:201.

(56) References Cited

OTHER PUBLICATIONS

Sfondouris et al., Computers Biol. Med. (2012) 42(1):129-134.
Stafforini et al., Critical Reviews Clin. Lab. Sci (2003) 40(6): 643-672.
Teather et al., 2006 (p. 31 inflammation increases PAF).
Tsoupras et al., Infectious disorders Drug Targets. (2009) 9(4):390-399.
Addae et al., All-trans-retinoid acid induces the differentiation of encapsulated mouse embryonic stem cells into GABAergic neurons. Differentiation (2012) 83(5):233-241.
Akai et al., Modulation of tissue-type plasminogen activator expression by platelet activating factor in human glioma cells. J. NeuroOncology. (2002) 59(3): 193-198.
Alvarado-Rajas et al., Different mechanisms of ripple-like oscillations in the human epileptic subiculum. Annals Neurol. (2014).
Aronica et al., Gene expression profile analysis of epilepsy-associated gangliogliomas. Neuroscience. (2008) 151 (1): 272-292.
Balosso et al., A novel nontranscriptional pathway mediates the proconvulsive effects of interleukin-1 beta. Brain. (2008) 131 (Pt 12):3256-3265.
Bartho et al., Characterization of neocortical principal cells and interneurons by network interactions and extracellular features. J. Neurophysiol. (2004) 92(1 ):600-608.
Bartolomei et al., How do brain tumors alter functional connectivity? A magnetoencephalography study. Annals Neurology. (2006) 59(1):128-138.
Bausch SB. Axonal sprouting of GABAergic interneurons in temporal lobe epilepsy. Epilepsy & Behavior (2005) 7(3):390-400.
Bazan & Tao PAF antagonists as possible inhibitors of corneal epithelial defects and ulceration. J. Ocular Pharmacol. Therapeutics (1997) 13(3):277-285.
Bazan NG. Lipid signaling in neural plasticity, brain repair, and neuroprotection. Mol. Neurobiol. (2005) 32(1):89-103.
Berdiev et al., Acid-sensing ion channels in malignant gliomas. J. Biol. Chem. (2003) 278(17):15023-15034.
Bernard-Trifilo et al., Integrin signaling cascades are operational in adult hippocampal synapses and modulate NMDA receptor physiology. J. Neurochem. (2005) 93(4):834-849.
Blasiak et al., Comparison of T2 and T2*-weighted MR molecular imaging of a mouse model of glioma. BMC Med. Imaging. (2013) 13:20.
Buckingham et al., Glutamate release by primary brain tumors induces epileptic activity. Nature Med. (2011) 17(10): 1269-1274.
Buzsaki et al., Hippocampal network patterns of activity in the mouse. Neuroscience (2003) 116(1 ):201-211.
Buzsaki G. Neural syntax: cell assemblies, synapsembles, and readers. Neuron (2010) 68(3):362-385.
Chagnac-Amitai & Connors BW. Synchronized excitation and inhibition driven by intrinsically bursting neurons in neocortex. J. Neurophysiol. (1989) 62(5):1149-1162.
Chaichana et al., Long-term seizure outcomes in adult patients undergoing primary resection of malignant brain astrocytomas. J. Neurosurgery. (2009) 111 (2):282-292.
Chao & Olson Platelet-activating factor: receptors and signal transduction. Biochem. J. (1993) 292 ( Pt 3):617-629.
Cole-Edwards et al., c-Jun N-terminal kinase activation responses induced by hippocampal kindling are mediated by reactive' astrocytes. J. Neuroscience (2006) 26(32):8295-8304.
Coquery Microvascular MRI and unsupervised clustering yields histology-resembling images in two rat models of glioma. J. Cerebral blood Flow Metabolism (2014) 34(8):1354-1362.
Costa et al., Silencing of the tumor suppressor gene WNK2 is associated with upregulation of MMP2 and JNK in gliomas. Oncotarget. (2014).
Da Fonseca AC, Sadie B. Microglia and macrophages in malignant gliomas: recent discoveries and implications for promising therapies. Clinical Developmental Immunol. (2013) 2013:264124.
Das & Marsden Angiogenesis in glioblastoma. New Eng. J. Med. (2013) 369(16):1561-1563.
Davenport et al., Sprouting of GABAergic and mossy fiber axons in dentate gyrus following intrahippocampal kainate in the rat. Experimental Neurol. 1990) 109(2):180-190.
Dawson et al., Structure of the acid-sensing ion channel 1 in complex with the gating modifier Psalmotoxin 1. Nature Comm. (2012) 3:936.
De Groot et al., Epilepsy in patients with a brain tumour: focal epilepsy requires focused treatment. Brain (2012) 135 (Pt4):1002-1016.
Desland et al., Manual versus Automated Rodent Behavioral Assessment: Comparing Efficacy and Ease of Bederson and Garcia Neurological Deficit Scores to an Open Field VideoT racking System. J. Central Nervous System Dis.(2014) 6:7-14.
Douw et al., The lesioned brain: still a small-world? Frontiers Hum Neurosci. (2010) 4:174.
Edwards & Berry The efficiency of simulation-based multiple comparisons. Biometrics. (1987) 43(4):913-928.
Ehtesham et al., The role of the CXCR4 cell surface chemokine receptor in glioma biology. J. neuro-oncology. (2013) 113(2): 153-162.
Engel et al., Expression of neurogenesis genes in human temporal lobe epilepsy with hippocampal sclerosis. Int. J. human temporal lobe epilepsy with hippocampal sclerosis. Int. J. Physiol. Pathophysiol. Pharmacol. (2011 ) 3(1):38-47.
Englot et al., Characteristics and treatment of seizures in patients with highgrade glioma: a review. Neurosurgery Clinics North Am. (2012) 23(2):227-235.
Escoubas et al., Structure and pharmacology of spider venom neurotoxins. Biochimie. (2000) 82(9-1 0):893-907.
Farooqui AA. Lipid mediators in the neural cell nucleus: their metabolism, signaling, and association with neurological disorders. Neuroscientist (2009) 15(4):392-407.
Flasinski et al., Influence of platelet-activating factor, lyse-platelet activating factor and edelfosine on Langmuir monolayers imitating plasma membranes of cell lines differing in susceptibility to anti-cancer treatment: the effect of plasmalogen level. J. R. Soc Interface. (2014) 11(95):20131103.
Garau et al., Development of a systemically-active dual CXCR1/CXCR2 allosteric inhibitor and its efficacy in a model of transient cerebral ischemia in the rat. Euro. Cytokine Network. (2006) 17(1):35-41.
Ghosh et al., Automated corepenumbra quantification in neonatal ischemic brain injury. J Cereb. Blood Flow Metab. (2012) 32(12):2161-2170.
Ghosh et al., Automated detection of brain abnormalities in neonatal hypoxia ischemic injury from MR images. Med. Image. Anal. (2014) 18(7):1059-1069.
Glantz et al., Practice parameter: anticonvulsant prophylaxis in patients with newly diagnosed brain tumors. Neurology.(2000) 54(10):1886-1893.
Goel et al., Morphological changes and stress responses in neurons in cerebral cortex infiltrated by diffuse astrocytoma. Neuropathol. (2003) 23(4):262-270.
Gomes et al., Exogenous platelet-activating factor acetyl hydrolase reduces mortality in mice with systemic inflammatory response syndrome and sepsis. Shock (Augusta, Ga). (2006) 26(1 ):41-49.
Gruol et al., Hydrogen ions have multiple effects on the excitability of cultured mammalian neurons. Brain Res. (1980) 183(1):247-252.
Hanahan OJ. Platelet activating factor: a biologically active phosphoglyceride. Ann. Rev. Biochem. (1986) 55:483-509.
Hattermann et al., The CXCL 16-CXCR6 chemokine axis in glial tumors. J. Neuroimmunol. (2013) 260(1-2):47-54.
He et al., Alkali-induced corneal stromal melting prevention by a novel platelet-activating factor receptor antagonist. Arch. Ophthalmol. (2006) 124(1 ):70-8.
He et al., The induction of an angiogenic response in corneal myofibroblasts by platelet-activating factor (PAF). Current Eye Res. (2010) 35(12):1063-1071.
Hirashima et al., Maturation of embryonic stem cells into endothelial cells in an in vitro model of vasculogenesis. Blood.(1999) 93(4):1253-1263.

(56) References Cited

OTHER PUBLICATIONS

Houser & Esclapez Vulnerability and plasticity of the GABA system in the pilocarpine model of spontaneous recurrent seizures. Epilepsy Res. (1996) 26(1):207-218.
Hu et al., Glioma-associated microglial MMP9 expression is upregulated by TLR2 signaling and sensitive to minocycline. Int. J. Cancer (2014) 135(11) :2569-2578.
Hu et al., Glioma-derived versican promotes tumor expansion via glioma-associated microglial/macrophages Toll-like receptor 2 signaling. Neurooncol. (2015) 17(2):200-210.
International Search Report for PCT/US2016/021429 mailed Jun. 20, 2016.
Jeffes et al., Antiangiogenic drugs synergize with a membrane macrophage colony-stimulating factor-based tumor vaccine to therapeutically treat rats with an established malignant intracranial glioma. J Immunol. (Mar. 1, 2005) 174 (5):2533-2543.
Kalia LV, Salter MW. Interactions between Src family protein tyrosine kinases and PSD-95. Neuropharmacol. (2003) 45(6):720-728.
Kapoor & O'Rourke SIRP alpha1 receptors interfere with the EGFRviii signalosome to inhibit glioblastoma cell transformation and migration. Oncogene. (2010) 29(29):4130-4144.
Kerkhof & Vecht Seizure characteristics and prognostic factors of gliomas. Epilepsia. (2013) 54 Suppl 9: 12-17.
Kim et al., ECM stiffness regulates glial migration in Drosophila and mammalian glioma models. Development. (2014) 141 (16):3233-3242.
Kim et al., PAF enhances MMP-2 production in rat aortic VSMCs via a beta-arrestin2-dependent ERK signaling pathway. J. Lipid Res. (2013) 54(1 0):2678-2686.
Klausberger T. GABAergic interneurons targeting dendrites of pyramidal cells in the CA 1 area of the hippocampus. Euro. J. Neuroscience. (2009) 30(6):947-957.
Kohling et al., Epileptiform activity preferentially arises outside tumor invasion zone in glioma xenotransplants. Neurobiol. Disease. (2006) 22(1):64-75.
Krishtal O. The ASICs: signaling molecules? Modulators? Trends Neurosci. (2003) 26(9):477-483.
Kuruvilla et al., Platelet-activating factor induces the tyrosine phosphorylation and activation of phospholipase C gamma 1, Fyn and Lyn kinases, and phosphatidylinositol 3-kinase in a human B cell line. J. Immunol. (1994) 153 (12):5433-5442.
Kweon & Suh Acid-sensing ion channels (ASICs): therapeutic targets for neurological diseases and their regulation. BMB Reports. (2013) 46(6):295-304.
Lacerda-Queiroz et al., Platelet-activating factor receptor is essential for the development of experimental cerebral malaria. Am. J. Pathol. (2012) 180(1 ):246-255.
Larjavaara et al., Incidence of gliomas by anatomic location. NeuroOncol. (2007) 9(3):319-325.
Li et al., Data analysis and tissue type assignment for glioblastoma multiforme. BioMed. Res. Int. (2014) 2014:762126.
Loscher W. Critical review of current animal models of seizures and epilepsy used in the discovery and development of new antiepileptic drugs. Seizure. (2011) 20(5):359-368.
Lu et al., Docosahexaenoic acid suppresses neuroinflammatory responses and induces heme oxygenase-1 expression in BV-2 microglia: implications of antidepressant effects for omega-3 fatty acids. Neuropsychopharmacol. (2010) 35(11 ):2238-2248.
Luo et al., Dasatinib (BMS-354825) pharmacokinetics and pharmacodynamic biomarkers in animal models predict optimal clinical exposure. Clin Cancer Res. (2006) 12(23):7180-7186.
Lv et al., ASIC1 a polymorphism is associated with temporal lobe epilepsy. Epilepsy Res. (2011) 96(1-2):74-80.
Marotta et al., Mechanisms underlying the nociceptive responses induced by platelet-activating factor (PAF) in the rat paw. Biochem Pharmacol. (2009) 77(7):1223-1235.
Marrero et al., Therapeutic efficacy of aldoxorubicin in an intracranial xeftograft mouse model of human glioblastoma. Neoplasia. (2014) 16(10):874-82.

Mazereeuw et al., Platelet-activating factors are associated with cognitive deficits in depressed coronary artery disease patients: a hypothesis-generating study. J. Neuroinflammation. (2014) 11: 119.
Munson et al., Identifying new small molecule antiinvasive compounds for glioma treatment. Cell Cycle. (2013) 12 (14):2200-2209.
Musto et al., Different phases of after discharge during rapid kindling procedure in mice. Epilepsy Res. (2009) 85 (2-3): 199-205.
Musto et al., Hippocampal neuro-networks and dendritic spine perturbations in epileptogenesis are attenuated by neuroprotectin d1. PloS One. (2015) 10(1) :e0116543.
Musto et al., The omega-3 fatty acid-derived neuroprotectin D1 limits hippocampal hyperexcitability and seizure susceptibility in kindling epileptogenesis. Epilepsia. (2011) 52(9): 1601-1608.
Najbauer et al., Cellular host responses to gliomas. PloS One. (2012) 7(4):e35150.
Nelson et al., The sodium channel-blocking antiepileptic drug phenytoin inhibits breast tumour growth and metastasis. Mol Cancer. (2015) 14:13.
N'Gouemo P. Amiloride delays the onset of pilocarpine-induced seizures in rats. Brain Res. (2008) 1222:230-232.
Obenaus et al., Long-term magnetic resonance imaging of stem cells in neonatal ischemic injury. Ann Neural. (2011) 69(2):282-291.
Okubo et al., Up-regulation of platelet-activating factor synthases and its receptor in spinal cord contribute to development of neuropathic pain following peripheral nerve injury. Mol Pain. (2012) 8:8.
Ottine & Bazan HE. Corneal stimulation of MMP-1, -9 and uPA by platelet-activating factor is mediated by cyclooxygenase-2 metabolites. Current Eye Res. (2001) 23(2):77-85.
Otto et al., siCAM-1 and TNFalpha induce MIP-2 with distinct kinetics in astrocytes and brain microvascular endothelial cells. J. Neurosci. Res. (2000) 60(6):7337-42.
Pagliara et al., Protease Nexin-1 affects the migration and invasion of C6 glioma cells through the regulation of urokinase Plasminogen Activator and Matrix Metalloproteinase-9/2. Biochimica Biophysica Acta. (2014) 1843 (11):2631-2644.
Prakash et al.. Gliomas and seizures. Medical Hypotheses, (2012) 79(5):622-626.
Racine RJ. Modification of seizure activity by electrical stimulation. I. After-discharge threshold. Electroencephalogr. Clin. Neurophysiol. (1972) 32(3):269-279.
Racine RJ. Modification of seizure activity by electrical stimulation. II. Motor seizure. Electroencephalogr. Clin. Neurophysiol. (1972) 32(3):281-94.
Ramaswamy et al., Activation of NMDA receptor of glutamate influences MMP-2 activity and proliferation of glioma cells. Neurological Sci (2014) 35(6):823-829.
Richter et al., Glioma-associated microglia and macrophages/monocytes display distinct electrophysiological properties and do not communicate via gap junctions. Neurosci. Lett. (2014) 583:130-135.
Rosati et al., Epilepsy in cerebral glioma: timing of appearance and histological correlations. J. NeuroOncology. (2009) 93(3):395-400.
Rossi et al., Inhibition of Myosin light-chain kinase attenuates cerebral edema after traumatic brain injury in postnatal mice. J. Neurotrauma. (2013) 30 (19): 1672-1679.
Sadoshima & Okada Asymptomatic cerebrovascular diseases]. Fukuoka Igaku Zasshi (Hukuoka Acta Medica. (1992) 83(10):363-366.
Sanabria et al., Initiation of network bursts by $Ca^{2+}$-dependent intrinsic bursting in the rat pilocarpine model of temporal lobe epilepsy. J. Physiol. (2001) 532(Pt1):205-216.
Shamji et al., Brain tumors and epilepsy: pathophysiology of peritumoral changes. Neurosurg Rev. (2009) 32 (3):275-284.
Somjen GG. Acidification of interstitial fluid in hippocampal formation caused by seizures and by spreading depression Brain Res. (1984) 311(1):186-188.
Souza et al., The essential role of the intestinal microbiota in facilitating acute inflammatory responses. J. Immunol. (2004) 173(6):4137-4146.
Umemori et al., Impairment of N-methyl-0-aspartate receptor-controlled motor activity in LYN-deficient mice. Neuroscience. (2003) 118(3):709-713.

(56) References Cited

OTHER PUBLICATIONS

Vezzani & Friedman Brain inflammation as a biomarker in epilepsy. Biomark Med. (2011) 5(5):607-614.

* cited by examiner

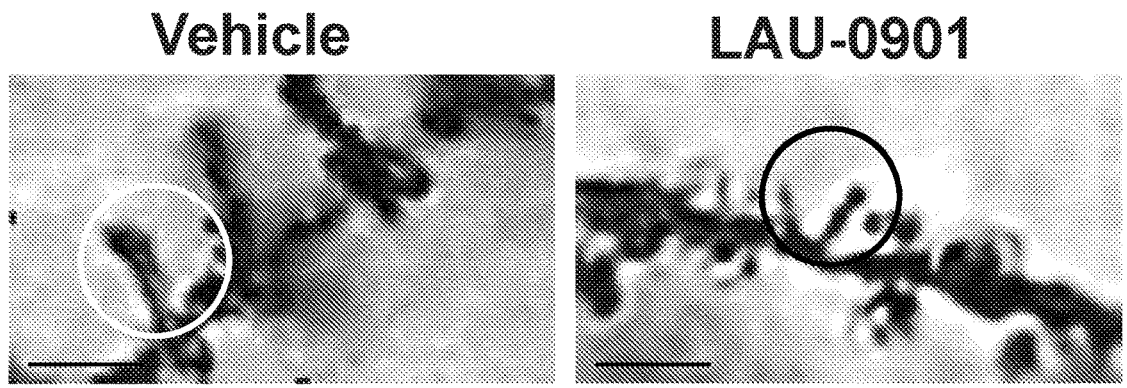
Fig. 12A
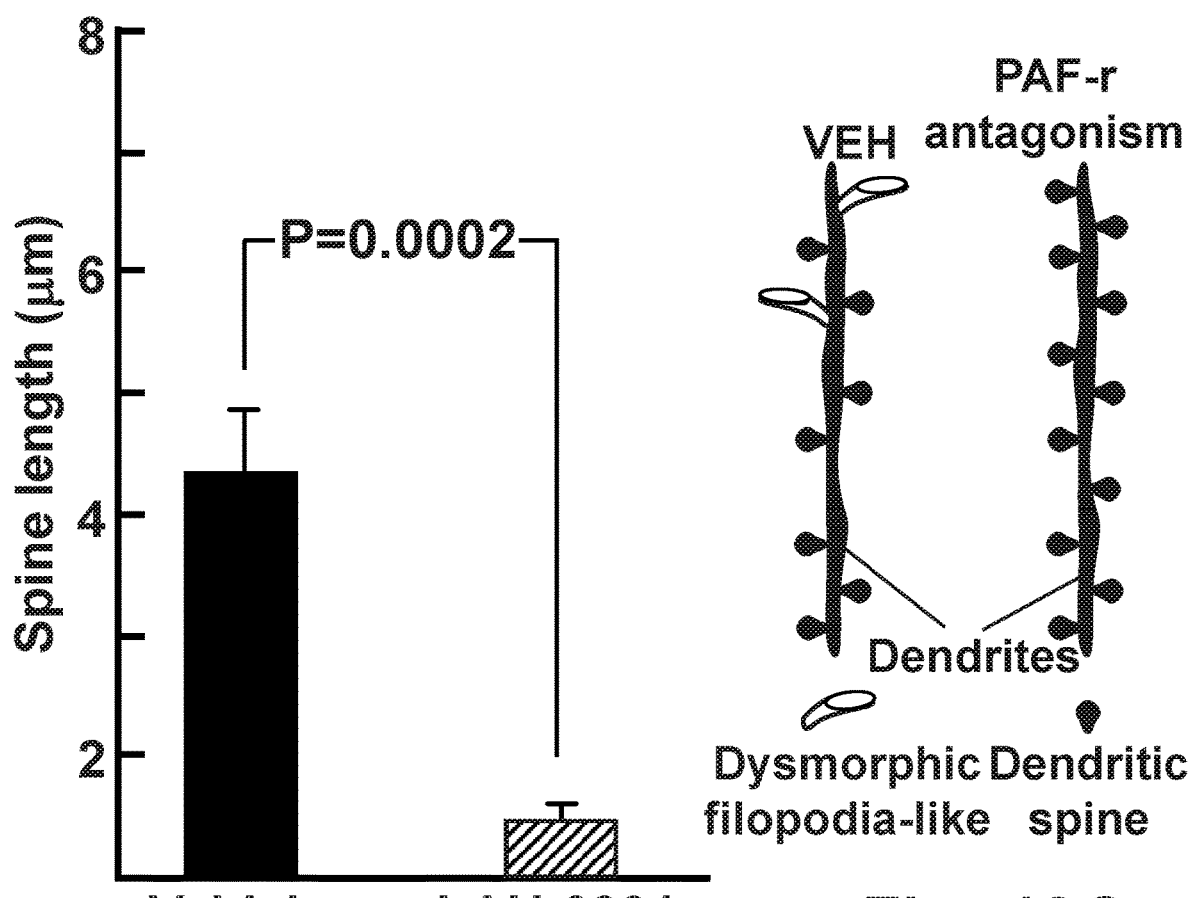
Fig. 12B
Fig. 12C

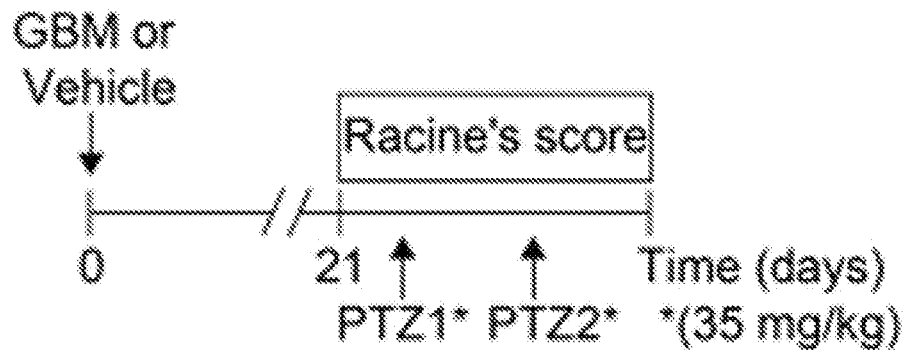
Fig. 14A
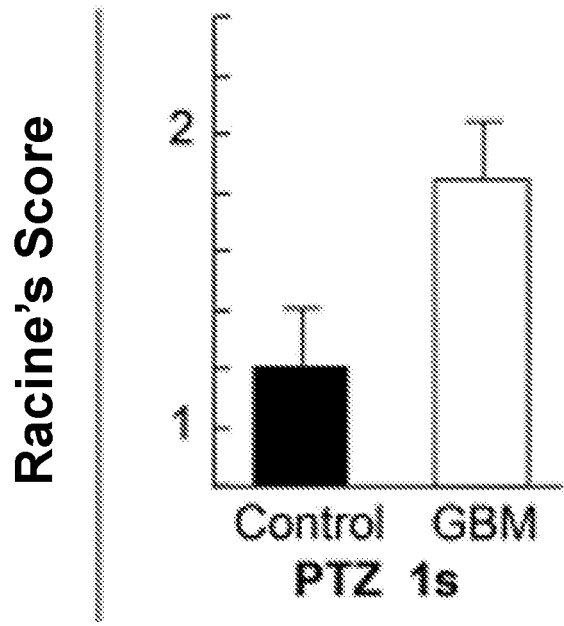
Fig. 14B
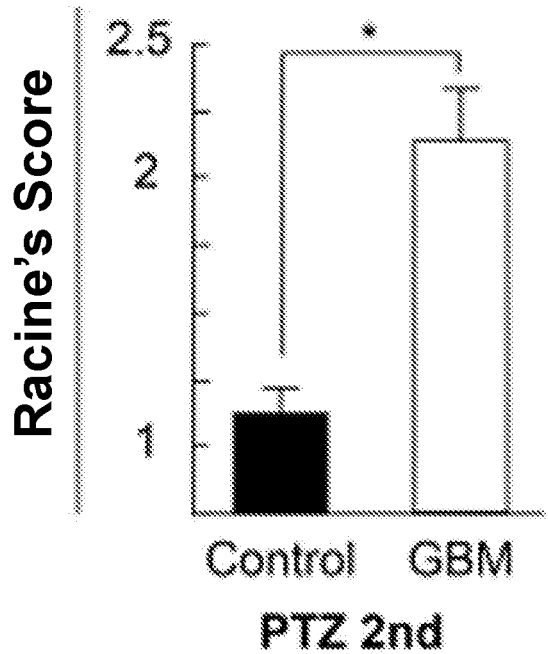
Fig. 14B CON'T

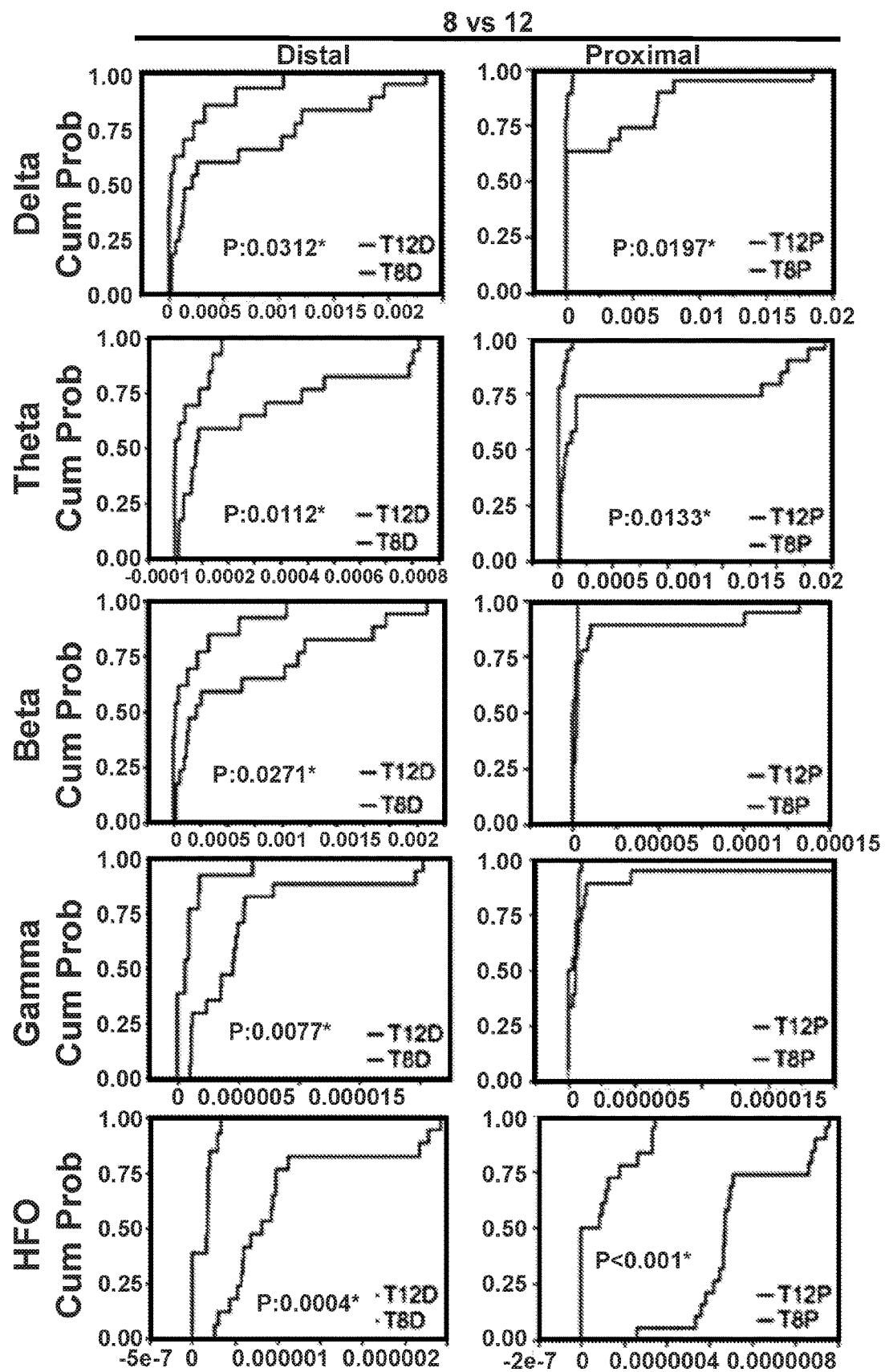
Fig. 16-cont'd

COMPOSITIONS AND METHODS FOR THE TREATMENT OF SEIZURE CAUSED BY BRAIN TUMOR

CROSS-REFERENCE TO RELATED APPLICATIONS

This application is a division of U.S. patent application Ser. No. 15/556,719, filed on Sep. 8, 2017, which is a § 371 national stage entry of PCT/US2016/021429, filed Mar. 9, 2018, which claims priority to U.S. Provisional Patent Application Ser. No. 62/130,221 entitled "COMPOSITIONS AND METHODS FOR THE TREATMENT OF GLIOBLASTOMA" and filed Mar. 9, 2015, and to U.S. Provisional Patent Application Ser. No. 62/253,533 entitled "COMPOSITIONS AND METHODS FOR THE TREATMENT OF GLIOBLASTOMA" and filed Nov. 10, 2015, the entireties of which are hereby incorporated by reference.

STATEMENT REGARDING FEDERALLY SPONSORED RESEARCH OR DEVELOPMENT

This invention was made with government support under P30 GM103340 awarded by the National Institutes of Health. The government has certain rights in the invention.

TECHNICAL FIELD

The present disclosure is generally related to compounds and compositions thereof effective as antagonists of Platelet Activating Factor Receptor (PAF-r). The present disclosure is further related to methods of use of the compounds of the disclosure for neuroprotection in a patient.

BACKGROUND

Gliablastoma Multiforme (alternatively a "Grade IV" "astrocytoma") (GBM) is a malignant cancer of the brain with rapid growth and infiltration, high resistance to current therapies, and a poor survival rate (Prakash et al., 2012). GBM is a devastating brain cancer that typically results in death in the first 15 months after diagnosis. The NCI estimates that 22,910 adults will be diagnosed with brain and other nervous system tumors in 2012, and that 13,700 of these diagnoses will result in death. GBM accounts for about 15 percent of all brain tumors and primarily occurs in adults between the ages of 45 and 70.

Seizures in GBM patients are difficult to control and increase the risk of mortality and poor quality of life (Glantz et al., 2000; Rosati et al., 2009). In addition, some seizures in patients with GBM are resistant to current anticonvulsive drugs, and the adverse effects of some of these drugs aggravate the prognosis not only for seizures but also for GBM further growth and invasion (de Groot et al., 2012; Englot et al., 2012; Glantz et al., 2000). Seizure-free outcome at 12 months following surgery is 77% (Kerkhof et al., 2013). However, about 15% of patients show ongoing seizure activity despite different therapeutic regimens (Kerkhof et al., 2013). A recurrence of seizures following a period of longstanding post-operative seizure control or worsening of seizure control is associated with tumor progression following first-line treatment (Chaichana et al., 2009).

GBM is a fast-growing central nervous system tumor that forms from glial (supportive) tissue of the brain and spinal cord and has cells that took very different from normal cells. Glioblastoma usually occurs in adults and affects the brain more often than the spinal cord.

SUMMARY

One aspect of the disclosure encompasses embodiments of a composition comprising at least one compound having the formula I, or a pharmaceutically acceptable salt thereof:

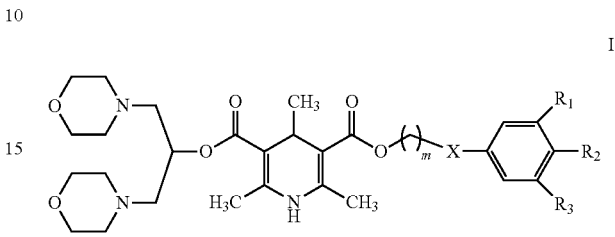

I wherein: m is 1-4, X is O or S, $R_1$ and $R_3$ are independently H or Cl. $R_2$ is H, butoxy, or Cl, and wherein, when: $R_2$ is butoxy, m is 1 or 4, and when $R_1$ and $R_2$ are both Cl, and X is O, m is 3 or 4.

Another aspect of the disclosure encompasses embodiments of a method for treating or inhibiting a brain tumor or a pathological effect thereof, in a subject, the method comprising the steps: (a) selecting a subject in need of treatment, wherein the subject has been diagnosed with a brain tumor or a pathological effect of a brain tumor and (b) administering a therapeutic composition comprising a therapeutically effective amount of a platelet-activating factor receptor antagonist and a pharmaceutically acceptable earner, wherein the PAF receptor antagonist is according to formula I, or a pharmaceutically acceptable salt thereof:

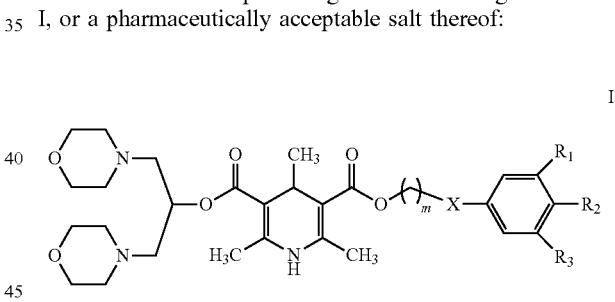

I wherein, m is 1-4, X is O or S, $R_1$ and $R_3$ are independently H or Cl, $R_2$ is H, butoxy, or Cl, and wherein, when: $R_2$ is butoxy, in is 1 or 4, and when $R_1$ and $R_2$ are both Cl, and X is O, m is 3 or 4.

In some embodiments of the disclosure an advantageous platelet-activating factor (PAF) receptor antagonist having the formula:

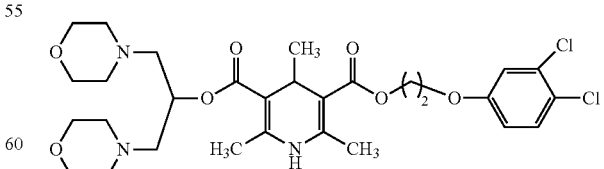

LAU-0901

Yet another aspect of the disclosure encompasses embodiments of a kit comprising a first vessel containing a platelet-activating factor receptor antagonist compound according to the disclosure, optionally a second vessel containing a pharmaceutically acceptable carrier, and instructions for the preparation of a pharmaceutically acceptable composition comprising an amount of the compound known to antagonize platelet-activating factor receptor that is therapeutically effective in treating a brain tumor or a pathological effect of said brain tumor when administered to a subject.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 2A is a digital image illustrating GBM cells (U87MG integrated luciferase reporter gene Cherry) expressing Fyn.

FIG. 2B is a digital image of a gel analysis of Fyn and Lyn expressed by different cell lines.

FIG. 2C illustrates U87MG cells implanted in the dorsal hippocampus of female BALB/c (nu/nu) mice and visualized in vivo at different weeks.

FIG. 2D illustrates tumor initiating cells (circle) in a hippocampus and a GBM mass stained with cresyl violet.

FIG. 2E is a graph illustrating GBM volume associated with progressive cachexia.

FIG. 2F illustrates progressive cachexia at weeks 5 and 6 after GBM implantation.

FIG. 3A shows a series of representative images from saline and PAF-r antagonist LAU-0901-treated mice. A large GBM mass is present in saline-treated mice. In contrast, tumor size is dramatically reduced by LAU-0901 mice during the 10 week-survival period.

FIG. 3B is a graph illustrating that LAU-0901 treatment diminished tumor size on day 25 by 80% compared to saline-treated group. Tumor size before treatment on day 10 was identical in both groups.

FIG. 3C is a graph showing that body weight increased in LAU-0901-treated mice at weeks 8 and 10 compared to saline group. Values are means±SD, *$P<0.05$ (two-way repeated-measures ANOVA).

FIG. 6A is a schematic representation of probe implantation into the dorsal CA3 hippocampal region in female BALB/c (nu/nu) mice and spontaneous LFP recordings from peritumoral sites showing the high amplitude of epileptiform activity distal to the GBM.

FIG. 6B shows a freely-moving mouse 12 days after GBM xenograph implant.

FIG. 6C shows that a higher number of spikes are present distally to the tumor. Dot: values; diamonds: interval of confidence; line bisecting diamond: group mean; vertical bar: standard deviation; vertical box: quantile; large horizontal line: grand mean.

FIG. 6D illustrates the spontaneous generalization of epileptic discharges in the peritumoral area on day 21 alter a xenograph implant. Values are means±SD; *$P<0.05$ (two-way repeated-measures ANOVA).

BABL/c (nu/nu) mice received compound LAU-0901 (60 mg/kg; i.p.) or saline daily for 5 days 24 h after SE.

Figure 11A:
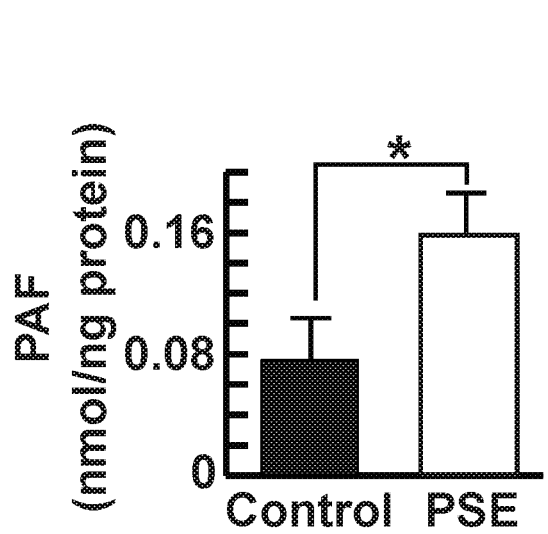
FIGS. 11A-11C illustrate that a PAF-r antagonist reduces seizure susceptibility.

FIG. 11A is a graph showing that a hippocampal PAF pool size, measured by LC-MS/MS, increased at 24 h alter termination of SE.

Figure 11B:
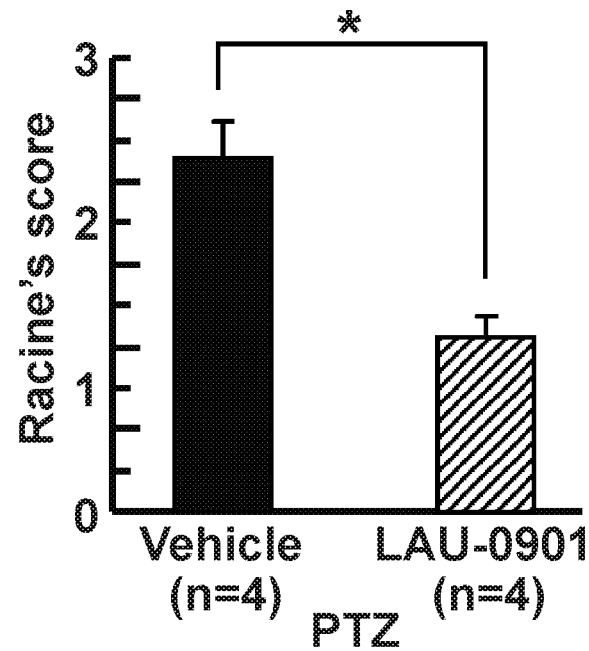

FIG. 11B is a graph illustrating that the PAF-r antagonist LAU-0901 reduced seizure severity.

Figure 11C:
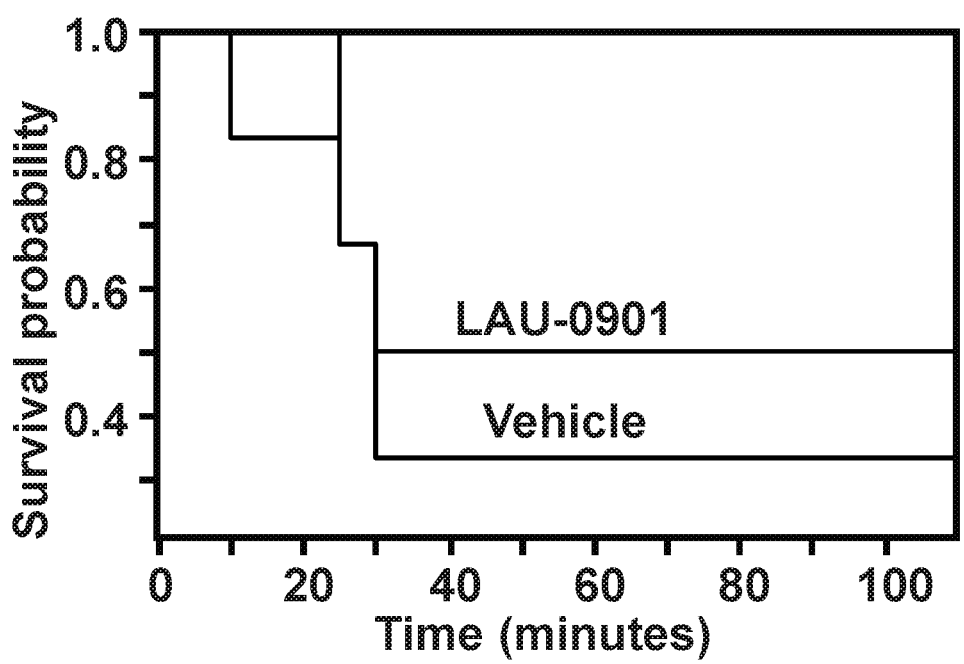

FIG. 11C is a graph illustrating an Unproved survival rate compared to the vehicle-treated group. Values are means±SD; *P<0.05 (two-way repeated-measures ANOVA).

FIGS. 12A-12C illustrate that PAF-r antagonism prevents dysmorphic filopodia-like projections in epileptogenesis.

FIG. 12A illustrates Golgi staining showing dysmorphic filopodia-like spines (circled) from vehicle- and LAU-0901-treated mice 7 days after SE. Scale bar indicates 5 μm.

FIG. 12B is a graph showing the average spine length for dysmorphic filopodia-like spines increased in the vehicle-treated compared to the LAU-0901-treated group.

FIG. 12C is a diagram presenting dysmorphic filopodia-like dendritic spines in vehicle- and LAU-0901-treated mice. Values are means±SD; *P<0.05 (two-way repeated-measures ANOVA)

Figure 13:
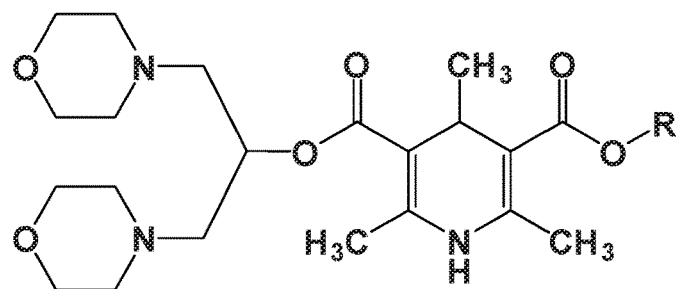
Figure 13:
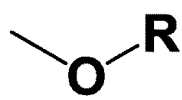
Figure 13:
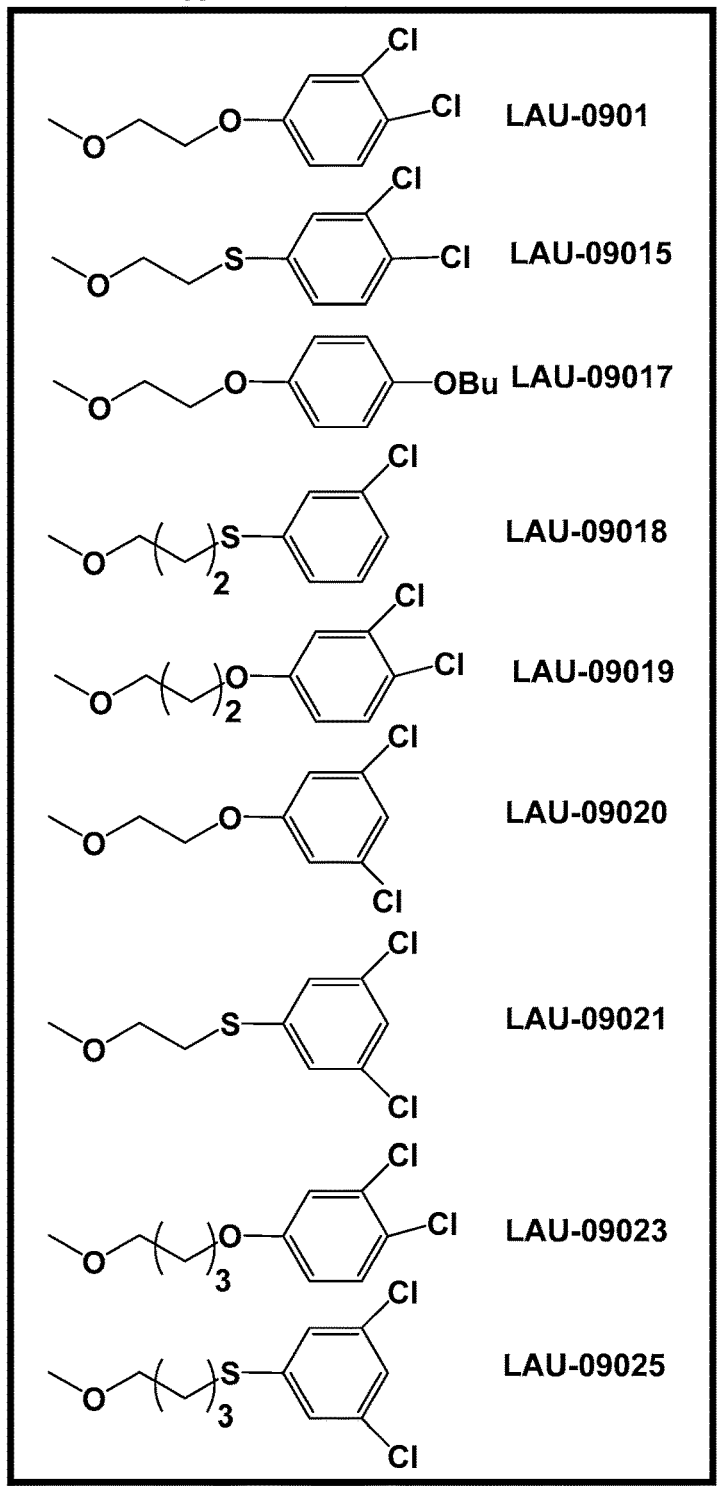

FIG. 13 shows the molecular structures of novel PAF antagonist compounds, including LAU-0901.

FIGS. 14A and 14B illustrate hippocampal GBM triggers seizure susceptibility.

FIG. 14A illustrates seizure susceptibility using PTZ test at 19 days after GBM cell implantation in hippocampus in female BALB/c (nu/nu) mice. Sub-convulsive doses of PTZ were repeated at one hour intervals to obtain seizures and survival of mice; Racine's score was used to quantify seizure severity.

Figure 15:
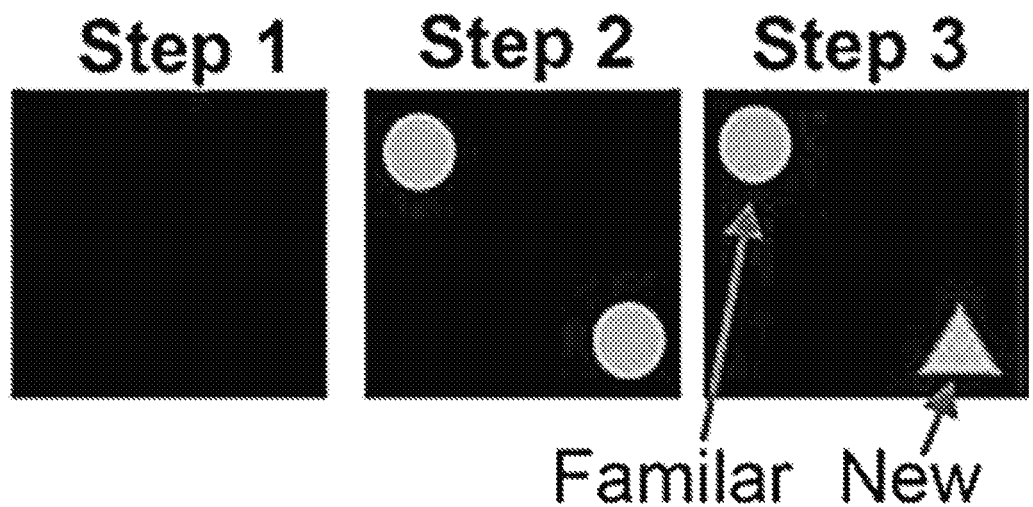
Figure 15:
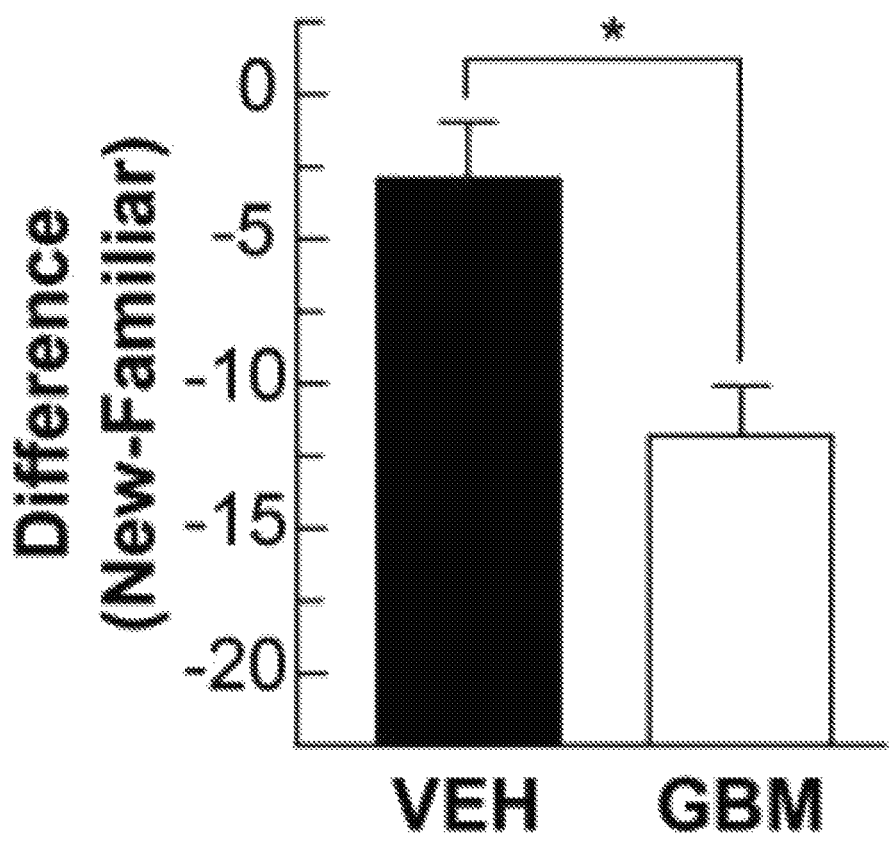

FIG. 14B illustrates that GBM mice (n=3) show higher seizure severity compared with controls (n=5); Bars indicate means, and error bars represent±S.E.M; t-test, *: p=0.01, control mice had only solution infused into the dorsal hippocampus FIG. 15 illustrates that hippocampal GBM induces a memory deficit. Novel object recognition paradigm showing that GBM cells implanted in female BALB/c (nu/nu) mice (n=9). GBM mice spent more time with familiar objects than unfamiliar compared with control (vehicle) mice (n=4). Bars indicate means, and error bars represent±S.E.M T-test, *: p=0.009.

Figure 16:
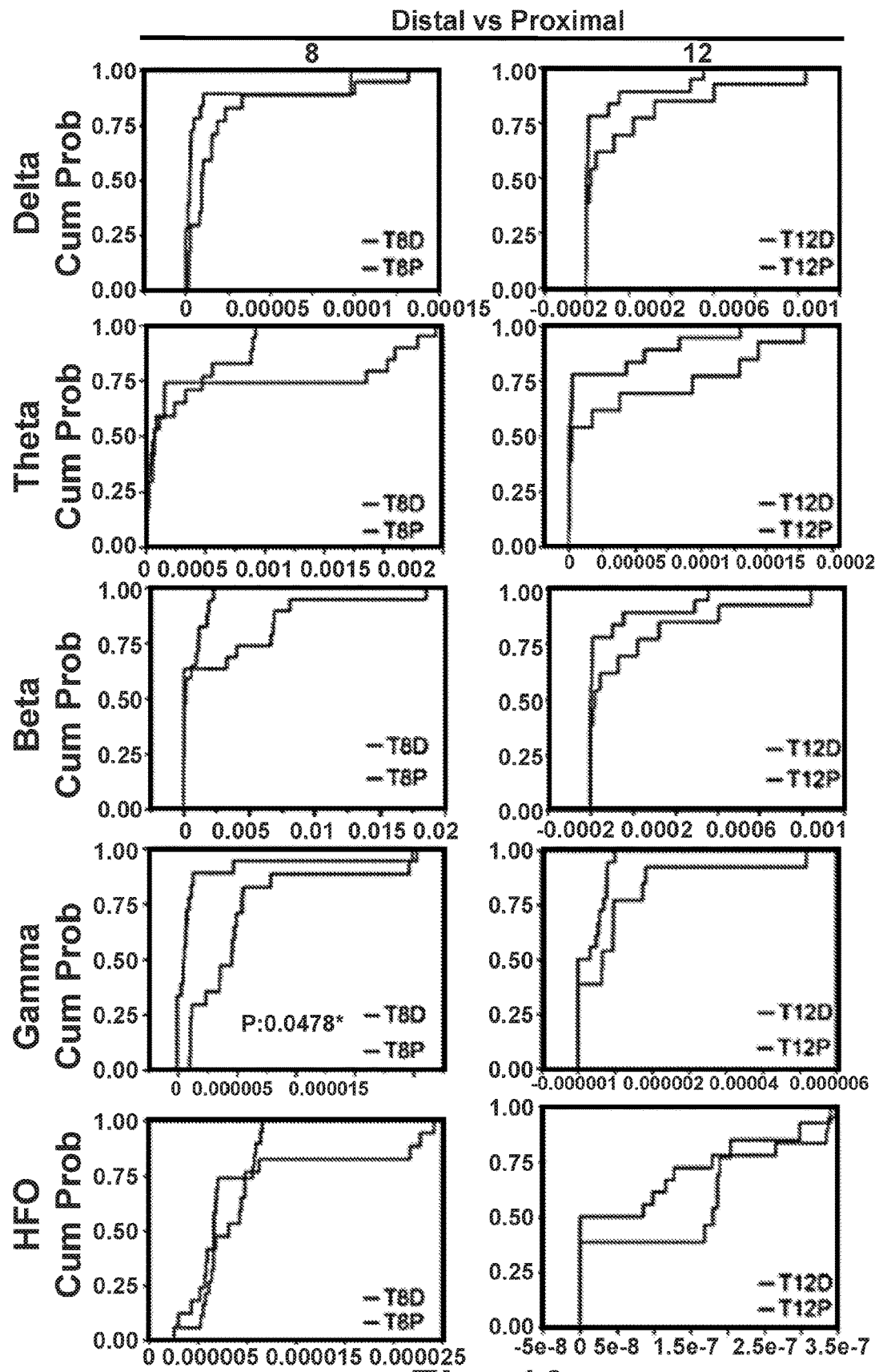

FIG. 16 shows a series of graphs illustrating hippocampal GBM disrupts peritumoral neuronal networks. In vivo frequency analysis of peritumoral region (distal vs. proximal) and at 8 and 12 days after GBM cell implantation in in female BALS/c (nu/nu) mice (n=4,) from LFP recordings obtained from 16 channels (19 samples, each time point, per mouse) chronically implanted in hippocampus showing different bands (Delta, Theta, Beta, Gamma and HFO and expressed as cumulative probability. Gamma and HFO increased in distal regions. Meanwhile HFO remained higher during GBM progression from proximal region. ANOVA, P=p values.

Figure 17:
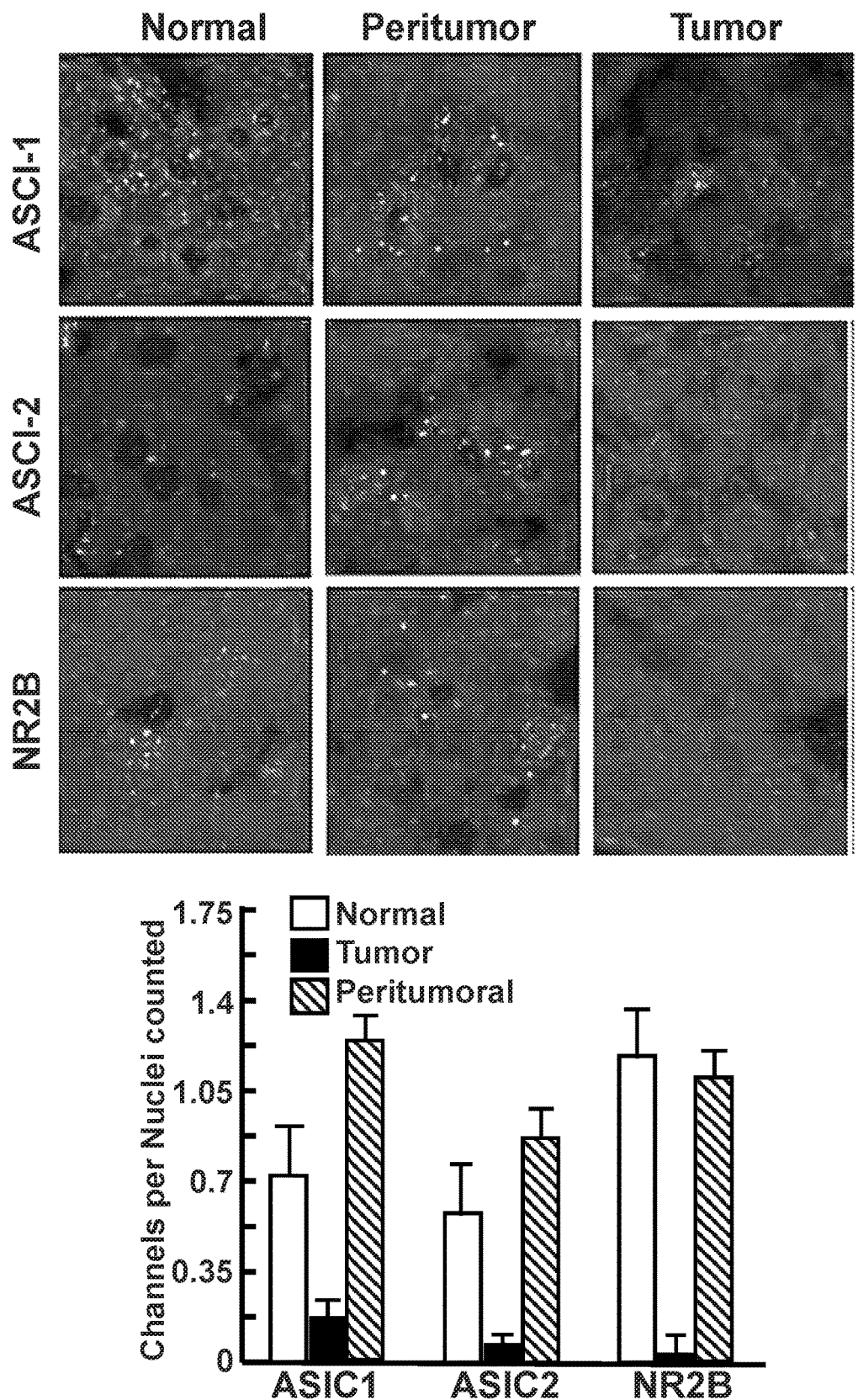

FIG. 17 illustrates that GBM promotes an increase of ASIC-1,2 channels in peritumoral tissue. Representative microphotographs show acid-sensing channels 1 and 2 (ASIC-1, ASIC-2) and glutamate receptor NMDA subunit Nr2b expression in normal tissue, peritumoral and tumoral area as revealed using immunohistology at 4 wks of GBM implantation in female BALB/c (nu/nu) mice. Lower graph illustrates quantification of puncta of ASIC-1, ASIC-2 and Nr2b per nuclei in normal peritumoral and tumoral tissue. There was an increase of ASIC-1 and ASIC-2 compared with normal tissue and tumor area; meanwhile, Nr2b has similar levels in peritumoral and control. Bars indicate means, and error bars represent ±S.E.M.

Figure 18:
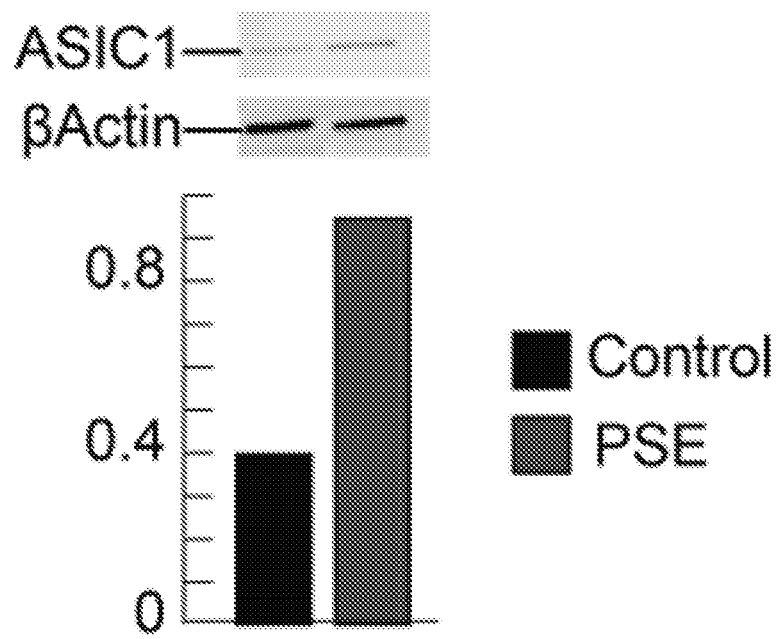

FIG. 18 illustrates that ASIC-1 increases in epileptogenesis. Hippocampal synaptosome from hippocampal tissues one week after SE (PSE) or control mice showed that ASIC-concentration 1 increased in epileptogenesis mice compared with controls.

Figure 19:
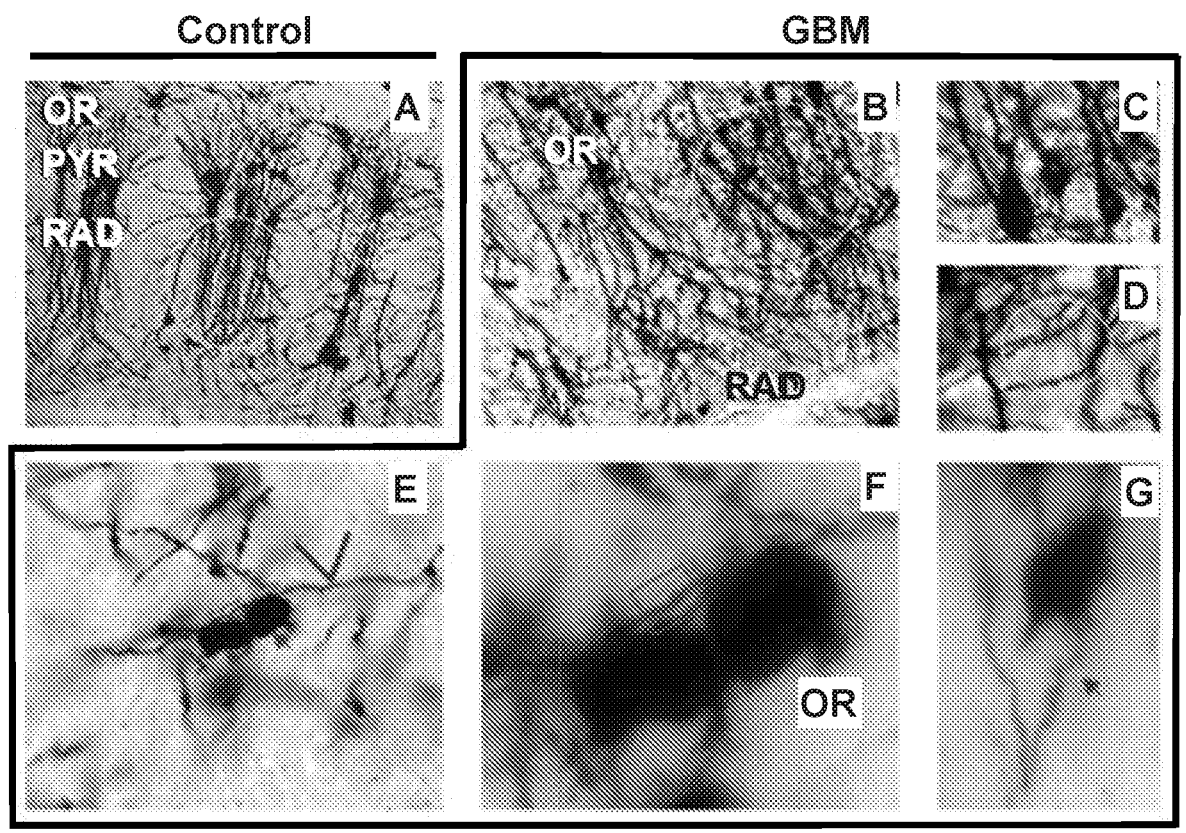

FIG. 19 illustrates that GBM cells invade abnormal neuronal projections: Panels A-B: Representative coronal section of dorsal hippocampus showing pyramidal projections (circle) from GBM peritumoral tissue (Panel B) using Golgi staining after 14 days of GBM implant Panels C-D, aberrant projections in peritumoral tissue, Panels E-F: GBM cells (arrows) attached to dendrites (square) from pyramidal projection (open arrow); Panel G: tortuous neural projection (arrow) attached from GBM cell.

Figure 20:
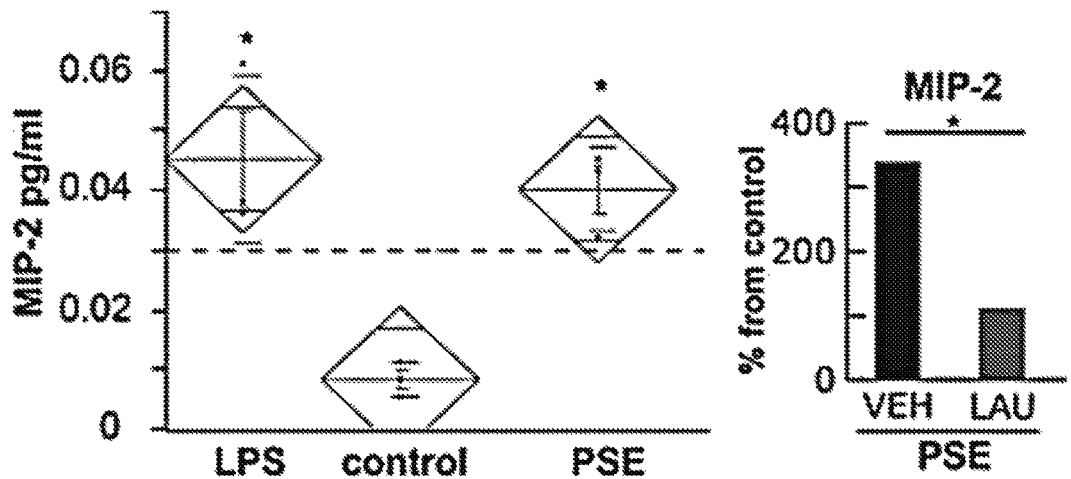

FIG. 20 illustrates that PAF-r antagonist limits chemokine MIP-2. MIP-2 increased in hippocampus after neuroinflammation induced by systemic administration of lipopolysaccharide (LPS) or one week after status epilepticus (PSE). LAU-0901 (60 mg/kg/daily for 5 days; i.p.) reduces hippocampal levels of MIP-2 compared with vehicle. MIP-2 was measured using bead-based immunodetection respectively. Diamonds: interval of confidence; diamond internal horizontal line; group mean; bar lines; standard deviation. Data represent average and bars±S.E.M; n=3 of each group. ANOVA one way, *=p<0.05.

FIGS. 21A-21D illustrate that epileptic seizures induce activation of Lyn kinase and increase of ASIC-1 in hippocampal synapsis.

Figure 21A:

FIG. 21A shows that PAF-r antagonism attenuates Lyn in synapsis. Cell lysates containing equal amounts of protein from hippocampal tissues one week after SE, (PSE) or control mice were either immunoprecipitated using anti-Lyn antibodies and analyzed for tyrosine phosphorylation of Lyn using anti-p-Tyr (top row) or analyzed for total Lyn protein by Western blot analysis (bottom row).

Figure 21B:
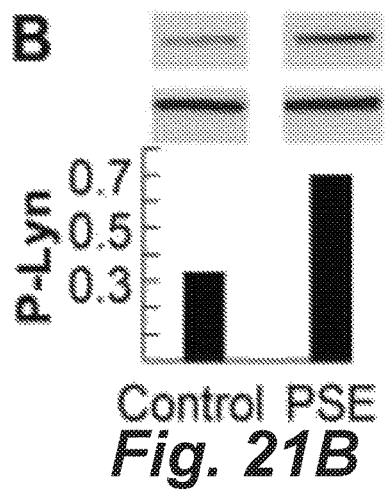

FIG. 21B shows that pLyn increases in hippocampal synaptosome in PSE. Top: representative Western blot from control (n=3) and PSE (n=3).

Figure 21C:
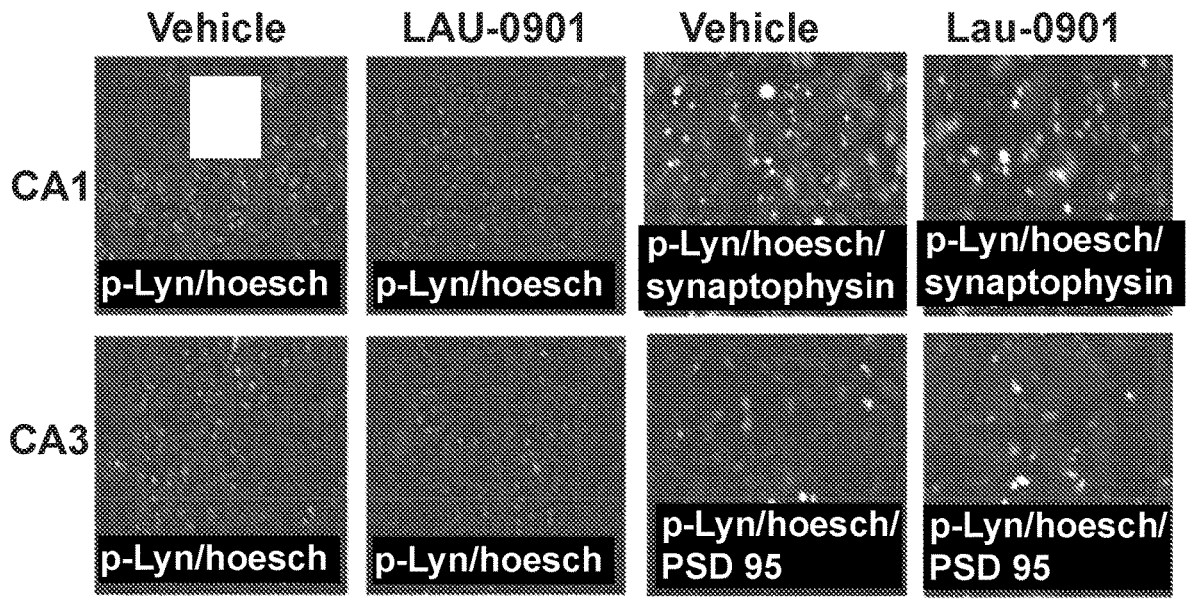

FIG. 21C shows that LAU-0901-treated mice show low puncta phospho-Lyn and its co-localization with pre- and post-synaptic markers (synaptophysin and PSD-95 respectively). Western blot and immunohistology was performed according to established protocols.

Figure 21D:
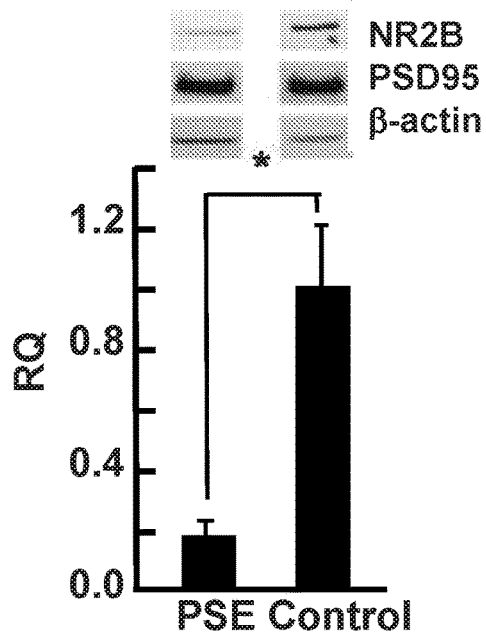

FIG. 21D shows that NR2b decreases in PSE. Data represent average and bars±S.E.M; t-test. *p<0.005

Figure 22:
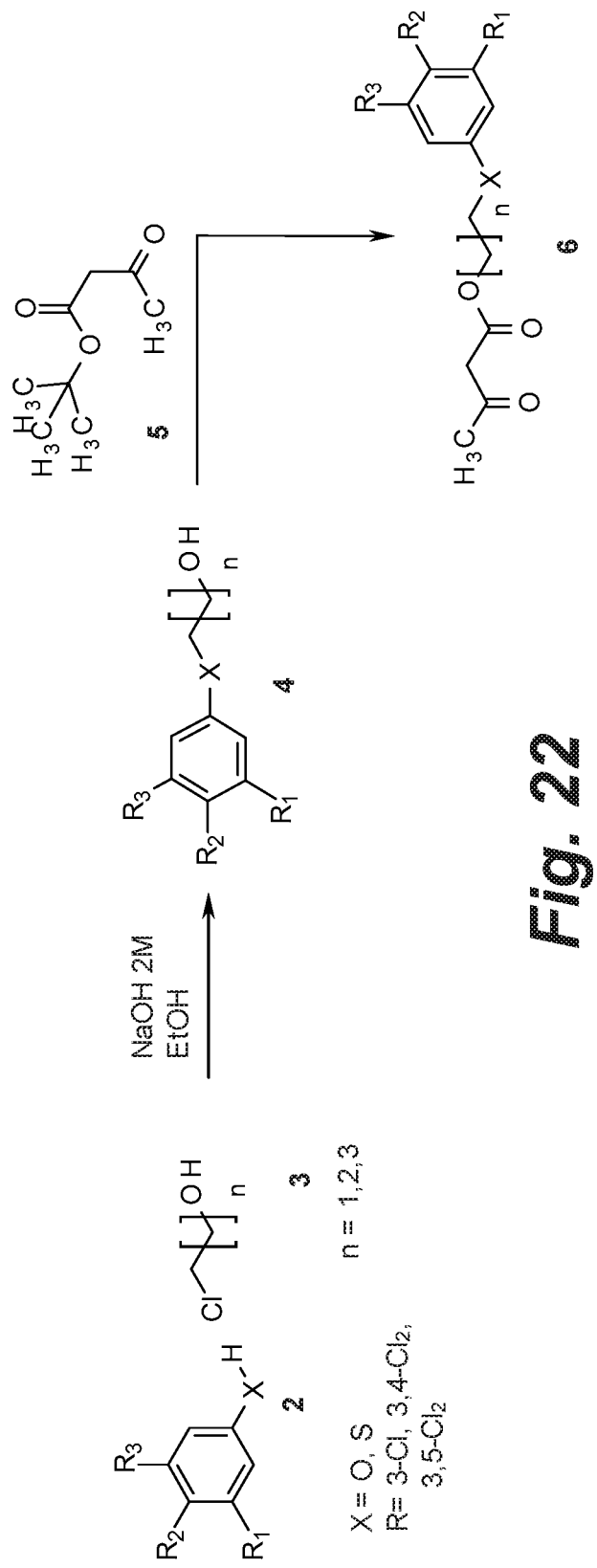

FIG. 22 schematically illustrates synthesis of 3-oxobutyric acid esters 6 (Scheme 1).

Figure 23:
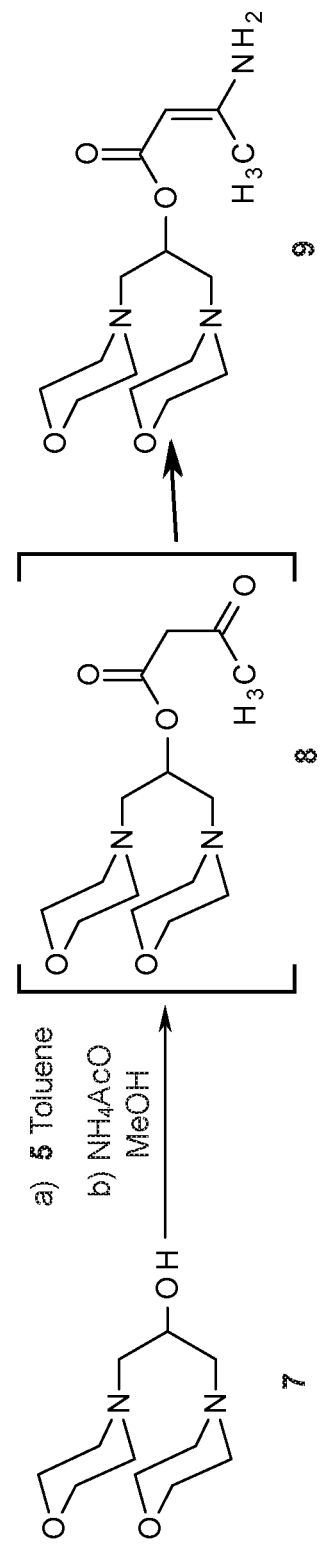

FIG. 23 schematically illustrates the synthesis of 3-amino-2-butenoic acid 1,3-di-(4-morpholinyl)-2-propyl ester 9 (Scheme 2).

Figure 24:
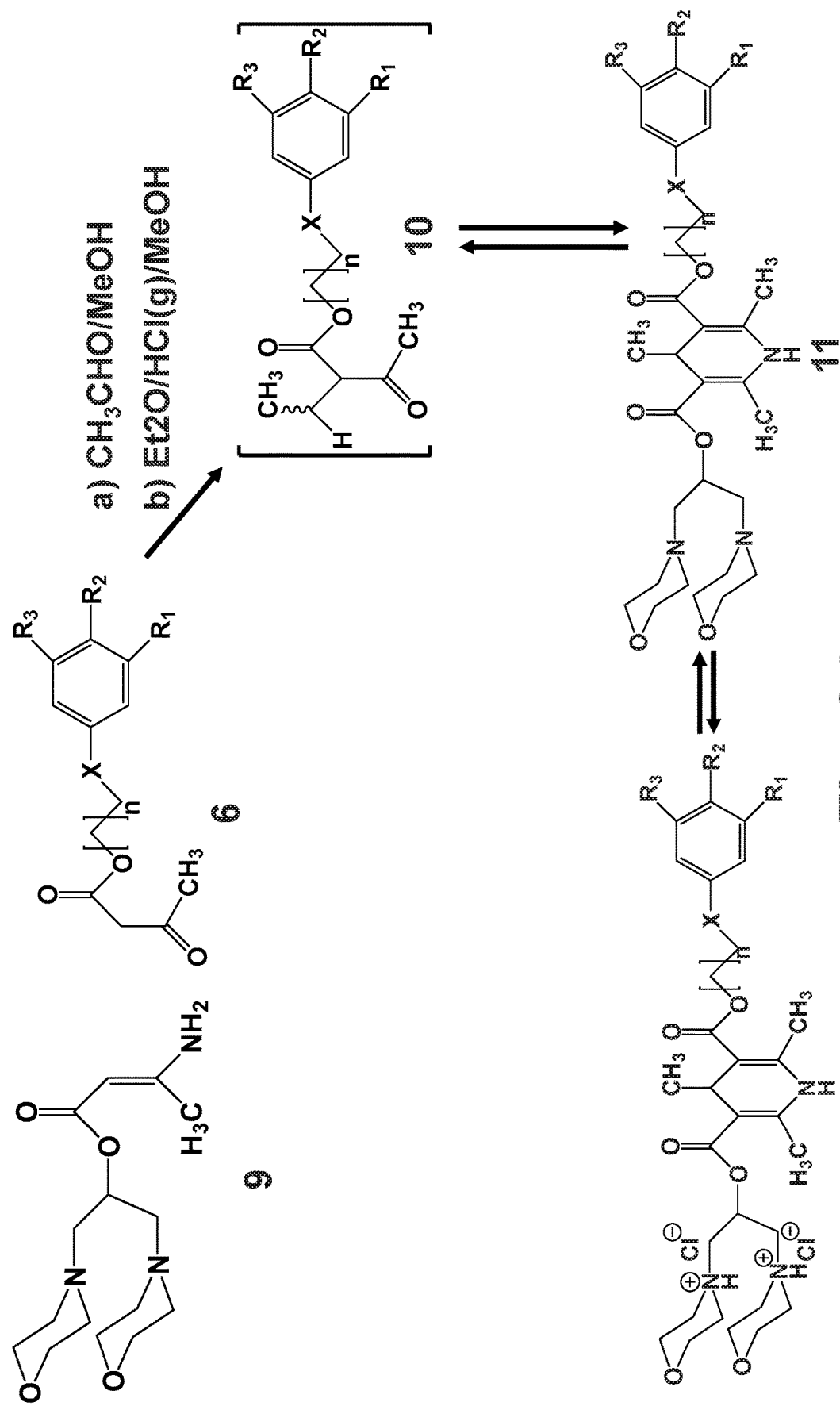

FIG. 24 schematically illustrates the synthesis of 1,4-dihydropyridines 1 (Scheme 3).

Figure 25:
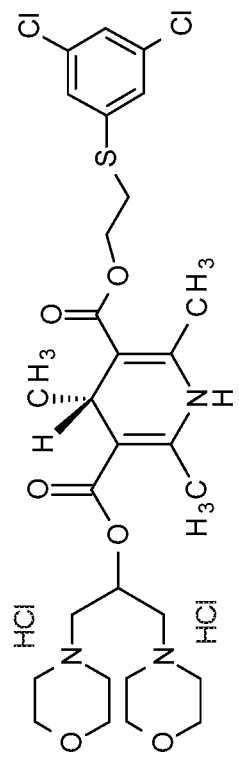
Figure 25:
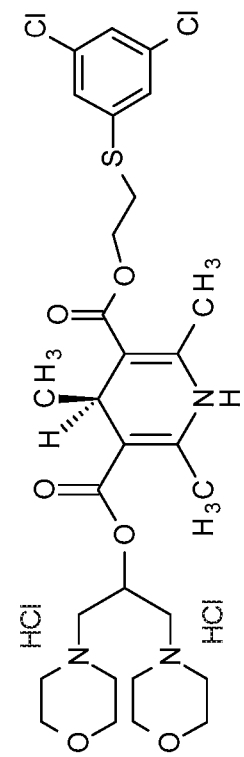

FIG. 25 illustrates the enantiomers of compound LAU-09021.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the advantageous methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, toxicology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated, Abbreviations PAF-r, Platelet-Activating Factor receptor; PAF, Platelet-Activating Factor; GBM, glioblastoma multiforme; PAF-AH, PAF acetylhydrolase; ip, intraperitoneal Definitions The term "Platelet-Activating Factor receptor (PAF-r) as used herein refers to a G-protein coupled receptor that shows structural characteristics of the rhodopsin gene family and binds platelet-activating factor. The PAF receptor and binds platelet-activating factor. PAF is a phospholipid (1-0-alkyl-2-acetyl-sn-glycero-3-phosphorylcholine) that has been implicated as a mediator in diverse pathologic processes, such as allergy, asthma, septic shock, arterial thrombosis, and inflammatory processes.

The term "Platelet-Activating Factor", interchangeably known as PAF, PAF-acether or AGEPC (acetyl-glyceryl-ether-phosphorylcholine), is a potent phospholipid activator and mediator of many leukocyte functions, platelet aggregation and degranulation, inflammation, and anaphylaxis, it is also involved in changes to vascular permeability, the oxidative burst, chemotaxis of leukocytes, as well as augmentation of arachidonic acid metabolism in phagocytes.

PAF is produced by a variety of cells, but especially those involved in host defense, such as platelets, endothelial cells, neutrophils monocytes, and macrophages. PAF is continuously produced by these cells but in tow quantities and production is controlled by the activity of PAF acetylhydrolases (PAF-AH). It is produced in larger quantities by inflammatory cells in response to specific stimuli.

The PAF signaling system can trigger inflammatory and thrombotic cascades, amplify these cascades when acting with other mediators, and mediates molecular and cellular interactions (cross talk) between inflammation and thrombosis. Unregulated PAF signaling can cause pathological inflammation and has been found to be a cause in sepsis, shock, and traumatic injury. PAF can be used as a local signaling molecule and travel over very short distances or it can be circulated throughout the body. PAF also induces apoptosis that is independent of the PAF receptor. The pathway to apoptosis can be inhibited by negative feedback from PAF acetylhydrolase (PAF-AH) that catabolizes platelet-activating factor.

Several molecular species of platelet-activating factor that vary in the length of the O-alkyl side-chain have been identified, its alkyl group is connected by an ether linkage at the C1 carbon to a 16-carbon chain. The acyl group at the C2 carbon is an acetate unit whose short length increases the solubility of PAF allowing it to function as a soluble signal messenger. The C3 has a phosphocholine head group, just like standard phosphatidylcholine.

PAF cannot be modified without losing its biological activity. Thus, small changes in the structure of PAF can render its signaling abilities inert. Platelet and blood pressure response are dependent on the sn-2 propionyl analog. If the sn-1 is removed than PAF lacks biological activity. Finally, at the sn-3 position of PAF as an increasing number of methyl groups are removed sequentially, biological activity diminishes until inactivated.

PAF antagonists are a type of receptor ligand or drug that does not provoke an inflammatory response upon binding, but blocks or lessens the effect of PAF. Examples of PAF antagonists include, but are not limited to, such as CV-3988, a PAF antagonist that blocks signaling events correlated to the expression and binding of PAF to the PAF receptor. SM-12502, a PAF antagonist that is metabolized in the liver by the enzyme CYP2A6, and Rupatadine an antihistamine and PAF antagonist used to treat allergies.

The term "brain tumor" as used herein refers to a "glioma" or primary brain tumor derived from glial support cells, and which is the most common primary tumor of the adult central nervous system resulting in an estimated 13,000 deaths in 2010. Adult gliomas of astrocytic origin (astrocytomas) comprise a spectrum of neoplasms that are generally classified by WHO standards into low-grade benign tumors (i.e. juvenile pilocytic astrocytoma, diffuse astrocytoma) and high-grade malignant tumors (i.e. anaplastic astrocytoma and glioblastoma multiforme (GBM)). Patients diagnosed with grade IV GBM, the most aggressive malignant glioma, have a median survival of 9-12 months after the onset of clinical symptoms. Molecular analyses of glioma specimens have identified several common genetic alterations that may contribute to glioblastoma formation.

The term "Glioblastoma Multiforme (GBM)" as used herein is a glioma or brain tumor derived from glial cells characterized by the presence of small areas of necrotizing tissue that is surrounded by anaplastic cells (pseudopalisading necrosis). This characteristic, as well as the presence of hyperplastic blood vessels, differentiates the tumor from Grade 3 astrocytomas, which do not have these features.

"Highly invasive glioma cells," or "HIGCs," are a subtype (subpopulation) of human GBM cells characterized by an ability to migrate from one brain hemisphere into which the cells are injected into the contralateral hemisphere. An example of an HIGC is the U87R subtype of the U87MG human glioblastoma cells as used experimentally as described, for example, in the present disclosure.

"Brain-tumor initiating cells," or "BTICs," are a subtype (subpopulation) of human GBM cells characterized by their stem-cell like properties of being able to self-renew, generate spheres without the addition of exogenous mitogens and growth factors, and induce tumor formation vivo when placed in the brains of immuno-compromised mice.

In general, gliomas are extremely difficult to treat using conventional approaches. This is primarily due to the intrinsic propensity of glioma cells to exit the tumor core and invade the adjacent normal brain parenchyma. These migrating cells escape surgical resection and are poorly targeted by radiation or chemotherapy. They sometimes travel over long distances, frequently along blood vessel and fiber tracts, and then initiate secondary tumor growth at their final destination. This distinguishing invasive ability is not shared by non-glial cells that metastasize from other primary tumor sites (e.g. breast) to brain tissue. The invasion of glioma cells is likely triggered by a presently undefined signal or signals that promote a cascade of cellular responses, including cell elongation, integrin-mediated cell attachment to extracellular matrix (ECM) molecules, the production and secretion of ECM-degrading enzymes, and cell movement.

The term "pharmaceutically acceptable derivatives" of a PAF-r antagonist compound of the disclosure as used herein refers salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1-yl-methylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl ar heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl ar heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, amelioration of the symptoms of a particular disorder by administration of a particular compound or pharmaceutical composition refers to any lessening, whether permanent or temporary, lasting or transient that can be attributed to or associated with administration of the composition.

The term "therapeutically effective amount" as used herein refers to that amount of an embodiment of the composition or pharmaceutical composition being administered that will relieve to some extent one or more of the symptoms of the disease or condition being treated, and/or that amount that will prevent, to some extent, one or more of the symptoms of the condition or disease that the subject being treated has or is at risk of developing. In an embodiment, therapeutically effective amount refers to an amount needed of a PAF-r antagonist to treat glioblastoma or at least one pathological effect resulting from the presence of a glioblastoma or other cancerous condition in the brain of a subject human or animal.

As used interchangeably herein, "subject," "individual," or "patient," refers to a vertebrate, advantageously a mammal, more advantageously a human. Mammals include, but are not limited to, murines, simians, humans, farm animals, sport animals, and pets. The term "pet" includes a dog, cat, guinea pig, mouse, rat, rabbit, ferret, and the like. The term "farm animal" includes a horse, sheep, goat, chicken, pig, cow, donkey, llama, alpaca, turkey, and the like.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that is useful in preparing a pharmaceutical composition that is generally safe, non-toxic and neither biologically nor otherwise undesirable, and include an excipient, diluent, carrier, and adjuvant that is acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" or a "pharmaceutical formulation" is meant to encompass a composition or pharmaceutical composition suitable for administration to a subject, such as a mammal, especially a human and that refers to the combination of an active agent(s) such as LAU-0901 and the derivatives thereof of the disclosure, or ingredient with a pharmaceutically acceptable carrier or excipient, making the composition suitable for diagnostic, therapeutic, or preventive use in vitro, in vivo, or ex vivo. In general a "pharmaceutical composition" is sterile, and advantageously free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number at different routes of administration including oral, intravenous, buccal, rectal, parenteral, intraperitoneal, intradermal, intratracheal, intramuscular, subcutaneous, inhalational and the like.

The term "administration" refers to introducing a composition of the present disclosure into a subject. One advantageous route of administration of the composition is intravenous administration. However, any route of administration, such as oral, topical, subcutaneous, peritoneal, intra-arterial, inhalation, vaginal, rectal, nasal, introduction into the cerebrospinal fluid, or instillation into body compartments can be used.

As used herein, "treatment" and "treating" refer to the management and care of a subject for the purpose of combating a condition, disease or disorder, in any manner in which one or more of the symptoms of a disease or disorder are ameliorated or otherwise beneficially altered. The term is intended to include the full spectrum of treatments for a given condition from which the patient is suffering, such as administration of the active compound for the purpose of alleviating or relieving symptoms or complications; delaying the progression of the condition, disease or disorder; curing or eliminating the condition, disease or disorder and/or preventing the condition, disease or disorder, wherein "preventing" or "prevention" is to be understood to refer to the management and care of a patient for the purpose of hindering the development of the condition, disease or disorder, and includes the administration of the active compounds to prevent or reduce the risk of the onset of symptoms or complications. The patient to be treated is advantageously a mammal, in particular a human being. Treatment also encompasses any pharmaceutical use of the compositions herein, such as use for treating a disease as provided herein.

The term "unit dosage form," as used herein, refers to physically discrete units suitable as unitary dosages for human and/or animal subjects, each unit containing a predetermined quantity of a compound (e.g., compositions or pharmaceutical compositions, as described herein) calculated in an amount sufficient to produce the desired effect in association with a pharmaceutically acceptable diluent, carrier or vehicle. The term "dosage" as used herein of the compounds according to the disclosure is determined by the physician by means of the patient-specific parameters, such as age, weight, sex, severity of the disease, etc. The dosage is advantageously between 0.001 mg/kg and 1000 mg/kg body weight, more advantageously 0.01 and 500 mg/kg body weight and most advantageously 0.1 and 100 mg/kg body weight.

The terms "sufficient" and "effective", as used interchangeably herein, refer to an amount (e.g., mass, volume, dosage, concentration, and/or time period) needed to achieve one or more desired result(s).

Discussion

Glioblastoma Multiforme (GBM), one of the most invasive brain tumors, is resistant to treatments, which is a major factor underlying tumor recurrence, rapid early infiltration to surrounding tissue, high mortality rates, and recurrent seizures patients. The identification of potential therapeutic agents and of therapeutically targetable mechanisms that can counteract GBM growth and invasiveness is needed. While not wishing to be held to any one hypothesis, it is possible that GBM recurrence and invasiveness is expedited by perturbed neuroinflammatory signaling driven by an enhanced abundance of the phospholipid mediator Platelet-Activating Factor (PAF). As a consequence, tumor growth is enabled. Tumor development, patient quality of life, and morbidity are also affected by disruptions of neuronal networks and the formation of aberrant connections that mediate onset of epileptic seizures.

A mouse model of GBM, in vivo monitoring of tumor growth and invasiveness, as well as neuronal network activities with chronically-implanted multi-array electrodes (silicon probes), cellular and biochemical approaches, synthetic low molecular weight, brain penetrant PAF receptor (PAF-r) antagonists, LC-MS/MS-based lipidomic analysis and a mouse deficient in the PAF receptor (PAF-r) were used to investigate these phenomena. Data shows that a PAF-receptor antagonist remarkably decreases GBM tumor size and pathological consequences from the tumor. Accordingly, a series of PAF-r antagonist structural analogs of LAU-0901 have also now been developed, as shown in FIG. 13, for use as therapeutic agents and for use to define cellular and molecular mechanisms.

It has now been shown that GSM induces PAR-r activation that in turn creates a favorable milieu for tumor invasiveness, PAF-r mediation of neuronal hyper-excitability, PAF-r-mediated signaling triggering the formation of dysmorphic dendritic spines that contribute to aberrant connections, and that PAF-r activity mediating interneuronal damage, facilitating aberrant oscillation activities leading to epileptogenic seizures.

Described herein are compositions, methods and kits for the treatment of glioblastoma and glioblastoma-associated seizures, and glioblastoma-associated epilepsy. Accordingly, antagonism of the PAF-r offers an advantageous target for the modulation of glioblastomal (and other brain tumor cell) proliferation and of glioma-originating pathological conditions such that the antagonists of the disclosure can provide neuroprotection and amelioration of such as seizures. Furthermore, the disclosure provides indications of possible PAR-r antagonist analogs useful as therapeutic agents in subject patients having a glioma and the like.

The disclosure establishes the foundation of a new experimental therapeutic strategy that targets the GBM itself as well key dysregulated and excessive inflammation mediated by PAF-receptor over-activation. The key molecules to be studied are low molecular weight platelet-activating factor (PAF) receptor antagonists that, by reducing the pro-inflammatory environment in an effective and timely manner, promote inflammation resolution. This strategy has the potential to minimize damage to neuron motor circuits and significantly improve patient outcome and recovery.

The outcomes of these studies can lead to a therapeutic paradigm shift by enhancing the intrinsic potential of brain cells to protect and repair themselves by attenuating neuroinflammation cascades while enhancing beneficial homeostatic signaling. These innovative therapeutic concepts and targets proposed to be studied for GSM would also be applicable to other neurodegenerative diseases, which remain among the greatest challenges to public health.

Pharmaceutical Formulations and Routes of Administration

Embodiments of the present disclosure include a composition or pharmaceutical composition as identified herein, as shown in FIG. 13 (including but not limited to LAU-0901) and can be formulated with one or more pharmaceutically acceptable excipients, diluents, carriers and/or adjuvants. In addition, embodiments of the compositions of the present disclosure include a compound, and in particular, but not limited to, the PAR-r antagonist LAU-0901 formulated with one or more pharmaceutically acceptable auxiliary substances.

The compositions or pharmaceutical compositions can be formulated with one or more pharmaceutically acceptable excipients, diluents, carriers, and/or adjuvants to provide an embodiment of a composition of the present disclosure. A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, & Wilkins; and Handbook of Pharmaceutical Excipients (2000) A. H. Kibbe et al., eds., 3rd ed. Amer. Pharmaceutical Assoc.

The compositions or pharmaceutical compositions of the disclosure can be administered to the subject using any means capable of resulting in the desired effect. Thus, the composition or pharmaceutical composition can be incorporated into a variety of formulations for therapeutic administration. For example, the composition or pharmaceutical composition can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections inhalants and aerosols.

In pharmaceutical dosage forms, the composition or pharmaceutical composition may be administered in the form of its pharmaceutically acceptable salts, or a subject active composition may be used alone or in appropriate association, as well as in combination, with other pharmaceutically active compounds.

A reference to a compound of the disclosure and subgroups thereof also includes ionic forms, salts, solvates, isomers, tautomers, esters, prodrugs, isotopes and protected forms thereof, for example, as discussed below; advantageously, the salts or tautomers or isomers or solvates thereof; and more advantageously, the salts or tautomers or solvates thereof.

Many compounds of the formula (i), for example, can exist in the form of salts, for example acid addition salts or, in certain cases salts of organic and inorganic bases such as phenolate, carboxylate, sulphonate and phosphate salts. All such salts are within the scope of this disclosure, and references to compounds of the formula (I) include the salt forms of the compounds.

The salts of the present disclosure can be synthesized from the parent compound that contains a basic or acidic moiety by conventional chemical methods such as methods described in Pharmaceutical Salts: Properties, Selection, and Use. P. Heinrich Stahl (ed), Camille G. Wermuth (ed), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, non-aqueous media such as ether, ethyl acetate, ethanol, isopropanol, or acetonitrile are used.

Acid addition salts may be formed with a wide variety of acids, both inorganic and organic. Examples of acid addition salts include salts formed with an acid selected from the group consisting of acetic, 2,2-dichloroacetic, adipic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), .alpha.-oxoglutaric, glycolic, hippuric, hydrobromic, hydrochloric, hydriodic, isethionic, (+)-L-lactic, (+−)-DL-lactic, lactobionic, maleic, malic, (−)-L-malic, malonic, (+−)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

If the compound is anionic, or has a functional group which may be anionic (e.g., —COOH may be —COO), then a salt may be formed with a suitable Examples Of suitable inorganic cations include, but are not limited to, alkali metal ions such as $Na^+$ and $K^+$, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the disclosure contain an amine function, these may form quaternary ammonium salts, for example by reaction with an alkylating agent according to methods well known to the skilled person. Such quaternary ammonium compounds are within the scope of formula (I).

The salt forms of the compounds of the disclosure are typically pharmaceutically acceptable salts, and examples of pharmaceutically acceptable salts are discussed in Berge et al., 1977, "Pharmaceutically Acceptable Salts." J. Pharm. Sci., Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the disclosure, also foal part of the disclosure.

For oral preparations, the composition or pharmaceutical composition can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the composition or pharmaceutical composition can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the composition or pharmaceutical composition can be utilized in aerosol formulation to be administered via inhalation. Embodiments of the composition or pharmaceutical composition can be formulated into pressurized acceptable propellants such as dichlorodifluoromethane, propane, nitrogen and the like.

Unit dosage forms for oral administration, such as syrups, elixirs, and suspensions, may be provided wherein each dosage unit, for example, teaspoonful, tablespoonful, tablet or suppository, contains a predetermined amount of the composition containing one or more compositions. Similarly, unit dosage forms for injection or intravenous administration may comprise the composition or pharmaceutical composition in a composition as a solution in sterile water, normal saline or another pharmaceutically acceptable carrier.

Embodiments of the composition or pharmaceutical composition can be formulated in an injectable composition in accordance with the disclosure. Typically, injectable compositions are prepared as liquid solutions or suspensions; solid forms suitable for solution in, or suspension in, liquid vehicles prior to injection may also be prepared. The preparation may also be emulsified or the active ingredient (triamino-pyridine derivative and/or the labeled triamino-pyridine derivative) encapsulated in liposome vehicles in accordance with the present disclosure.

In an embodiment, the composition or pharmaceutical composition can be formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,620,589; 5,643,207; 6,198,966; and the like. In general, delivery of the composition or pharmaceutical composition can be accomplished using any of a variety of refillable, pump systems. Pumps provide consistent, controlled release over time. In some embodiments, the composition or pharmaceutical composition can be in a liquid formulation in a drug impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, in the brain ventricles, transnasally, or any other route to access directly the brain parenchyma, tumor or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,652, and the like. In general, a subject treatment method can be accomplished using any of a variety of refillable, non-exchangeable pump systems. Pumps and other convective systems are generally advantageous due to their generally more consistent, controlled release over time. Osmotic pumps are used in some embodiments due to their combined advantages of more consistent controlled release and relatively small size (See, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916, 899; 3,923,426; 3,987,790; 3,995,631; 3,916,899; 4,016, 880; 4,036,228; 4,111,202; 4,111,203; 4,203,440; 4,203, 442; 4,210,139; 4,327,725; 4,627,850; 4,865,845; 5,057, 318; 5,059,423; 5,112,614; 5,137,727; 5,234,692; 5,234, 693; 5,728,396; and the like.

Suitable excipient vehicles for the composition or pharmaceutical composition are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pennsylvania, 17th edition, 1985. The composition or formulation to be administered will, in any event, contain a quantity of the composition or pharmaceutical composition adequate to achieve the desired state in the subject being treated.

Compositions of the present disclosure can include those that comprise a sustained release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix. In another embodiment, the pharmaceutical composition of the present disclosure (as well as combination compositions) can be delivered in a controlled release system. For example, the composition or pharmaceutical composition may be administered using intravenous infusion, an implantable osmotic pump, a transdermal patch, liposomes, or other modes of administration. In one embodiment, a pump may be used (Sefton (1987). CRC Crit. Ref. Biomed. Eng. 14;201; Buchwald et al. (1980). Surgery 88:507; Saudek et al. (1989), N. Engl. J. Med. 321;574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). Science 249:1527-1533.

In another embodiment, the compositions of the present disclosure (as well as combination compositions separately or together) include those formed by impregnation of the composition or pharmaceutical composition described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

In another embodiment, the compositions or pharmaceutical compositions of the present disclosure (as well as combination compositions separately or together), in particular LAU-09021, can be part of a delayed-release formulation such as a delayed-release PAF-r antagonist formulation. Delayed-release dosage formulations can be prepared as described in standard references such as "Pharmaceutical dosage form tablets", eds. Liberman et al. (New York, Marcel Dekker, Inc., 1989). "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media et al., 1995).

Delayed-release formulations can be created by coating a solid dosage (e.g., cannabinoid) form with a polymer film, which is insoluble in the acidic environment of the stomach, and soluble in the neutral environment of the small intestine. pH-dependent polymers are frequently used to delay release, for example following ingestion, until the composition has passed through the low pH of the stomach and entered into the higher pH of the small intestine. Representative pH dependent polymer include, but not limited to, methylacrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylatemethacrylic acid copolymers, sodium alginate and stearic acid.

The delayed release dosage units can be prepared, for example, by coating a drug (e.g., LAU-0901) or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Advantageous coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon.

Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, advantageously formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH7.0 and above, as a result of a higher degree of esterification), and Eudragit® NE, RL and RS (water-insoluble polymers having different degrees of permeability and expandability): vinyl polymers and copolymers such as polyvinyl pyrrolidone, vinyl acetate, vinylacetate phthalate, vinylacetate crotonic acid copolymer, and ethylene vinyl acetate copolymer; enzymatically degradable polymers such as azo polymers, pectin, chitosan, amylase and guar gum; zein and shellac.

Combinations of different coating materials may also be used. Multilayer coatings using different polymers may also be applied.

The advantageous coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies. The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is advantageously used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Dosages

Embodiments of the composition or pharmaceutical composition can be administered to a subject in one or more doses. Those of skill will readily appreciate that dose levels can vary as a function of the specific composition or pharmaceutical composition administered, the severity of the symptoms and the susceptibility of the subject to side effects. Advantageous dosages for a given compound are readily determinable by those of skill in the art by a variety of means.

In an embodiment, multiple doses of the composition or pharmaceutical composition are administered. The frequency of administration of the composition or pharmaceutical composition can vary depending on any of a variety of factors, e.g., severity of the symptoms, and the like. For example, in an embodiment, the composition or pharmaceutical composition can be administered once per month, twice per month, three times per month, every other week (qow), once per week (qw), twice per week, (biw), three times per week (tiw), four times per week, live times per week, six times per week, every other day (qod), daily (qd), twice a day (qid), three times a day (tid), or four times a day. As discussed above, in an embodiment, the composition or pharmaceutical composition is administered 1 to 4 times a day over a 1 to 10 day time period.

The duration of administration of the composition or pharmaceutical composition analogue, e.g., the period of time over which the composition or pharmaceutical composition is administered, can vary, depending on any of a variety of factors, e.g., patient response, etc. For example, the composition or pharmaceutical composition in combination or separately, can be administered over a period of time of about one day to one week, about one day to two weeks. The amount of the PAF antagonist and pharmaceutical compositions of the present disclosure that can be effective in treating the condition or disease can be determined by standard clinical techniques. In addition, in vitro or in vivo assays can optionally be employed to help identify optimal dosage ranges. The precise dose to be employed can also depend on the route of administration, and can be decided according to the judgment of the practitioner and each patient's circumstances.

Routes of Administration

The therapeutic compositions of the disclosure provide methods and compo salons for the administration of the active agent(s) (e.g., as PAF-r antagonist such as LAU-0901 or derivatives thereof such as shown, but not limited to, those of FIG. 13) to a subject (e.g., a human) using any available method and route suitable for drug delivery, including in vivo in vitro and ex vivo methods, as well as systemic and localized routes of administration. Routes of administration include intranasal, intramuscular, intratracheal, subcutaneous, intra cerebroventricular, intradermal, topical application, intravenous, rectal, nasal, oral, and other enteral and parenteral routes of administration. Routes of administration may be combined, if desired, or adjusted depending upon the agent and/or the desired effect. An active agent (e.g. LAU-0901) can be administered in a single dose or in multiple doses.

Embodiments of the composition or pharmaceutical composition can be administered to a subject using available conventional methods and routes suitable for delivery of conventional drugs, including systemic or localized routes. In general, routes of administration contemplated by the disclosure include, but are not limited to, enteral, parenteral, or inhalational routes.

Other compositions, compounds, methods, features, and advantages of the present disclosure will be or become apparent to one having ordinary skill in the art upon examination of the following drawings, detailed description, and examples, it is intended that all such additional compositions, compounds, methods, features, and advantages be included within this description, and be within the scope of the present disclosure.

PAF-r Antagonists

A PAF-r antagonist compound termed LAU-09021, 2,4,6-trimethyl-1,4-dihidropyridine derivative, and having the structure below is described herein.

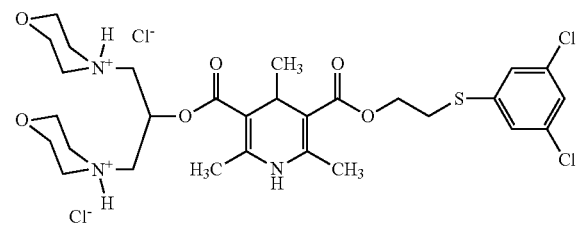

LAU 09021

Techniques as microwaves or parallel synthesis allow the preparation of a series of to optimize the activity of the products in relation with glioblastoma treatment.

The compounds of the disclosure may typically be, but not exclusively, racemic mixtures such as a 50% of S-LAU-09021 and another 50% of R-LAU-09021 as indicated in the scheme 4, although it is contemplated that the chiral resolution and separation of R- and S-enantiomers of the compounds of the disclosure such as shown in FIG. 13 may be isolated by methods we known in the art.

The PAF-r antagonists as described herein can be a part of a therapeutic kit. The kit can comprise at least one vessel containing a PAF-antagonist, and instructions for the preparation of a pharmaceutically acceptable composition of the PAF-antagonist, and can further comprise at least one additional vessel containing a second agent. The second agent can be a pharmaceutically acceptable carrier, for example, or can be a known therapeutic agent for glioblastoma.

Treating a Brain Tumor (Including a Glioblastoma, Astrocytomas, Oligodendroglioma, Ependymal Tumors Neuronal and Glial Mixed Tumors and the Like) in a Subject GSM recurrence and invasiveness is expedited by perturbed neuroinflammatory signaling driven by enhanced abundance of the phospholipid mediator platelet activating factor (PAF) and other docosanoid mediators. Described herein are methods for treating glioblastoma in a subject, and methods of reducing or inhibiting the invasiveness of a glioblastoma. Generally, the method is administering a therapeutically effective amount of a PAF-antagonist to a subject diagnosed with glioblastoma. In addition to treating glioblastoma, PAF-r antagonism can prevent glioblastoma invasiveness and recurrence, and limit glioblastoma-associated phenotypes such as recurrent seizures. In certain embodiments, the PAF-r antagonist can be part of a pharmaceutical formulation as described herein. In one advantageous embodiment, the PAF-r antagonist can be LAU-0901.

Accordingly, one aspect of the disclosure encompasses embodiments of a composition comprising at least one compound having the formula I, or a pharmaceutically acceptable salt thereof:

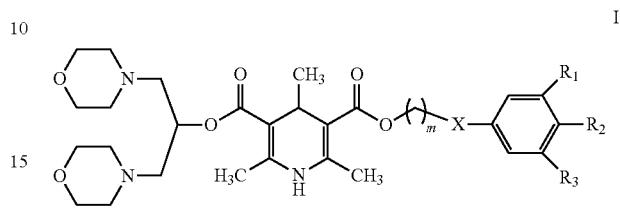

I wherein: m is 1-4, X is O or S. $R_1$ and $R_3$ are independently H or Cl, $R_2$ is H, butoxy, or Cl, and wherein, when: $R_2$ is butoxy, m is 1 or 4, and when $R_1$ and $R_2$ are both Cl, and X is O, m is 3 or 4.

In some embodiments of this aspect of the disclosure, the at least one compound having the formula I can be selected from the group consisting of:

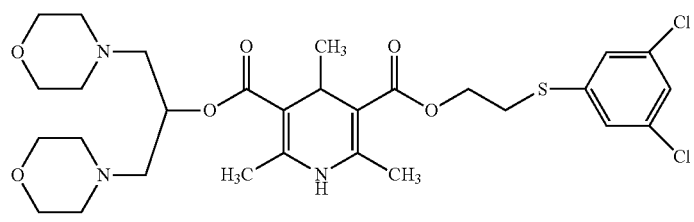

LAU-09015

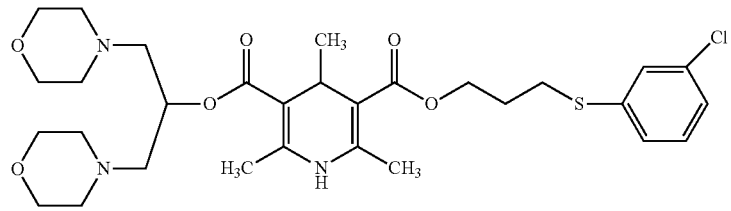

LAU-09018

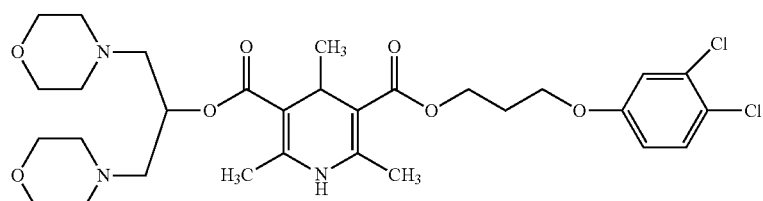

LAU-09019

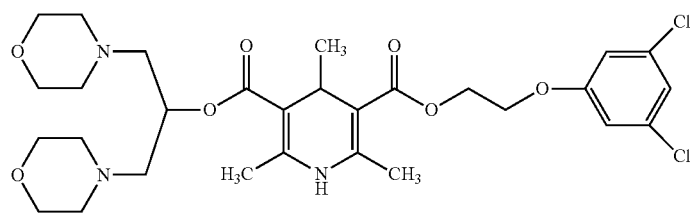

LAU-09020

-continued

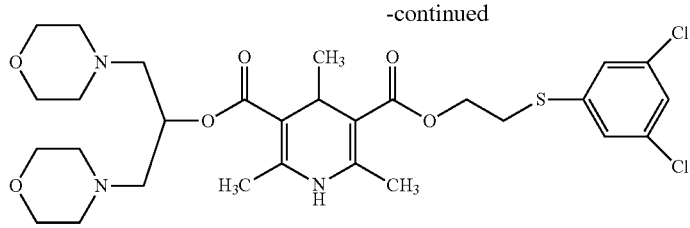

LAU-09021

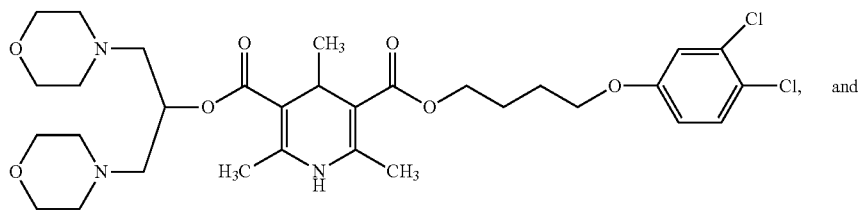

LAU-09023

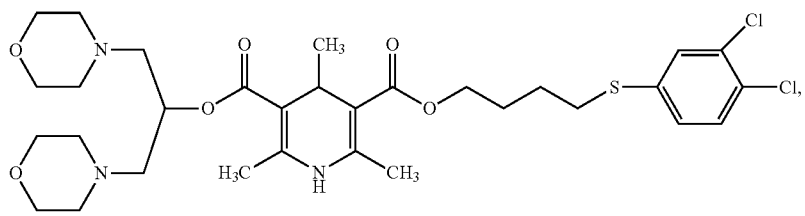

LAU-09025 or a pharmaceutically acceptable salt of any thereof.

In some embodiments of this aspect of the disclosure, the compound can be an R-enantiomer, an S-enantiomer, or a combination thereof.

In some embodiments of this aspect of the disclosure, the compound or the pharmaceutically acceptable salt thereof can be in an amount effective to it the growth of a brain tumor or modulate a neurological activity induced by a brain tumor by antagonizing platelet-activating factor, and the composition further comprises a pharmaceutically acceptable carrier.

In some embodiments of this aspect of the disclosure, the brain tumor can be selected from the group consisting of: a glioblastoma, an astrocytoma, an oligodendroglioma, an ependymal tumor, a neuronal tumor and a combination of glial tumors.

In some embodiments of this aspect of the disclosure, the pharmaceutically acceptable salt can be an acid addition salt.

Another aspect of the disclosure encompasses embodiments of a method for treating or inhibiting a brain tumor or a pathological effect thereof, in a subject, the method comprising the steps: (a) selecting a subject in need of treatment, wherein the subject has been diagnosed with a brain tumor or a pathological effect of a brain tumor; and (b) administering a therapeutic composition comprising a therapeutically effective amount of a platelet-activating factor (PAF) receptor antagonist and a pharmaceutically acceptable carrier, wherein the PAF receptor antagonist is according to formula I, or a pharmaceutically acceptable salt thereof:

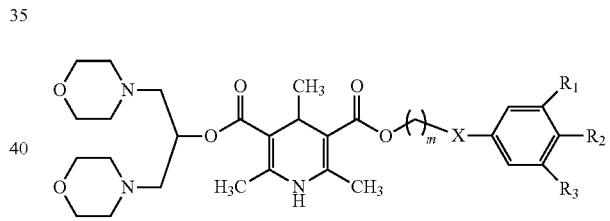

wherein: m is 1-4, X is O or S. $R_1$ and $R_3$ are independently H or Cl, $R_2$ is H, butoxy, or Cl, and wherein, when: $R_2$ is butoxy, m is 1 or 4, and when $R_1$ and $R_2$ are both Cl, and X is O, m is 3 or 4.

In some embodiments of this aspect of the disclosure, the brain tumor can be a selected from the group consisting of: a glioblastoma, an astrocytoma, an oligodendroglioma, an ependymal tumor, a neuronal tumor and a combination of glial tumors.

In some embodiments of this aspect of the disclosure, the pharmaceutically acceptable salt is an acid addition salt.

In some embodiments of this aspect of the disclosure, the compound having the formula I can be selected from the group consisting of:

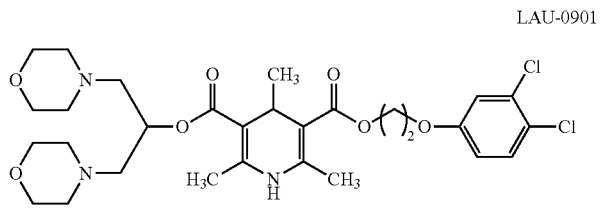

LAU-0901

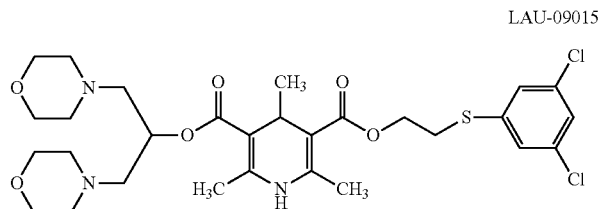

LAU-09015

-continued

LAU-09017
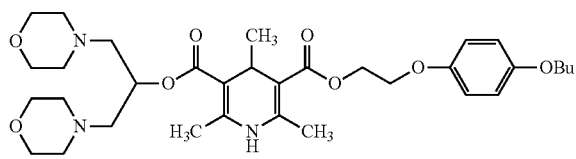

LAU-09018
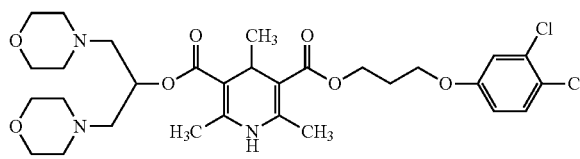

LAU-09019
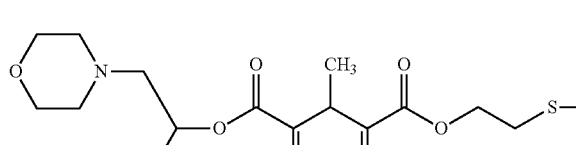

LAU-09020
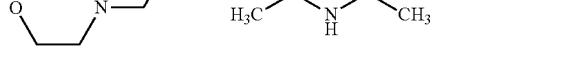

LAU-09021
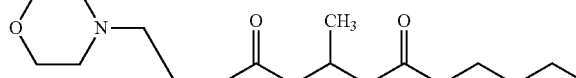

LAU-09023
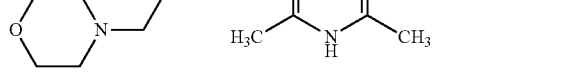

and

LAU-09025
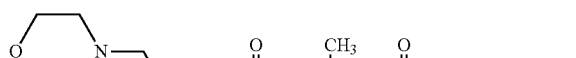

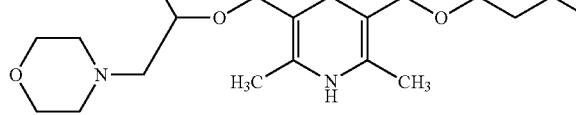

In some embodiments of this aspect of the disclosure, the compound having the formula I is a pharmaceutically acceptable salt of 2,4,6-trimethyl-1,4-dihydro-pyridine-3,5-dicarboxylic acid 5-[2-(3,4-dichlorophenyl) sulfanethyl ester 3-[1,3-di-(4-morpholinyl)-2-propyl-1-ester (LAU-0901) and having the formula:

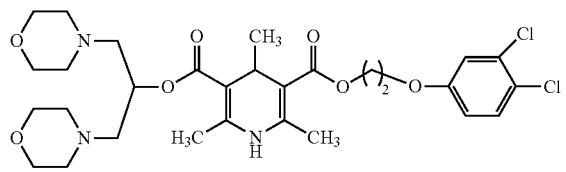

LAU-0901

In some embodiments of this aspect of the disclosure, the therapeutic composition is formulated with an amount of the PAF receptor antagonist effective in reducing or inhibiting a pathological neurological condition associated with a brain tumor in a subject.

In some embodiments of this aspect of the disclosure, the therapeutic composition can be formulated with an amount of the PAF receptor antagonist effective in reducing or inhibiting a seizure associated with glioblastoma in a subject.

Yet another aspect of the disclosure encompasses embodiments of a kit comprising a first vessel containing a platelet-activating factor receptor antagonist compound according to the disclosure, optionally a second vessel containing a pharmaceutically acceptable carrier, and instructions for the preparation of a pharmaceutically acceptable composition comprising an amount of the compound known to antagonize platelet-activating factor receptor that is therapeutically effective in treating a brain tumor or a pathological effect of said brain tumor when administered to a subject.

In some embodiments of this aspect of the disclosure, the brain tumor can be a glioblastoma.

In some embodiments of this aspect of the disclosure, the compound known to antagonize platelet-activating factor receptor can be LAU-09021.

Yet another aspect of this disclosure encompasses embodiments of a kit comprising a first vessel containing a platelet-activating factor receptor antagonist compound according to any of embodiments of this disclosure, optionally a second vessel containing a pharmaceutically acceptable carrier, and instructions for the preparation of a pharmaceutically acceptable composition comprising an amount of the compound known to antagonize platelet-activating factor receptor that is therapeutically effective in treating glioblastoma or a pathological effect of said glioblastoma when administered to a subject.

In some embodiments of this aspect of the disclosure the compound known to antagonize platelet-activating factor receptor is LAU-09021.

It should be emphasized that the embodiments of the present disclosure are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Synthesis of 3-oxo-butyric acid esters 6: In the scheme, as shown in FIG. 22, the synthesis of 3-oxo-butyric acid esters 6 is described, through the preparation of the alcohols 4. In the last step of the scheme, treatment of 4, with the 3-oxo-butyric acid t-butyl ester 5 by heating, allows obtaining of the intermediate 6.

Example 2

Synthesis of 3-amino-2-butenoic acid 1,3-di-(4-morpholinyl)-2-propyl ester 9: Scheme 2, shown in FIG. 23, describes the preparation of the other component of the final product, the enamine 9, using the functionalized alcohol 7, and the t-butyl ester 5. Thermal treatment allows the isolation of the ester 8, and the treatment with ammonia generates the enamine 9.

Example 3

Synthesis of 1,4-dihydropyridines 1: The final step is indicated in the Scheme 3 shown in FIG. 24, where the two components, 9 and the corresponding 6, are treated with acetaldehyde in ethanol, generating initially—with a typical Hanzsch process to generate 1,4-dihydropyridines—a Michael substrate 10, which reacts with 9, to produce the dihydropyridine 11. Finally, treatment with HCl produces the dihydrochloride 1, as the final product.

The above indicated schemes of Examples 1-3 show the preparation of the product LAU-09021 but the same schemes can be used to obtain other analogs such as those shown in FIG. 13 with variations in the positions indicated as X, $R_1$, $R_2$, and $R_3$, and the number n of the methylene groups in the aryl side of the molecule.

Enantiomers of LAU-09021 are shown in FIG. 25

Example 4

GBM-induced PAF accumulation is a result of decrease of PAF-AH activity and promotes GBM invasiveness: GBM induces neuroinflammation that mediates PAF accumulation by limiting PAF-acetyl hydrolase, contributing to a) increased metalloproteinases and chemokine signaling that mediate tumor invasiveness, and b) docosanoid mediators that contribute to proliferation of GBM. PAF concentration increases in cancer and brain tumors (Akai et al., 2002; Hiroshima et al., 1998; Kuruvilla et al., 1994; Li et al., 2008). The PAF-induced neuronal toxicity is mainly characterized by increased levels of PAF due to downregulation of PAF catabolic pathway (Yost et al., 2010: Goracci et al., 2009).

PAF is synthetized from phospholipase A2 (PLA2) enzyme and subsequent elevation of intracellular calcium ions (Aihara et al., 2001, especially after severe seizures (Musto and Samii, 2011), PAF acetylhydrolase (PAF-AH) catabolizes PAF by synthetizing lyso-PAF and then terminates PAF signaling (Bazan, 2005). Also, inflammation stimulates production of PAF (Lacerda-Queiroz et al., 2012; Mazereeuw et al., 2014; Teather et al., 2006: Vlachogianni et al., 2013). An alteration in the endogenous PAF-AH production exacerbates inflammation; administration of exogenous PAF-AH reduces inflammatory injury and mortality (Gomes et al., 2006).

PAF exacerbates invasiveness and dysfunction of the neuronal network by decreasing PAF-AH activity. PAF-AH administration limits GBM invasiveness and aberrant neuronal activities reducing PAF concentration. PAF-AH is expressed in astrocytes, as compared with GBM cells, microglia and neurons. Increase of PAF, PGE, LTB4 and MMP's is correlated with GBM cell migration. Thus, dysfunction of PAF-AH contributes to PAF accumulation and probably that de-regulation of PAF-PAF-AH is a predictor of GBM invasiveness.

Example 5

Figure 7:
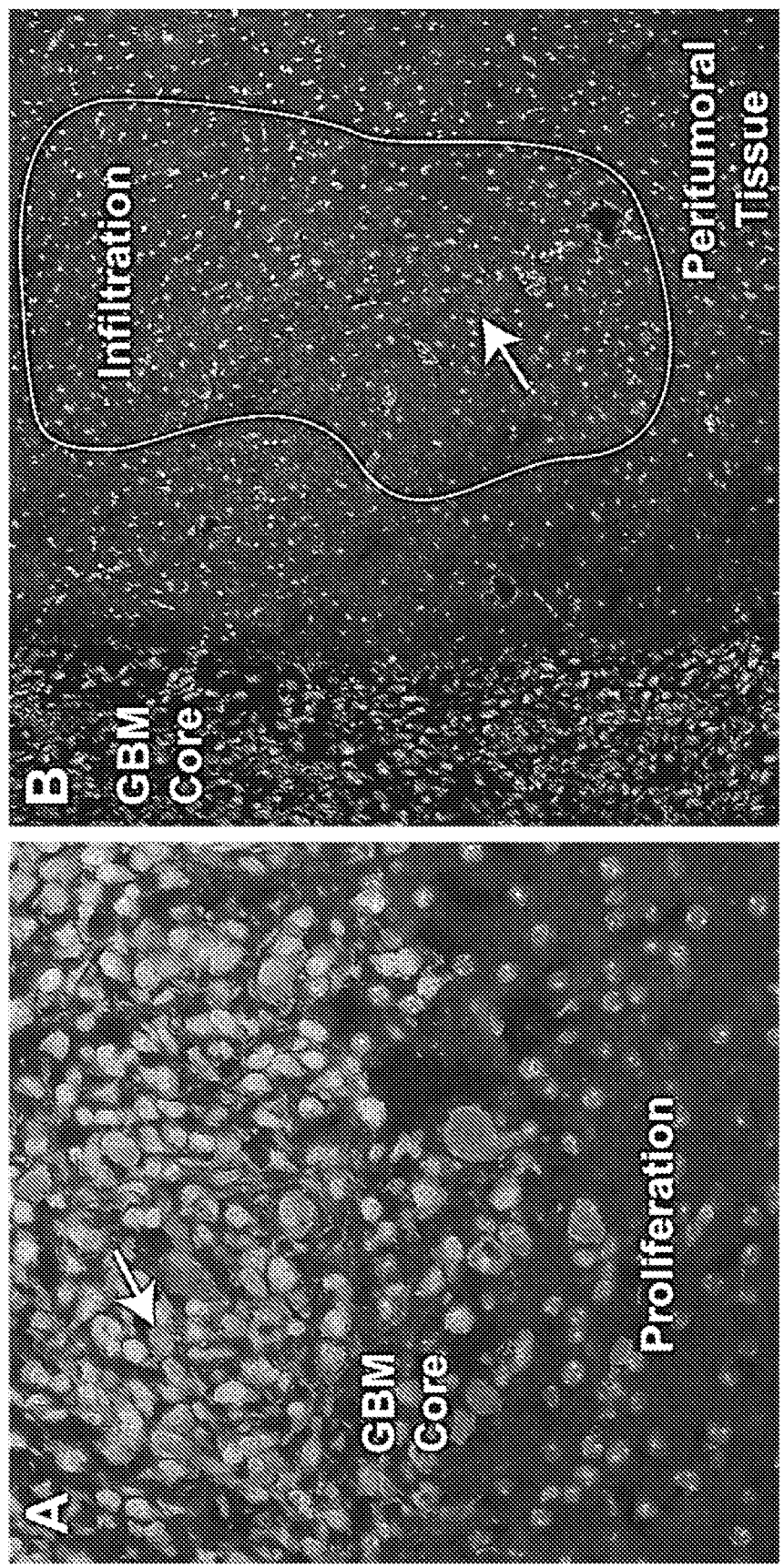
FIG. 7 illustrates that GBM cells infiltrate into a neuronal network. Coronal sections of GBM core show GBM cells stained with vimentin in peritumoral tissue.
Figure 8:
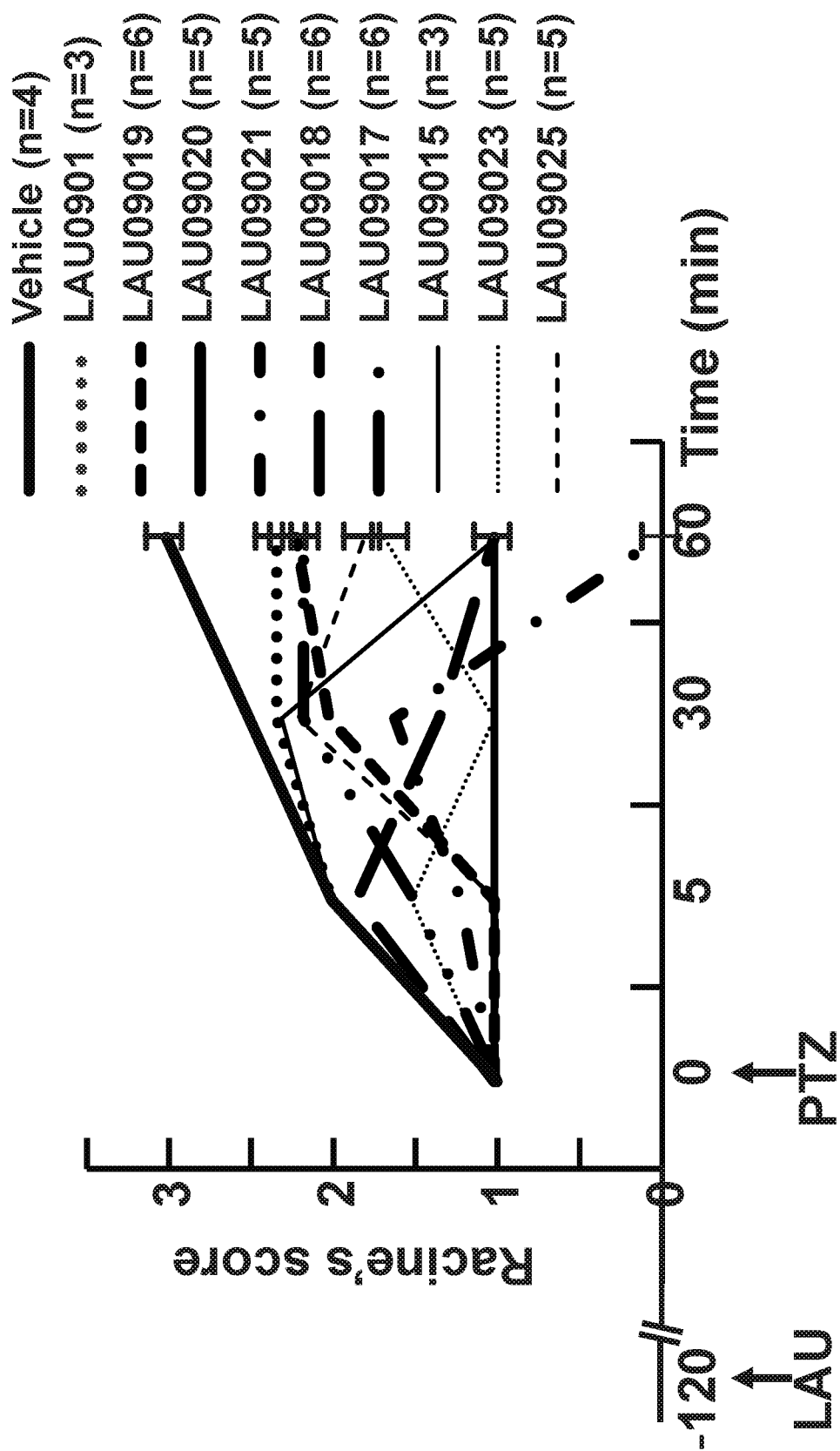
FIG. 8 is a graph illustrating that PAF-r antagonists of the disclosure counteract neuronal hyper-excitability. A single dose (i.p.) of a LAU compound 60 mg/kg; ip.) or vehicle (0.1 mL of sterile 0.9% sodium chloride) was administered 2 h before a single dose of pentylenetetrazol (PTZ) (40 mg/kg; i.p.). Data represent average and bars±S.E.M. t-test between vehicle and for each LAU compound: LAU0901 $p<0.031$; others: $p<0.0001$ at 60 mins. Maximum seizure levels and the percentage reduction from vehicle after PTZ injection are shown. Locomotor seizures were video recorded and quantified according to a modified Racine's score (Stage: 0 normal locomotor activity. Stage 1, behavioral arrest, Stage 2: head nodding; stage 3, facial movements and contralateral forelimb dorms).

GBM activates microglia cells, promoting migration of GSM cells into neuronal network mediated by chemokine MIP-2: Microglia, activated in the surrounding of brain tumors (da Fonseca & Badie, 2013), contribute to tumor progression and metastasis (Ehtesham et al., 2013; Hattermann et al., 2013; Liu et al., 2013, Munson et al., 2013, Najbauer et al., 2012). PAF alters local cytokine networks (Denizot et al., 2005). It is now found that GBM cells can be in the intrahippocampal circuitry (FIGS. 7 and 19).

The PAF-r antagonist LAU0901 reduces microglia activation (Musto and Samii, 2011). Chemokine (C-X-C motif) ligand (MIP-2) enhances local inflammatory responses (Souza et al., 2004) in the brain (Otto et al., 2000; Zwijnenburg et al., 2003). It has been found that MIP-2 in epileptic hippocampal tissue is limited by the PAF-r antagonist LAU-0901 (FIG. 20).

Example 6

PAF-r antagonism limits disruption of extracellular matrix and, as a consequence, reduces GBM invasiveness: MIP-2 mediates GBM invasiveness, increases of MIP-2 are higher in those mice treated with vehicle compared with repertaxin, minocycline and the PAF-r antagonist. Up-regulation of chemokine such as Fibroblast Growth Factor 9 (FGF-9), GCP2, Granulocyte Chemotactic Protein-2 (GCR-2), VCAM-1Monocyte Chemotactic Protein-5 (MCP-5/CCL-12) Vascular Cell Adhesion Molecule-1 (VCAM-1) is present in peritumoral tissue, PAF and PGE2. Elevation of PAF concentration activates microglia cells through PAF-r activity in the peritumoral region compared with GBM core. MIP-2 facilitates GBM invasion to neuronal networks.

An increase of matrix metalloproteinases (MMP), proteolytic enzymes that degrade extracellular matrix (ECM), exacerbate GBM infiltration (Costa et al., 2014; Arcone, 2014; Kim et al., 2014) mediated by microglia cell activation (Hu et al., 2015). PAF enhances production of MPP (Kim et al. 2013; Ottino & Bazan, 2001) and is inhibited by PAF-r antagonism (He, et al., 2006; Bazan and Tao, 1997).

PAF-r antagonism limits MMP activation in GBM and reduce invasiveness, especially MMP-2 and -9, which are capable of cleaving type IV basement membrane collagen (Zucker & Cao, 2009). Accordingly, PAF-r activation mediates infiltration into the peritumoral tissue.

Example 7

GBM induces PAR-r activation that mediates tumor invasiveness, promoting disruptions of neuronal networks due to formation of aberrant neuronal connections: The mechanism that mediates the relation between GBM and post-synaptic terminals needed to be elucidated to understand GBM invasiveness into neuronal networks (FIGS. 5, 6A-6D, and 16). Most of the components of the local field potentials (FIGS. 5 and 6A-6D) arise from post-synaptic terminals (Buzsaki, 2010; Musto et al., 2015) located in dendritic spines (Yuste & Urban, 2004). Lyn increases in synaptic terminals in epilepsy, and it was considered that it mediates aberrant spine formation. Also, these formations are attenuated by PAF-r antagonism (FIG. 21).

Pro-inflammatory mediators enhanced the activity and the expression levels of ASICs. However, it was not clear if PAF-r mediates that expression (Kweon & Suh, 2013). It was seen that in the model of epileptogenesis, ASIC-1 increases in synaptic terminals (FIG. 18) and both ASIC-1 and ASIC-2 increase in the peritumoral area, as compared with tumoral or control tissue (FIG. 17). GBM invasiveness is associated with aberrant neuronal projections (FIGS. 12A-12C and 19).

It is expected that PAF-r activation mediates a high number of infiltrated GBM cells in dendrites, promoting aberrant spinogenesis. PAF-r antagonism limits formation of aberrant dendrites.

Thus micro-epileptiform activity arises distally from GBM beginning four days following GBM cell implantation. An increase of inter-ictal spikes in the CA1, followed by repetitive micro-epileptiform events that will be synchronized with the DG-CA3 network. In addition, increase of hyperexcitability following GBM implantation is expected. Thus aberrant formation of neuronal networks in peritumoral tissue, is susceptible to seizures is mediated by PAF-r activity and that will be attenuated by PAF-r antagonist such as LAU-0901 and the like.

Example 8

Ablation of the PAF-r (PAF-r antagonism) prevents GBM invasiveness and, as a consequence, limits recurrent seizures: The PAF-r antagonist limits seizure susceptibility (Musto et al., 2011). It was observed that PAF-r antagonism limits formation of aberrant neuronal projections (FIGS. 12A-12C and 20).

LAU-0901 administration likely reduces invasiveness, improving neurological outcomes, and reduce propagation and the recurrence of seizures. PAF-r antagonism will be effective to reduce seizures: accordingly, PAF-r antagonism will reduce invasiveness of GBM and, as a consequence, reduce epileptic seizures.

Example 9

Glioblastoma multiforme (GBM) Invasiveness and recurrent seizures. Patients with GBM and seizures can be treated with antiepileptic drugs (Rosati et. al., 2009), however it is not clear yet if recurrent seizures exacerbate GBM grow and invasiveness. Repetitive seizures accelerate GBM invasiveness mediated by the presence of PAF-r. This observation will indicate that anti-epileptic drugs should also include anti-GBM therapies immediately after GBM diagnosis, in order to prevent invasiveness, improving survival rate and quality of life in patients with GBM.

Figure 1:
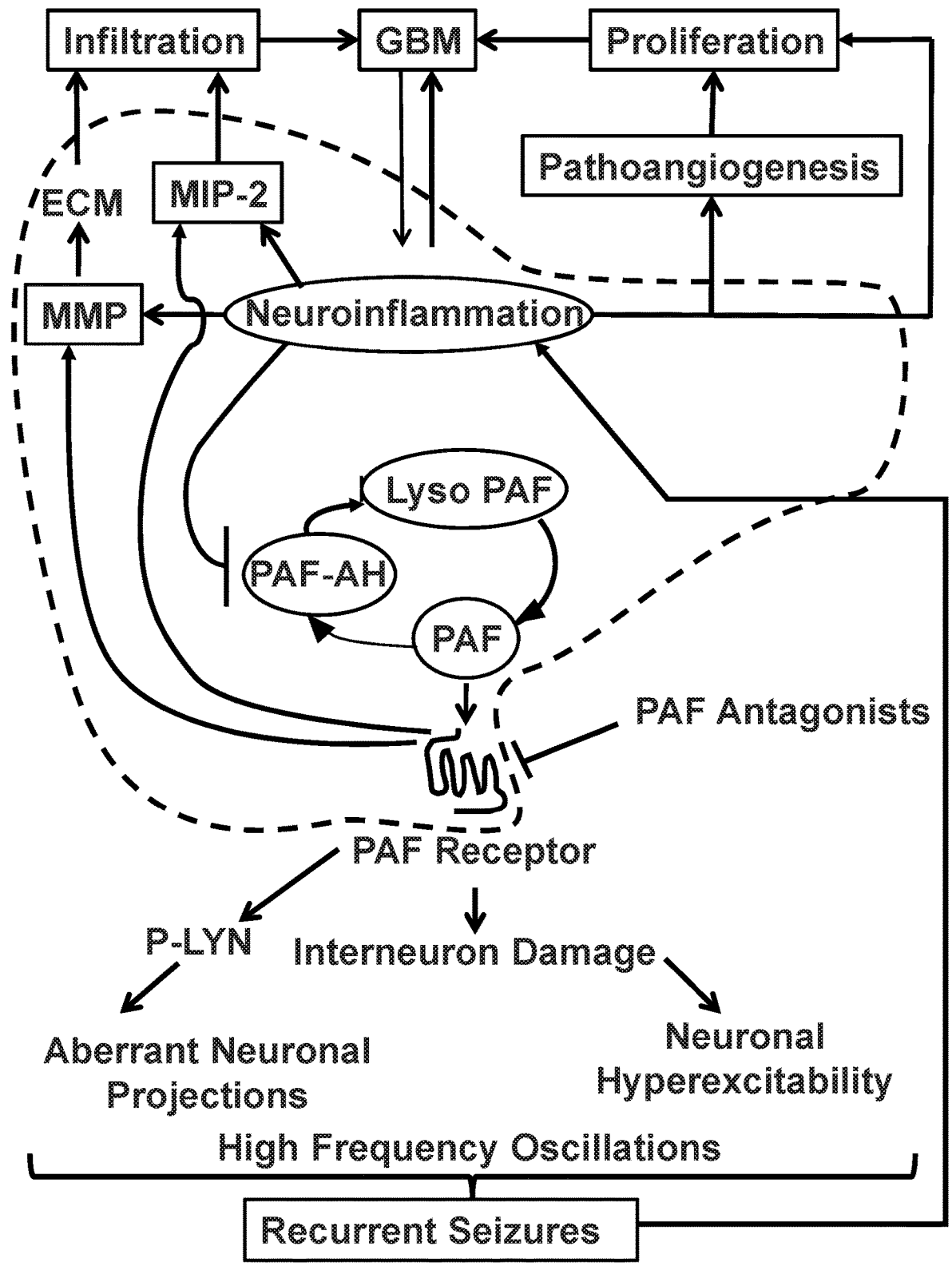
FIG. 1 schematically illustrates the interactions affected by a glioblastoma (GBM) and where Platelet Activating Factor receptor (PAF-r) antagonists can intercede. GBM promotes neuroinflammation that a): induces docosanoid mediators that directly mediate GBM proliferation and also promote pathoangiogenesis, and b): downregulates PAF acetyl-hydrolase (PAF-AH) that, in turn, contributes to PAF accumulation. Then PAF activates the PAF receptor (PAF-r), which disrupts the extracellular matrix (ECM) and increases macrophage inflammatory protein 2-alpha (MIP-2), exacerbating infiltration of GBM cells, PAF-r activation mediates interneuronal damage, which contributes to neuroinflammation activation that includes Lyn kinase (P-LYN), one of the mediators of network neuronal hyper-excitability and aberrant projection and the onset of recurrent seizures. This further enhances neuroinflammation.
Figure 2A:
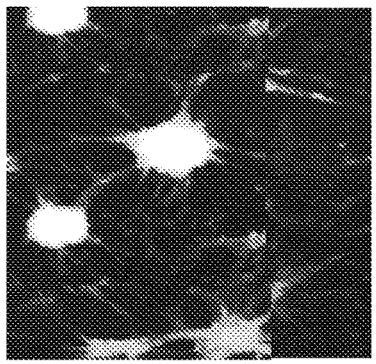
FIGS. 2A-2F illustrate in vivo hippocampal GBM progression.
Figure 2B:
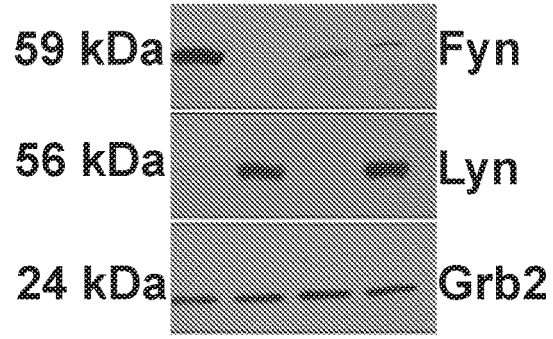
Figure 2C:
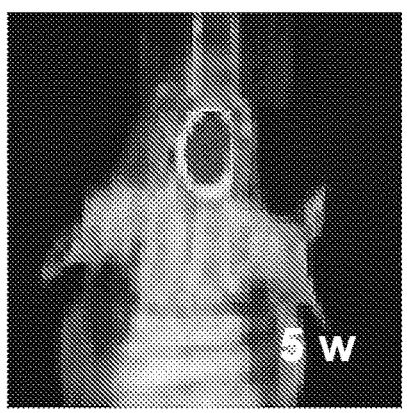
Figure 2C:
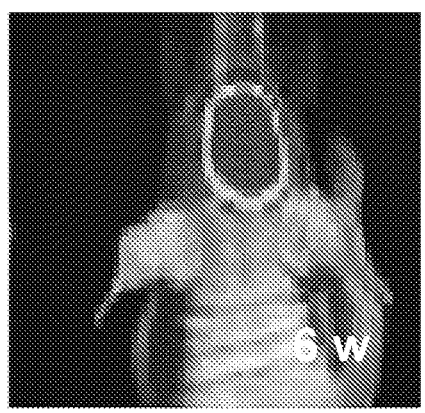
Figure 2D:
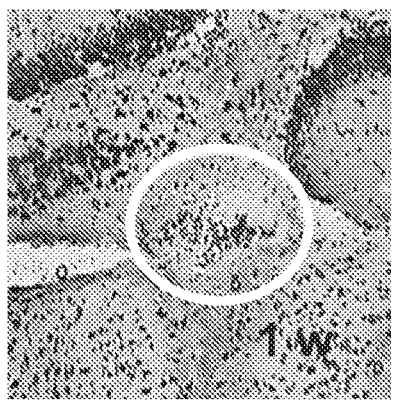
Figure 2D:
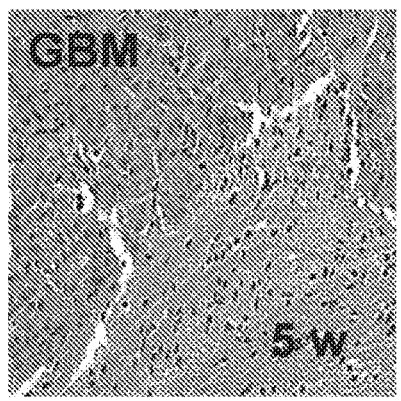
Figure 2E:
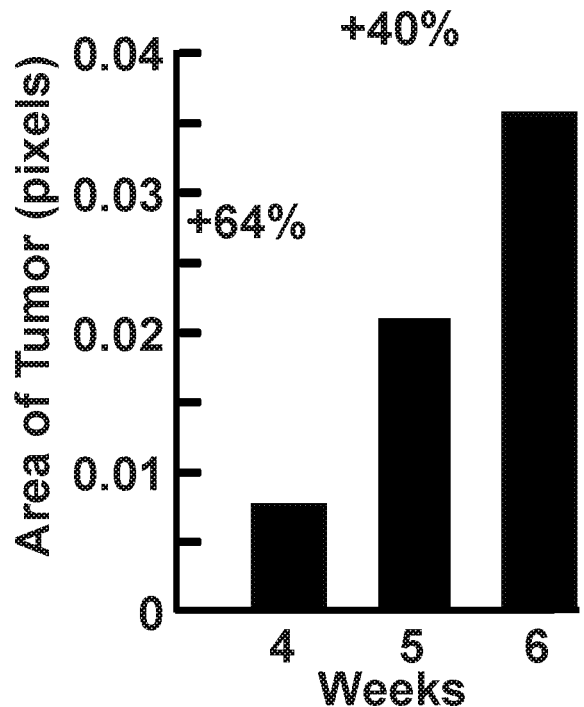
Figure 2F:
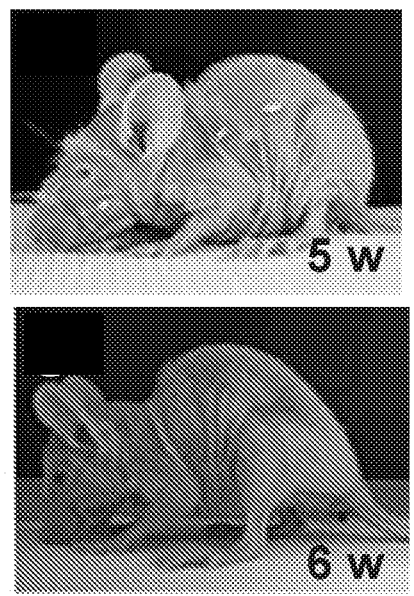
Figure 3A:
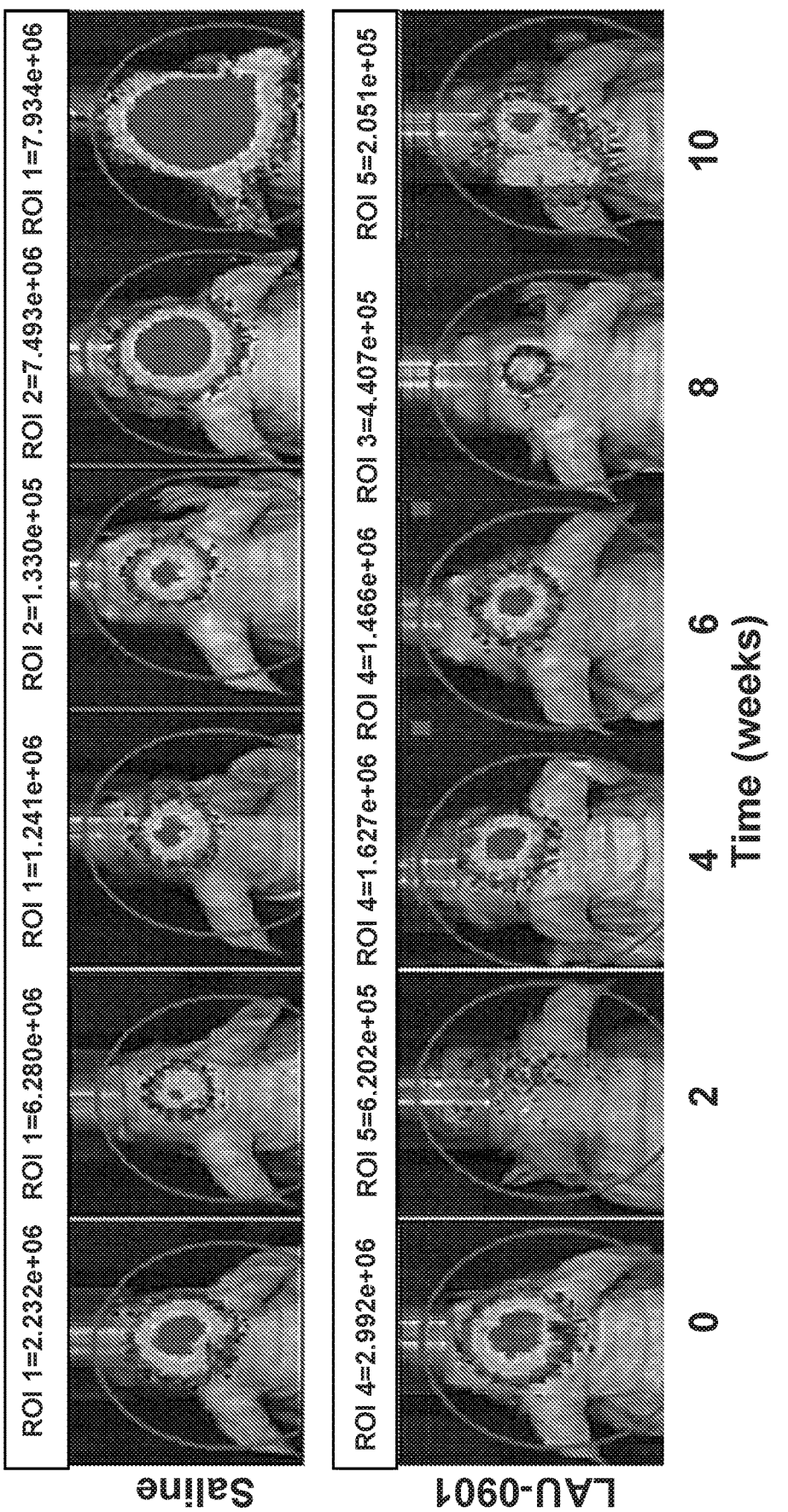
FIGS. 3A-3C illustrate that a PAF-r antagonist reduces GBM tumor size. U87MG cells were implanted in the right dorsal CA3 hippocampal region of BALB/c (nu/nu) mice. Intracranial tumor growth was quantified using Jo vivo bioluminescent imaging on days 10 and 25. Saline (vehicle) or LAU-0901 (60 mg/kg/day; i.p., n=6 in each group) was administered daily from day 10, during 5 days.
Figure 3B:
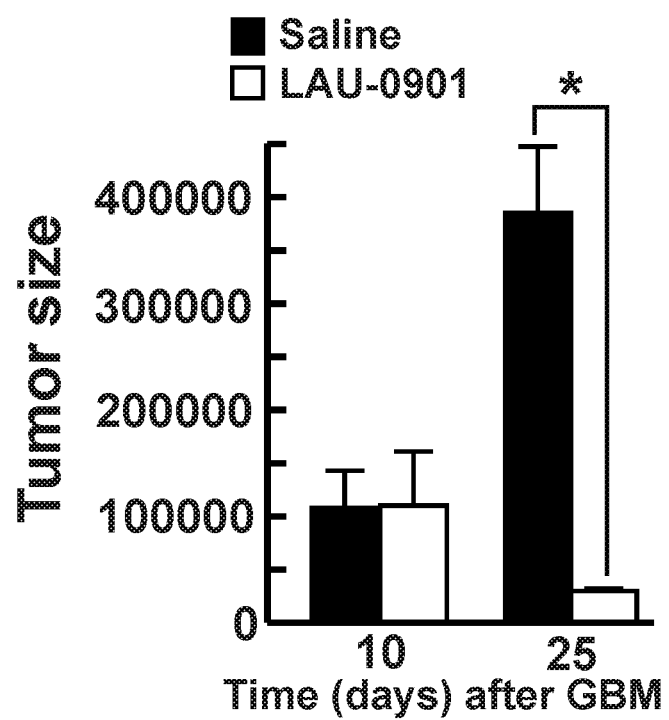
Figure 3C:
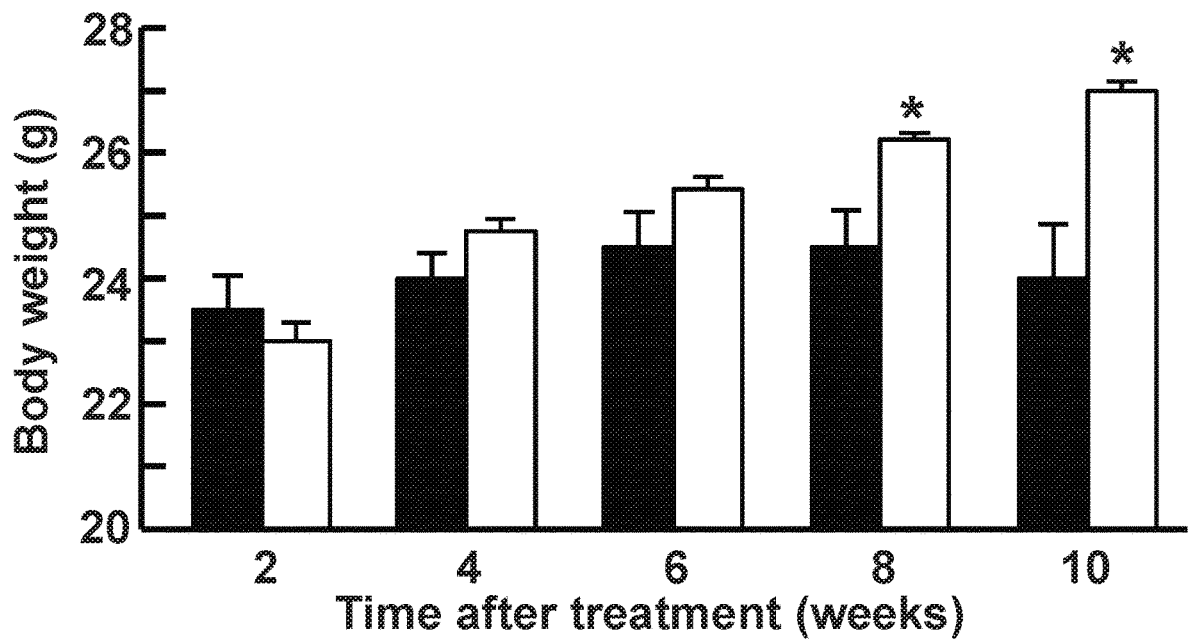

GBM is a malignant brain tumor with rapid growth and infiltration, high resistance to current therapies, and a poor survival rate (Prakash et al., 2012; Verlosick et al., 1991), Seizures arise in the peritumoral area of an experimental GBM model (Campbell et al., 2012; Kohling et al., 2006; Buckingham et al., 2011). However, it is not clear how GBM leads to local neuronal network disorganization that facilitates clinically recurrent seizures and cognitive impairment or if recurrent seizures themselves exacerbate GBM growth. Different components of neurotransmission associated with the GBM-induced seizures have been postulated (de Groot et al., 2012; Prakash et al., 2012). However, most of them attempt to regulate the threshold of seizures but not epileptogenesis, which is presumed to involve chronic re-shaping of neuronal circuitry (Bazan and Musto, 2015; Musto and Samii, 2011; Musto et al., 2009; Musto et al., 2015). Also, cognitive dysfunction in GBM patients support neuronal network deficit (Douw et al., 2009; Douw et al., 2010). Therefore identification of therapeutically targetable mechanisms of GBM invasiveness, such as shown in FIG. 1, contributes to counteracting tumor growth as well as consequences such as control of seizures. In the in vivo model of GBM it has now been observed that epileptiform activity and dynamic changes of neuronal networks during GBM invasiveness (FIGS. 3A-3D, 5, 6A-6D, 7, and 14-16) that appear to be similar to the onset of seizure susceptibility and cognitive deficits in as seen GBM patients (Bartolomei et al., 2006; Douw et al., 2010).

Example 10

The peritumoral inflammatory-microenvironment contributes to invasiveness into the neuronal network in GBM: GBM cellular invasiveness is considered a possible cause of anti-GBM therapy resistance. Also, infiltrated GBM cells are associated with seizures and are difficult to completely eradicate surgically or with local therapeutic modalities.

Several molecular and cellular peritumoral factors have been described (Prakash et al., 2012). However, inflammation-induced recurrent seizures (Aronica et al., 2008; Musto and Samii, 2011; Vezzani and Friedman, 2011) might mediate GBM-invasiveness (FIG. 7) to neural terminals that contribute to the alteration of cyto-architecture, neuronal dysfunction (FIG. 7) and modification of receptors involved in neuronal excitability in GBM (Goel et al., 2003; Kohling et al., 2006; Shamji et al., 2009).

It has been shown that PAF-r antagonism reduces neuroinflammation and also attenuates seizure susceptibility (Musto and Samii, 2011; Okubo et al., 2012; Hasegawa et al., 2010, Marotta et al., 2009). The data of the present disclosure show that PAF-r antagonism limits neuroinflammation and aberrant neuronal network formation, as shown in FIG. 11A-11C). Accordingly, PAF receptor (PAF-r) is a candidate to target with selective antagonists to counteract GBM growth and invasiveness, and to determine how it impairs neuronal networks.

Example 11

Experimental Design and Methods: PAF-r deficient and wild type mice and athymic nude mice, 6 to 8 weeks of age (Harlan Laboratories) mice were used. The xerograph GBM mouse model is representative of this tumor, which has a narrow survival window. These cells form a massive and homogenous mass from tumor-initiating cells, are localized, and invade neuronal tissue. This model is a predictor of therapeutic responses in human glioblastoma patients. U87MG cells (FIGS. 2A-3C) with a luciferase reporter gene were injected ($5\times10^5$ cells in 5 ml serum-free DMEM) into the right dorsal CA3 hippocampal region (coordinates: 2.5 mm lateral, 1.7 mm posterior to the bregma, and 1.5 depth) of mice (6-8 wks of age) (Marrero et al., 2014).

GBM cells were implanted in the dorsal hippocampus because: 1) GBM has increased incidences in the temporal lobe (Larjavaara et al., 2007; Zada et al., 2012); 2) the temporal lobe is prone to epileptogenesis (Engel et al., 2011); 3) the temporal lobe is susceptible to induced seizures following stimulation (Musto and Samii, 2011; Musto et al., 2009); 4) it reflects a well-known neuronal cell organization (Kiausberger, 2009); and 5) it has a particular neuronal network description in the dorsal hippocampus of the mouse under physiological (Buzsaki et al., 2003) and pathological (Musto et al., 2015) conditions.

Example 12

In vivo imaging analysis: Intracranial tumor growth was quantified by bioluminescent imaging using an in vivo imaging system and procedures as described by Marrero et al., 2014, incorporated herein by reference in its entirety.

Example 13

Multiarray electrodes, local field potential recording and seizure analysis: Silicon probes were implanted in the dorsal hippocampus (FIGS. 5 and 6A) (coordinates: 1.5 mm lateral and 1.7 mm posterior to the bregma and 2 mm depth). Then pre-amplified headstage (16 HST; Piexon, Dallas, TX) were connected to the probe 24 h after surgery. Local field potentials (LFP) and spike units were recorded simultaneously with computerized assessment of behavior for locomotor activity (Desland et al., 2014) using MAP data acquisition system (Piexon, Dallas, TX) in freely-moving mice (Musto et 2015). Frequencies for delta (0.1-3.9 Hz), theta (4-8 Hz), beta (13-20 Hz), low gamma (21-40 Hz), and bands from 200-300 Hz could be analyzed from LFP (amplified (1000×), band-pass filtered (0.1-300 Hz) and digitalized at 1 KHz using Neuroexplorer (Nex Technologies, Madison, AL).

Identification of putative electrical profiles of pyramidal and inter neuron cells using extracellular features (Bartho et al., 2004) could be determined. Briefly, frequency analysis of oscillatory activity, including high frequency oscillations and micro-epileptiform activity, was calculated using NeuroExplorer following procedures previously described (Musto and Samii, 2011; Musto et al., 2015).

The number and characterization of seizures, including frequency and pattern distribution at different time points after GBM implantation, were determined and correlated with Racine's score (Musto et al., 2011; Musto et al., 2009; Musto et al.,—2015). Field activity and population discharge of neurons were correlated. The cross-correlograms of cell pairs during HFO bursts and between HFO and non-HFO events were averaged and then HFO phase modulation of pyramidal and interneuronal cells was analyzed according Buzsaki et al., 2003.

Example 14

Figure 9:
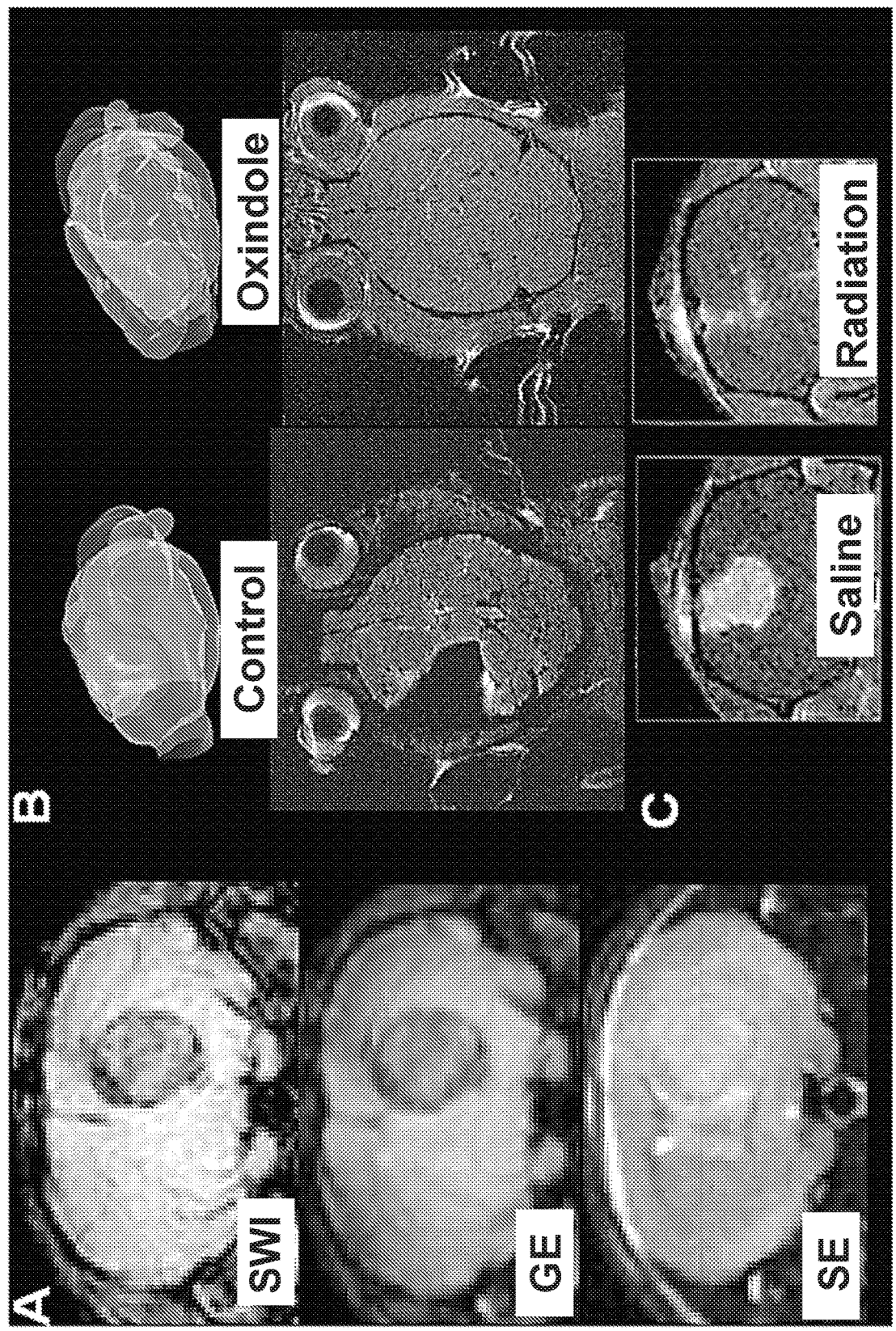
FIG. 9 illustrates neuroimaging of GBM. Panel A (top-to-bottom) compares the efficacy of various imaging modalities that can improve visualization and quantification of GBM for therapeutic assessments. Susceptibility weighted imaging (SWI, flow compensated) outperformed gradient echo (GE) and standard spin echo (SE) imaging. Panel B (left, right) shows SWI imaging can be used to monitor GBM therapy when evaluating Oxindole (anti-proliferative effects on the vasculature) treatments, which allowed documentation of reduced tumor burden. Panel C (left, right) shows standard contrast-enhanced T1-weighted and T2-weighted imaging can be used to assess tumor growth along with neuroinflammation. This example illustrates the retardation of GBM growth after proton radiation therapy (30 Gy, single dose) after injection of a gadolinium contrast agent.
Figure 10:
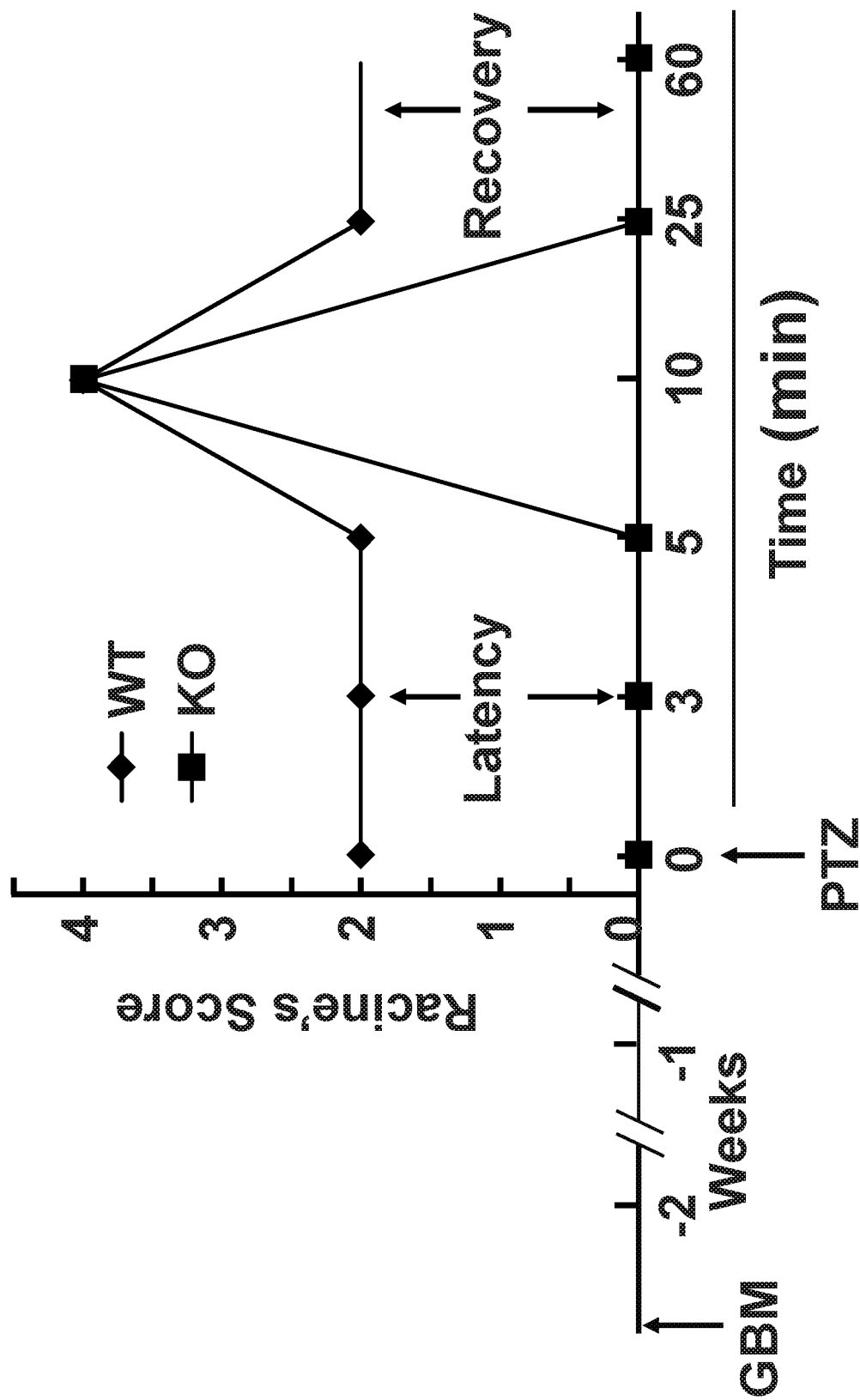
FIG. 10 illustrates that PAF Receptor (PAF-r) deficiency attenuates seizures during GBM growth. GBM cells were implanted in the hippocampus of PAF-r knockout (KO) or wild-type (WT) mice, PTZ (35 mg/kg) was administered 2 weeks tater. PAF-r knockout (KO) mice had a prolonged latency and a faster recovery compared to WT mice. Values are means±SD; *P<0.05 (two-way repeated-measures ANOVA): n=3 in each group.

Neuroimaging: Ex vivo brains underwent high resolution (11.7 T Bruker Avance MRI) neuroimaging at the appropriate time points. Two imaging modalities were utilized, a T2-weighted imaging (T2WI) sequence for neuroinflammation (edema, etc.) and tumor volumes and a susceptibility weighted imaging (SWI) sequence that is hyper-sensitive to blood within tumors, as seen in FIG. 9 for enhanced tumor volumes and tumor tissue metrics. The T2WI imaging sequence parameters are (TRITE=2357.9/10.2 msec matrix size=256×256; field of view (FOV) 2 cm while the SWI sequence is comprised of a TRITE=617.7/7 msec; matrix size=256×256; FOV 2 cm. T2 images were processed as described by Obenaus et al., 2011 for quantitative T2 values. For SWI SPIN (Signal Processing in Nuclear Magnetic Resonance, MRI Institute, Detroit, MI) was use to enhance SWI magnitude images using minimum-intensity-projection (MIP) filters computed from SWI phase images and resultant maps. Minimum intensity Projections (MIPs) are generated to increase contrast and enhance areas containing tumors and tumor level metrics. Computed SW MIPs can then automatically analyzed for regions containing tumor tissues using Hierarchical Region Splitting (Ghosh et al 2012, 2014).

Example 15

Novel Object Recognition (NOR) task: This method was used to evaluate cognition, particularly recognition memory as described previously (Rossi et al., 2013), and as shown in FIGS. 11A-11C, at different time points after GBM implantation.

Example 16

Pro-inflammatory molecular analysis: LC-MS/MS-based mediator lipidomic analysis will be evaluated as described previously (Musto et al., 2011, Musto and Samii, 2011), chemokine analysis was performed using commercial enzyme-linked immune-absorbent assay (Rodent MAPs Myira RBM, USA), and matrix metalloproteinase (MMP) activity were investigated by gelatin zymography assay (Ramaswamy et al., 2014).

Example 17

Brain samples: Brain samples were collected at days 7, 12, and 35 after GBM cell implantation because GBM invades and disrupts the neuronal network as shown in (FIGS. 6A-6D) before extensive GBM growth, and minor clinical cachexia, which allows us to monitor locomotor activity, seizure susceptibility and memory tests. For histology studies and biochemical analysis, brains were dissected according to previous procedures (Musto et al., 2009, 2011), and the ipsilateral (with GBM xerography) and contralateral hippocampus will be dissected from the brain following previous procedures (Cole-Edwards et al., 2006; Musto et al., 2011). In addition, the GBM core and peritumoral areas were separated using laser micro-dissection.

Example 18

Pentylenetetrazol test: The systemic administration of pentylenetetrazol (PTZ) in rodents, an accepted model to test the potential anti-convulsive effect (Loscher, 2011) was used to evaluate seizure susceptibility in mice with GBM cell implantation. It has been seen that systemic administration of PTZ at 35 mg/kg is useful as a sub-convulsive dose to evaluate seizures after brain damage. Animals were placed in individual Plexiglas cages (28×28×37.5 cm) and then a single dose of PTZ (Sigma, St. Louis, MO) at 35 mg/kg were administered intraperitoneally (i.p.) to each animal. Locomotor seizures were quantified according to a modified Racine's Score classified as previously described (Musto et al., 2009, 2011).

Example 19

Histology and immunohistochemistry: GBM cells were evaluated as follow: 1) pleomorphic and hyperchromatic nuclei and the scant cytoplasm using cd32, vimentin K6 for cellular proliferation (Marrero et al., 2014) and CD57$^+$ cells as a marker of invasiveness, together with MAP-2 for neuronal fibers and IL-1a for microglia cells. Also, PAF-r. PAF-AH were co-localized with GFAP, Ilba1, and MAP-2 for astrocyte, microglia and neurons respectively. Assessment for invasiveness was by the number of GBM cells per segment of individual dendrite (100 mm)/neuron outside from the GBM core (FIG. 7).

Example 20

Statistical Methods, Sample Sizes and Power Analysis: An experimenter blinded to the experimental conditions performed the analysis. Animals were randomly allocated to experimental groups, and data acquisition and analysis performed in a blinded manner. Multiple comparisons of treatment means and treatment by time interaction means (where used in particular experiments) were analyzed by appropriate models in the analysis of variance. Post-hoc comparisons between means will be conducted using t-tests with alpha level adjustment done by a method of simulation based on the number of planned comparisons (Edwards and J., 1987). Differences are considered significant at an alpha level of 0.05. Power analyses on preliminary data suggest that, based on the anticipated differences and data variance, 12 animals/group are required to achieve a power of 0.85-0.9 in experiments involving behavioral scores, tumor and infiltration areas, chemokines, lipidomic data and cell numbers as outcomes. All of these outcome variables could be dealt with under the assumption of asymptotic normality where sample sizes are adequate.

Example 21

The relationship of the PAR-receptor with growth and invasiveness of GBM using PAF-r KO as well as PAF-r antagonists. Both show definitive beneficial effects on GBM progression (as shown in FIGS. 3A-3C, 8, and 10). The relationship of GBM with the neuroinflammatory milieu created by the multiple PAF-mediated neuroinflammatory events provides clues about new mechanisms to counteract GBM progression. A series of PAF antagonists that access the brain when given systemically (FIG. 13) has also been identified that may elicit longer acting bioactivity.

Example 22

Figure 4:
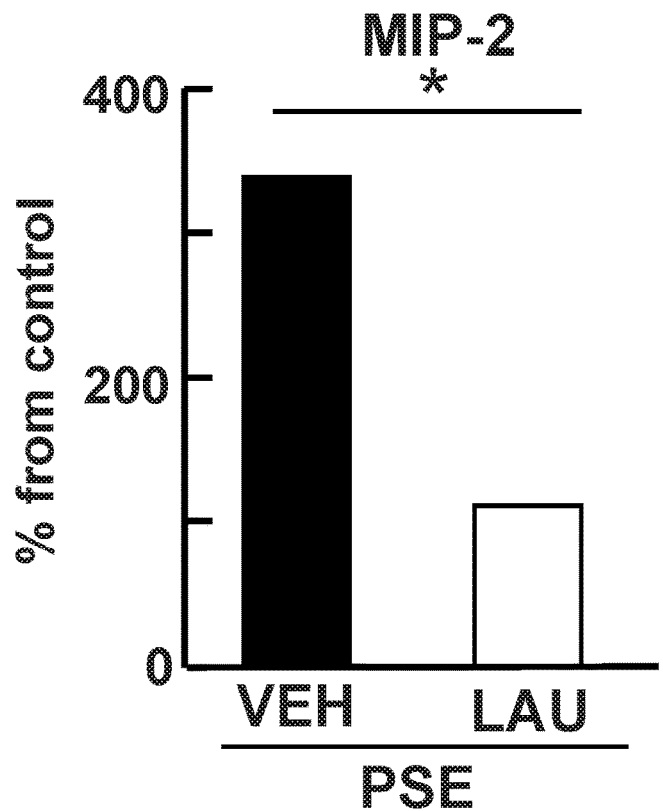
FIG. 4 is a graph illustrating that a PAF-r antagonist limits chemokine MIP-2. MIP-2 increased in the hippocampus after neuroinflammation induced by systemic administration of lipopolysaccharide (LPS) one week after status elepleticus (SE). LAU-0901 (60 mg/kg/daily for 5 days; i.p.), reduced hippocampal levels of MIP-2 compared with saline (n=5 in each group). MIP-2 was measured using bead-based immunodetection. Values are means±SD: *$P<0.05$ (two-way repeated-measures ANOVA).
Figure 5:
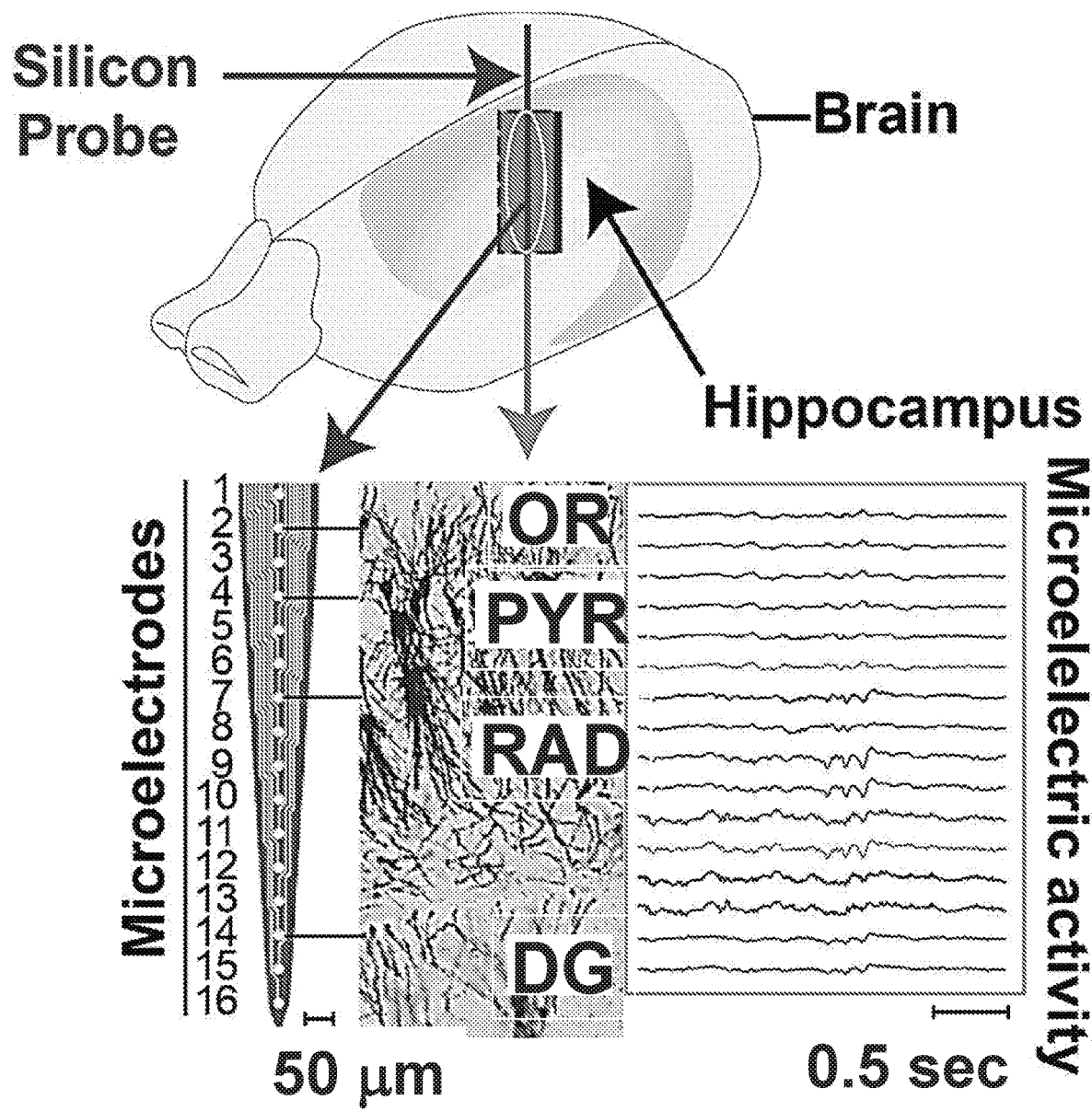
FIG. 5 illustrates hippocampal local field potential recordings in freely-moving animals. A silicon probe with 16 microelectrodes, implanted in the hippocampus (yellow) of mouse brains was used to obtain spontaneous electrical activity of a small area of neurons. A representation of silicon probes, microelectrodes and their relationship with neuronal cells (in black) from each hippocampal sub-region (SO, stratum oriens; PYR, pyramidal layer; RAD, stratum radiatum; DG, dentate gyrus) and electrical traces is presented.
Figure 6A:
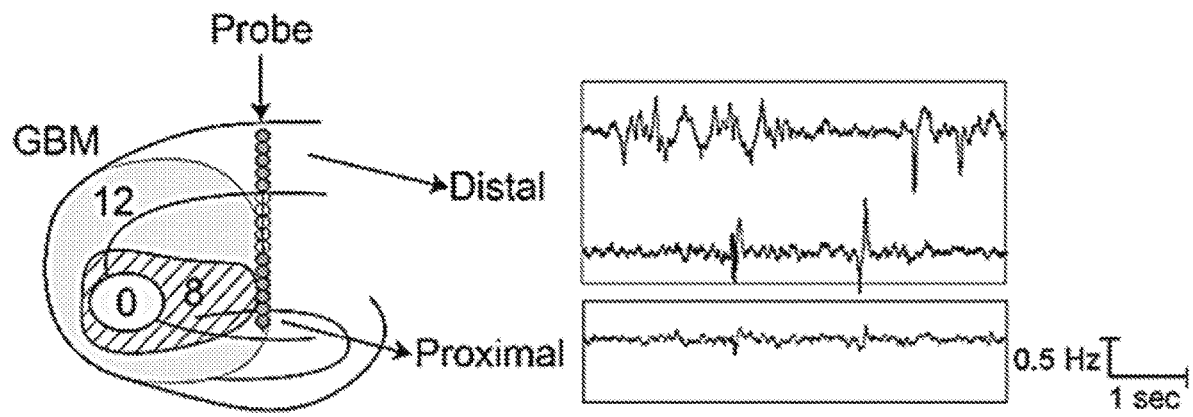
FIGS. 6A-6D illustrate that a hippocampal-located GBM induces seizures before extensive GBM growth.
Figure 6B:
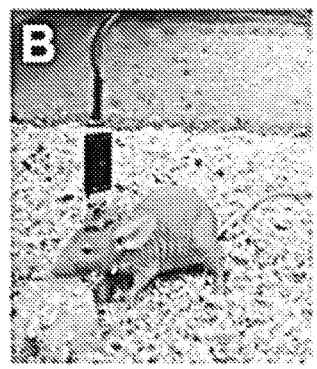
Figure 6C:
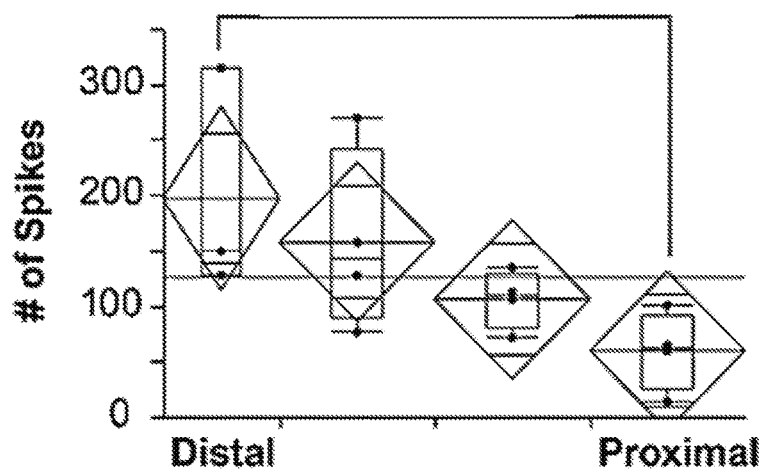
Figure 6D:
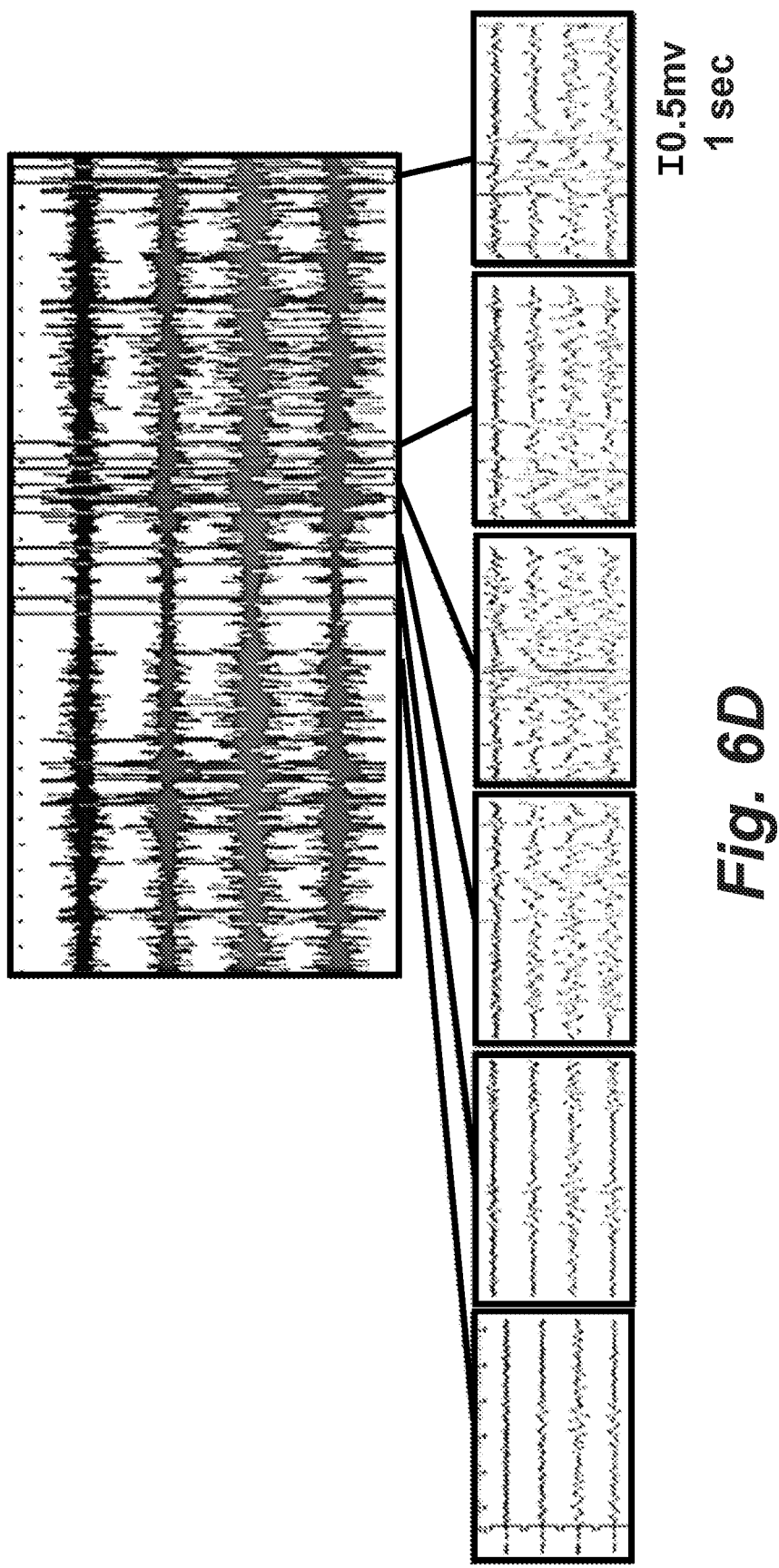

GBM invasiveness induced aberrant neural projections: The mechanism of GBM-mediated impairments of neuronal networks needs to be elucidated to understand GBM invasiveness (FIGS. 4 and 5). For this purpose, PAF-r deficient and wild type mice with GBM were use. Most of the components of the local field potentials (FIGS. 4 and 5) arise from post-synaptic terminals (Buzsaki, 2010 Musto et al., 2015) located in dendritic spines (Yuste & Urban, 2004). Sic kinase, Src-family of kinases (SFKs) (Bernard-Trifilo er al., 2005) and Lyn play important roles in synaptic transmission (Umemori et al., 2003) and plasticity, and interact with PSD-95 (Kalia & Salter, 2003). Inflammation activates the Src family of kinase-dependent pathways that mediates glutamate-seizure severity (Balosso et al., 2008). Lyn increases in synaptic terminals in epilepsy, and we postulate that it mediates aberrant spine formation. Also, these formations are attenuated by PAF-r antagonism.

GBM cells were implanted into PAF-r deficient or wild type mice. Lyn kinase inhibitor (Dasatinib; 0.01 mL/g) (Luo et al., 2000) or vehicle (propylene glycol/water) was administered intraperitoneally at 14 d after GBM implantation and continues for 14 d. Alternatively, BALB/c, (nu/nu) mice received LAU-0901 (60 mg/kg; i.p.) or saline daily for 5 days (n=4-5 per group) 24 h after SE. Weight, locomotion, survival rate, behavior, in vivo tumor growth, and GBM cells were analyzed.

Cyto-architecture hippocampal neurons, dendrites and dendritic spines was evaluated using rapid Golgi staining and the DIOLISTIC labeling approach, as shown in FIG. 12A. Then dendrites and dendritic spines from pyramidal cells were reconstructed, analyzed, and visualized in a 30 shape of neurons from the ipsi and contralateral hippocampal region using light and confocal microscopy, digitally-traced, mediated computational analysis. PAF was measured by LC-MS/MS. PSD-95, and p-Lyn were evaluated from hippocampus, including actin organization, using Western blot analysis. Correlation analysis between GBM cells and aberrant fibers will be conducted. 2 groups, n=12 per group, 2 treatments, 2 points (immunohistochemistry and lipidomics). Total=96 mice.

PAF-r deficiency counteracts infiltrated GBM cells in dendrites, limiting aberrant spinogenesis mediated by the Src tyrosine kinase family through activation of Lyn in dendrites. PAF-r antagonism will limit formation of aberrant dendrites.

REFERENCES

Addae et al., *Differentiation* (2012) 83(5):233-241
Akai et al., *J. NeuroOncology*. (2002) 59(3): 193-198
Alvarado-Rajas et al., *Annals Neurol*. (2014)
Aronica et al., *Neuroscience*. (2008) 151(1):272-292
Balosso et al., *Brain*. (2008) 131 (Pt 12):3256-3265
Bartho et al., *J. Neurophysiol*. (2004) 92(1):600-608
Bartolomei et al., *Annals Neurology*. (2006) 59(1):128-138
Bausch S B. (2005) 7(3):390-400

Bazan & Tao J. *Ocular Pharmacol. Therapeutics* (1997) 13(3):2-285
Bazan N G. *Mol. Neurobiol.* (2005) 32(1):89-103
Bazan N G, *Ceil. Mol. Neurobiol.* (2006) 26(4-6):901-913
Berdiev et al., *J. Biol. Chem.* (2003) 278(17):15023-15034
Bernard-Trifilo et al., *J. Neurochem.* (2005) 93(4):834-849
Blasiak et al., *BMC Med. Imaging.* (2013) 13:20
Buckingham et al., *Nature Med.* (2011) 17(10):1269-1274
Buzsaki G. *Neuron* (2010) 68(3):362-385
Buzsaki et al., *Neuroscience* (2003) 116(1):201-211
Campbell et al., *J. Neural Engineering.* (2012) 9(2):026023
Chagnac-Amitai & Connors *J. Neurophysiol.* (1989) 62(5): 1149-1162
Chaichana et al., *J. Neurosurgery.* (2009) 111(2):282-292
Chao & Olson *Biochem. J.* (1993) 292 (Pt 3):617-629
Cole-Edwards et al., *J. Neuroscience* (2006) 26(32):8295-8304
Coquery J. *Cerebral blood Flow Metabolism* (2014) 34(8): 1354-1362
Costa et al., *Oncotarget.* (2014)
da Fonseca & Sadie *Clinical Developmental Immunol.* (2013) 2013:264124
Das & Marsden *New Eng. J. Med.* (2013) 369(16):1561-1563
Davenport et al., *Experimental Neurol.* 1990) 109(2):180-90
Dawson et al., *Nature Comm.* (2012) 3:936
de Groot et al., *Brain* (2012) 135(Pt 4):1002-1016
Desland et al., *J. Central Nervous System Dis.* (2014) 6:7-14
Douw et al., *Lancet Neurol.* (2009) 8(9):810-8
Douw et al., *Frontiers Hum Neurosci.* (2010) 4:174
Edwards & Berry *Biometrics.* (1987) 43(4):913-928
Ehtesham et al., *J. neuro-oncology.* (2013) 113(2): 153-162
Engel et al., *Int. J. Physiol. Pathophysiol. Pharmacol.* (2011) 3(1):38-47
Englot et al., *Neurosurgery Clinics North Am.* (2012) 2342): 227-235
Escoubas et al., *Biochimie.* (2000) 82(9-10):893-907
Farooqui A A. *Neuroscientist* (2009) 15(4):392-407
Flasinski et al., *J. R. Soc Interface.* (2014) 11(95):20131103
Garau et al., *Cytokine Network.* (2006) 17(1):35-41
Gati et al., *Prostaglandins Leukot. Essent. Fatty Acids.* (1991) 43(2): 103-110
Glantz et al., *Neurology.* (2000) 54(10):1886-1893
Ghosh et al., *J Cereb. Blood Flow Metab.* (2012) 32(12): 2161-2170
Ghosh et al., *Med. Image. Anal.* (2014) 18(7):1059-1069
Goel et al., *Neuropathol.* (2003) 23(4):262-270
Gomes et al., *Shock* (Augusta, Ga.). (2006) 26(1):41-49
Goracci et al., *Handbook or Neurochemistry and Molecular Neurobiology*: Springer US) (2010) p. 311-352.
Gruol et al., *Brain Res.* (1980) 183(1):247-252
Hanahan O J. *Ann. Rev. Biochem.* (1986) 55:483-509
Hattermann et al., *J. Neuroimmunol.* (2013) 260(1-2):47-54
He et al., *Ophthalmol.* (2006) 124(1):70-8
He et al., *Current Eye Res.* (2010) 35(12):1063-1071
Hirashima et al., *Blood.* (1999) 93(4):1253-1263
Houser & Escalapez *Epilepsy Res.* (1996) 26(1):207-218
Hu et al., *Neurooncol.* (2015) 17(2):200-210
Hu et al., *Int. J. Cancer* (2014) 135(11):2569-2578
Jancar & Chammas *Curr Drug Targets.* (2014) 15(10):982-987
Jeffes et al., *J Immunol.* (2005) 174(5):2533-2543
Kalia L V, Salter M W, *Neuropharmacol.* (2003) 45(6):720-728
Kapoor & O'Rourke *Oncogene.* (2010) 29(29):4130-4144
Kerkhof & Vecht *Epilepsia.* (2013) 54 Suppl 9:12-17
Kim et al., *Development.* (2014) 141(16):3233-3242
Kim et al., *J. Lipid Res.* (2013) 54(10):2678-2686
Klausberger T *Euro. J. Neuroscience.* (2009) 30(6):947-957
Kohling et al., *Neurobiol. Disease.* (2006) 22(1):64-75
Koltai et al., *Drugs.* (1991) 42(1):9-29
Kornecki & Ehrlich *Science* (1988) 240(4360):1792-1794
Krishtal O *Trends Neurosci.* (2003) 26(9):477-483
Kuruvilla et al., *J. immunol.* (1994) 153(12):5433-5442
Kweon & Suh *BMB Reports.* (2013) 46(6):295-304
Lacerda-Queiroz et al., *Am. J. Pathol.* (2012) 180(1):246-255
Larjavaara et al., *NeuroOncol.* (2007) 9(3):319-325
Li et al., *BioMed. Res. Int.* (2014) 2014:762126
Loscher W. *Seizure.* (2011) 20(5):359-368
Lu et al., *Neuropsychopharmacol.* (2010) 35(11):2238-2248
Luo et al., *Clin Cancer Res.* (2006) 12(23):7180-7186
Lv et al., *Epilepsy Res.* (2011) 96(1-2):74-80
Marotta et al., *Biochem Pharmacol.* (2009) 77(7):1223-1235
Marrero et al., *Neoplasia.* (2014) 16(10):874-82
Mazereeuw et al., *J. Neuroinflammation.* (2014) 11 119
Munson et al., *Cell Cycle.* (2013) 12(14):2200-2209
Musto et al., *Epilepsia.* (2011) 52(9):1601-1608
Musto et al., *Epilepsy Res.* (2009) 85(2-3):199-205
Musto et al., *PloS One.* (2015) 10(1):e0116543
N'Gouemo P. *Brain Res.* (2008) 1222:230-232
Najbauer et al., *PloS One.* (2012) 7(4):e35150
Nelson et al., *Mol Cancer.* (2015) 14:13
Obenaus et al., *Ann Neural.* (2011) 69(2):282-291
Okubo et al., *Mol Pain.* (2012) 8:8
Ottine & Bazan H E, *Current Eye Res.* (2001) 23(2):77-85
Otto et al., *J. Neurosci Res.* (2000) 60(6):7337-42
Pagliara et al., *Biochimica Biophysica Acta.* (2014) 1843 (11):2631-2644
Prakash et al., *Medical Hypotheses.* (2012) 79(5):622-626
Racine R J *Electroencephalogr. Clin. Neurophysiol.* (1972) 32(3):269-279
Racine R J. *Clin. Neurophysiol.* (1972) 32(3):281-94
Ramaswamy et al., *Neurological Sci* (2014) 35(6):823-829
Richter et al., *Neurosci. Lett.* (2014) 583:130-135
Rosati et al., *J. NeuroOncology.* (2009) 93(3):395-400
Rossi et al., *J. Neurotrauma.* (2013) 30(19):1672-1679
Sadoshinia & Okada *Fukuoka Igaku Zasshi* (*Hukuoka Acta Medica.* (1992) 83(10):363-366
Sanabria et al., *J. Physiol.* (2001) 532(Pt 1):205-216
Scatena R *Expert Opinion Investigational Drugs.* (2000) 9(9):2159-2165
Scott & Gibberd *Acta Neurologica Scandinavica.* (1980) 61 (4):227-239
Sfondouns et al., *Computers Biol. Med.* (2012) 42(1): 129-134
Shamji et al., *Neurosurg Rev.* (2009) 32(3):275-284
Somjen G G. *Brain Res.* (1984) 311(1):186-188
Souza et al., *J. Immunol.* (2004) 173(6):4137-4146
Stafforini et al., *Critical Reviews Clin. Lab. Sci.* (2003) 40(6):643-672
Tsoupras et al., *Infectious Disorders Drug Targets.* (2009) 9(4):390-399
Umemori et al., *Neuroscience.* (2003) 118(3):709-713
Vertosick et al., *Neurosurgery.* (1991) 28(4):496-501
Vezzani & Friedman *Biomark Med.* (2011) 5(5):607-614
Vlachogianni et al., *Cytokine.* (2013) 63(2):97-104
Vukicevic & Kellenberger *Am. J. Physiol. Physiol.* (2004) 287(3):C682-690
Wemmie et al., *Neuron.* (2002) 34(3):463-477
Wemmie et al., *Trends Neurosci.* (2006)29(10):578-586
Xu et al., *J. Biol. Chem.* (2002) 277(13):11368-11374
Yermolaieva et al., *Proc. Nat. Acad. Sci. U.S.A.* (2004) 101(17):6752-6757

Yost et al. *Biochimie.* (2010) 92(6):692-697

Yuste & Urban *J. Physiology, Paris.* (2004) 98(4-6):479-486

Zada et al., *World Neurosurgery.* (2012) 77(3-4):518-524

Zha X M *Mol. Brain.* (2013) 6:1

Zha et al., *Proc. Nat. Acad. Sci. U.S.A.* (2006) 103(44): 16556-16561

Zucker & Cao *Cancer Biol. Therapy.* (2009) 8(24):2371-2373

We claim:

1. A method for treating a seizure caused by a brain tumor, the method comprising the steps:

(a) selecting a subject in need of treatment, wherein the subject has been diagnosed with a brain tumor; and (b) administering a therapeutic composition comprising a therapeutically effective amount of a platelet-activating factor (PAF) receptor antagonist and a pharmaceutically acceptable carrier, wherein the PAF receptor antagonist is:

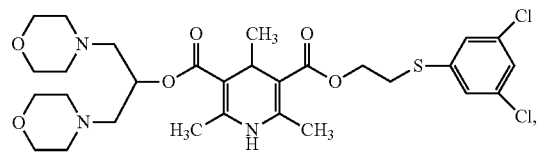

LAU-09015

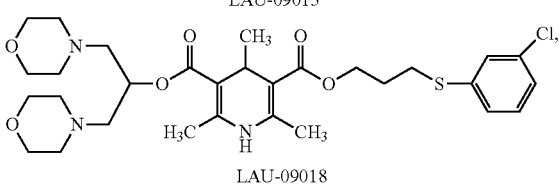

LAU-09018

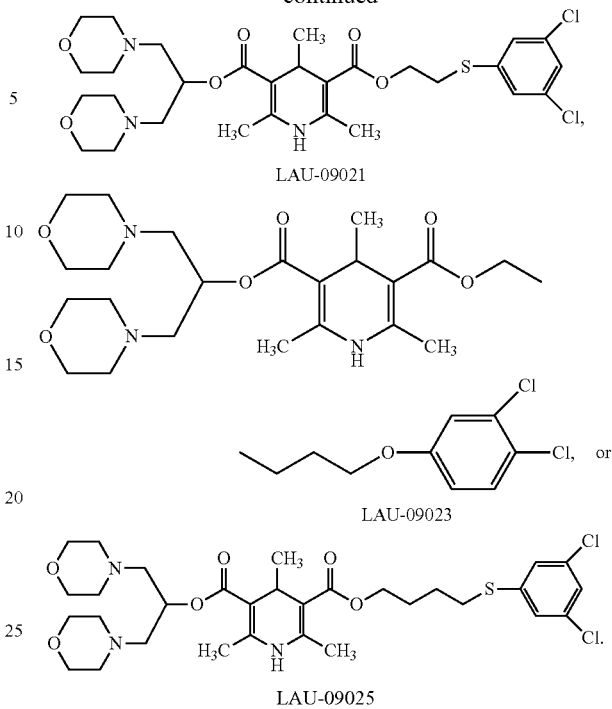

2. The method of claim 1, wherein the brain tumor is selected from the group consisting of: a glioblastoma, an astrocytoma, an oligodendroglioma, an ependymal tumor, a neuronal tumor and a combination of glial tumors.

3. The method of claim 1, wherein the pharmaceutically acceptable salt is an acid addition salt.

4. The method of claim 1, wherein the compound is an R-enantiomer, an S-enantiomer, or a combination thereof.

* * * * *